(12) United States Patent
Pappas

(10) Patent No.: US 12,029,721 B2
(45) Date of Patent: Jul. 9, 2024

(54) COMPOSITIONS COMPRISING CANNABINOIDS AND METHODS OF USE

(71) Applicant: Schedule 1 Therapeutics, Inc., Chicago, IL (US)

(72) Inventor: George D. Pappas, Chicago, IL (US)

(73) Assignee: Schedule 1 Therapeutics, Inc., Chicago, IL (US)

( * ) Notice: Subject to any disclaimer, the term of this patent is extended or adjusted under 35 U.S.C. 154(b) by 0 days.

(21) Appl. No.: 18/208,017

(22) Filed: Jun. 9, 2023

(65) Prior Publication Data

US 2023/0355572 A1     Nov. 9, 2023

Related U.S. Application Data

(63) Continuation of application No. 18/083,824, filed on Dec. 19, 2022, now Pat. No. 11,712,431, which is a continuation of application No. 17/707,542, filed on Mar. 29, 2022, now Pat. No. 11,607,400.

(60) Provisional application No. 63/167,448, filed on Mar. 29, 2021.

(51) Int. Cl.
| | | |
|---|---|---|
| *A61K 31/352* | (2006.01) | |
| *A61K 31/05* | (2006.01) | |
| *A61K 45/06* | (2006.01) | |
| *A61P 25/04* | (2006.01) | |

(52) U.S. Cl.
CPC .......... *A61K 31/352* (2013.01); *A61K 31/05* (2013.01); *A61K 45/06* (2013.01); *A61P 25/04* (2018.01)

(58) Field of Classification Search
CPC .................................................. A61K 31/352
See application file for complete search history.

(56) References Cited

U.S. PATENT DOCUMENTS

| | | |
|---|---|---|
| 2014/0287068 A1 | 9/2014 | Lewis |
| 2018/0344663 A1 | 12/2018 | Vu |
| 2019/0030170 A1 | 1/2019 | Kingsley |
| 2019/0117617 A1 | 4/2019 | Kariman |
| 2020/0330423 A1 | 10/2020 | Brunn |

FOREIGN PATENT DOCUMENTS

| | | |
|---|---|---|
| WO | 2020/115750 A1 | 6/2020 |
| WO | 2020/163866 A1 | 8/2020 |

OTHER PUBLICATIONS

International Search Report and Written Opinion for related PCT Application No. PCT/US2022/022313 dated Jun. 29, 2022, 13 pages.
Baron et al., "Patterns of medicinial cannabis use, strain analysis, and substitution effect among patients with migraine, headache, arthritis, and chronic pain in medicinal cannabis cohort," Journal of Headache and Pain, 2018, 19:37.

*Primary Examiner* — Yong S. Chong
(74) *Attorney, Agent, or Firm* — POLSINELLI PC

(57) ABSTRACT

The present disclosure is related to the use of compositions and their use in reducing and treating pain.

19 Claims, 30 Drawing Sheets

Motor cortex CSD

Half-width

Amplitude

WT
FHM1

COMPOSITIONS COMPRISING CANNABINOIDS AND METHODS OF USE

CROSS-REFERENCE TO RELATED APPLICATIONS

This application is a continuation application of U.S. application Ser. No. 18/083,824, filed Dec. 19, 2022, which is a continuation application of U.S. application Ser. No. 17/707,542, filed Mar. 29, 2022, which claims priority to U.S. Provisional Application No. 63/167,448 entitled "COMPOSITIONS COMPRISING CANNABINOIDS AND METHODS OF USE" filed Mar. 29, 2021, the entirety of each of which is incorporated by reference herein.

STATEMENT REGARDING FEDERALLY SPONSORED RESEARCH OR DEVELOPMENT

This invention was made with government support under Award Number R41DA051309 awarded by the National Institute on Drug Abuse. The government has certain rights in the invention.

FIELD OF THE DISCLOSURE

The present disclosure is related to the use of compositions comprising cannabinoids and their use in reducing pain.

BACKGROUND OF THE DISCLOSURE

In the U.S., more than 38 million people suffer from migraines. This translates into roughly 13 percent of adults in the U.S. population, or slightly more than one in ten people. Of those, 2-3 million migraine suffers are considered chronic.

Fibromyalgia is a common chronic pain disorder. It affects an estimated 10 million people in the U.S. and an estimated 3-6% of the world population. While it is most prevalent in women (75-90 percent of those diagnosed with fibromyalgia are women), it also occurs in men and children of all ethnic groups.

Treatment of migraine pain, frequency, and fibromyalgia pain includes the use of FDA-approved therapies, and non-FDA approved alternative treatments, such as cannabinoids. For instance, current treatments may include the triptan class of drugs, which exert their effect via 5HT-1B/1D receptor agonism, ergotamines, NSAIDs, opioids, simple analgesics, barbiturates, anti-epileptic drugs, tricyclic anti-depressants, COX-2 inhibitors, CGRP inhibitors, beta and calcium channel blockers, anti-hypertensives, antihistamines, onabotulinumtoxinA (Botox®) and others.

Such treatments, however, often fail to help those diagnosed with either disorder. Hence, there is a need in the art for an effective treatment of pain associated with an attack of migraine with and/or without aura, migraine frequency, or fibromyalgia pain as well as related disorders such as familial hemiplegic migraine, sporadic hemiplegic migraine, and complex regional pain syndrome.

SUMMARY

Provided herein is a method of reducing acute migraine pain, photophobia, phonophobia, and/or nausea in a subject, the method comprising administering a pharmaceutically effective amount of at least one minor cannabinoid alone or in combination with tetrahydrocannabinol (THC), cannabidiol (CBD), or both to a subject in need thereof, such that at least one biomarker of central and peripheral sensitization is modulated and migraine pain, photophobia, phonophobia, and/or nausea is reduced in the subject. In some embodiments, the subject is a human.

In some embodiments, the at least one biomarker is selected from the group consisting of N-Methyl-D-Aspartate (NMDA), glutamate, calcitonin gene-related peptide (CGRP), fatty acid amide hydrolase (FAAH), Substance P, 5-hydroxytryptamine (5-HT), nitric oxide (NO), γ-aminobutyric acid (GABA), nerve growth factor (NGF), serotonin, dopamine, N-arachidonoylethanolamine (AEA), 2-arachidonoylglycerol (2-AG).

In some embodiments, the at least one minor cannabinoid is selected from the group consisting of cannabigerol (CBG), cannabigerolic acid (CBGA), cannabinol (CBN), cannabinolic acid (CBNA), $\Delta^9$-tetrahydrocannabivarin (THCV), tetrahydrocannabinolic acid (THCA), cannabichromene (CBC), cannabichromene acid (CBCA), cannabidivarin (CBDV), and $\Delta^8$-tetrahydrocannabinol (D8-THC). In some aspects, the at least one minor cannabinoid is selected from the group consisting of CBG, CBGA, CBN, CBNA, THCV, THCA, CBC, CBCA, CBDV, and D8-THC; and the subject is further administered THC and CBD.

Further provided herein is a method of reducing migraine frequency in a subject, the method comprising administering a pharmaceutically effective amount of at least one minor cannabinoid alone or in combination with THC, CBD, or both to a subject in need thereof, such that at least one biomarker of central and peripheral sensitization is modulated and migraine frequency is reduced in the subject. In some embodiments, the subject has chronic migraines. In some additional embodiments, the subject has high frequency migraines. In some embodiments, the subject is a human.

In some embodiments, the at least one biomarker is selected from the group consisting of NMDA, glutamate, CGRP, FAAH, Substance P, 5-HT, NO, GABA, NGF, serotonin, dopamine, AEA, 2-AG.

In some embodiments, the at least one minor cannabinoid is selected from the group consisting of CBG, CBGA, CBN, CBNA, THCV, THCA, CBC, CBCA, CBDV, and D8-THC. In some aspects, the at least one minor cannabinoid is selected from the group consisting of CBG, CBGA, CBN, CBNA, THCV, THCA, CBC, CBCA, CBDV, and D8-THC; and the subject is further administered THC and CBD.

Further provided herein is a method of reducing fibromyalgia pain in a subject, the method comprising administering a pharmaceutically effective amount of at least one minor cannabinoid alone or in combination with THC, CBD, or both to a subject in need thereof, such that at least one biomarker of central and peripheral sensitization is modulated and fibromyalgia pain is reduced in the subject. In some embodiments, the subject is a human.

Further provided herein is a pharmaceutical composition comprising at least one isolated minor cannabinoid and THC, wherein the ratio of the at least one isolated minor cannabinoid to THC modulates at least one biomarker of central and peripheral sensitization. In some embodiments, the composition further comprises CBD. In some embodiments, the composition further comprises a terpenoid. In some embodiments, the composition further comprises an analgesic agent.

In some embodiments, the at least one biomarker is selected from the group consisting of NMDA, glutamate, CGRP, FAAH, Substance P, 5-HT, NO, GABA, NGF, serotonin, dopamine, AEA, 2-AG.

In some embodiments, the at least one isolated minor cannabinoid is selected from the group consisting of CBG, CBGA, CBN, CBNA, THCV, THCA, CBC, CBCA, CBDV, and D8-THC.

In some aspects the composition comprises at least one cannabinoid is selected from the group consisting of CBG, CBGA, CBN, CBNA, THCV, THCA, CBC, CBCA, CBDV, and D8-THC; THC; and CBD.

Further provided herein is a pharmaceutical composition comprising at least one isolated minor cannabinoid and CBD, wherein the ratio of the at least one isolated minor cannabinoid to CBD modulates at least one biomarker of central and peripheral sensitization. In some embodiments, the composition further comprises THC. In some embodiments, the composition further comprises a terpenoid. In some embodiments, the composition further comprises an analgesic agent.

In some embodiments, the at least one biomarker is selected from the group consisting of NMDA, glutamate, CGRP, FAAH, Substance P, 5-HT, NO, GABA, NGF, serotonin, dopamine, AEA, 2-AG.

In some embodiments, the at least one isolated minor cannabinoid is selected from the group consisting of CBG, CBGA, CBN, CBNA, THCV, THCA, CBC, CBCA, CBDV, and D8-THC.

In some aspects the composition comprises at least one cannabinoid is selected from the group consisting of CBG, CBGA, CBN, CBNA, THCV, THCA, CBC, CBCA, CBDV, and D8-THC; THC; and CBD.

Further provided herein is a method of reducing acute migraine pain, the method comprising administering a pharmaceutically effective amount of a composition comprising THC and CBD to a subject in need thereof such that at least one biomarker of central and peripheral sensitization is modulated and migraine pain is reduced in the subject, while reducing undesired side effects or risk factors of THC. In some embodiments, the subject is a human.

In some embodiments, the composition further comprises at least one minor cannabinoid selected from the group consisting of CBG, CBGA, CBN, CBNA, THCV, THCA, CBC, CBCA, CBDV, and D8-THC.

Further provided herein is a method of reducing migraine frequency in a subject, the method comprising administering a pharmaceutically effective amount of a composition comprising THC and CBD, such that at least one biomarker of central and peripheral sensitization is modulated and migraine frequency is reduced in the subject, while reducing undesired side effects or risk factors of THC. In some embodiments, the subject has chronic migraines. In some embodiments, the subject has high frequency migraines.

In some embodiments, the composition further comprises at least one minor cannabinoid selected from the group consisting of CBG, CBGA, CBN, CBNA, THCV, THCA, CBC, CBCA, CBDV, and D8-THC.

Further provided herein is a pharmaceutical composition comprising THC and CBD, wherein the ratio of THC to CBD modulates at least one biomarker of central and peripheral sensitization while reducing undesired side effects or risk factors of THC.

In some embodiments, the composition further comprises a minor cannabinoid. In some aspects, the minor cannabinoid is selected form the group consisting of CBG, CBGA, CBN, CBNA, THCV, THCA, CBC, CBCA, CBDV, and D8-THC.

In some embodiments, the at least one biomarker is selected from the group consisting of NMDA, glutamate, and CGRP, FAAH, Substance P, 5-HT, NO, GABA, NGF, serotonin, dopamine, AEA, and 2-AG.

In some embodiments, the composition further comprises a terpenoid.

In some embodiments the composition further comprises an analgesic agent.

In some embodiments, the at least one biomarker is selected from the group consisting of NMDA, glutamate, or CGRP.

Further provided herein is a method of treating acute migraine pain, photophobia, phonophobia, and/or nausea, the method comprising administering a pharmaceutically effective amount of a composition comprising at least one minor cannabinoid alone or in combination with THC, CBD, or both to a subject in need thereof, such that migraine pain, photophobia, phonophobia, and/or nausea is reduced in the subject. In some embodiments, the subject is a human.

In some embodiments, the administering is accomplished via injection.

In some embodiments, the treatment is effective within at least 2 hours after administration. In some aspects, the treatment is effective within at least 1 hour after administration, within at least 30 minutes after administration, or within at least 15 minutes after administration.

In some embodiments, the migraine pain is measured by a pain scale.

In some embodiments, the photophobia is measured by the Utah Photophobia Symptom Impact Scale, the Korean Photophobia Questionnaire, or by self-reporting from the subject.

In some embodiments, the phonophobia is measured by self-reporting from the subject.

In some embodiments, the nausea is measured by self-reporting from the subject. In some additional embodiments, the nausea is measured by a visual analogue scale.

In some embodiments, the composition comprises THC and CBD, wherein the ratio of CBD:THC is about 30:1 mg/kg to about 300:1 mg/kg.

In some embodiments, the at least one minor cannabinoid is selected from the group consisting of CBG, CBGA, CBN, CBNA, THCV, THCA, CBC, CBCA, CBDV, and D8-THC.

In some embodiments, the at least one minor cannabinoid, the THC (when present), and the CBD (when present) are at least 90 wt % pure. In some preferred embodiments, the at least one minor cannabinoid, the THC (when present), and the CBD (when present) are at least 99 wt % pure.

In some embodiments, at least one biomarker of central and peripheral sensitization is modulated as a result of the administration. In some aspects, the at least one biomarker is selected from the group consisting of NMDA, glutamate, CGRP, FAAH, Substance P, 5-HT, NO, GABA, NGF, serotonin, dopamine, AEA, and 2-AG.

Further provided herein is a method of treating migraine frequency, the method comprising administering a pharmaceutically effective amount of a composition comprising at least one minor cannabinoid alone or in combination with THC, CBD, or both to a subject in need thereof, such that migraine frequency is reduced in the subject. In some embodiments, the subject is a human.

In some embodiments, the subject has chronic migraines. In some embodiments the subject has high frequency migraines.

In some embodiments, the administering is accomplished via injection.

In some embodiments, the treatment is effective within at least 2 hours after administration. In some aspects, the treatment is effective within at least 1 hour after administration, within at least 30 minutes after administration, or within at least 15 minutes after administration.

In some embodiments, the composition comprises THC and CBD, wherein the ratio of CBD:THC is about 30:1 mg/kg to about 300:1 mg/kg.

In some embodiments, the at least one minor cannabinoid is selected from the group consisting of CBG, CBGA, CBN, CBNA, THCV, THCA, CBC, CBCA, CBDV, and D8-THC.

In some embodiments, the at least one minor cannabinoid, the THC (when present), and the CBD (when present) are at least 90 wt % pure. In some preferred embodiments, the at least one minor cannabinoid, the THC (when present), and the CBD (when present) are at least 99 wt % pure.

In some embodiments, at least one biomarker of central and peripheral sensitization is modulated as a result of the administration. In some aspects, the at least one biomarker is selected from the group consisting of NMDA, glutamate, CGRP, FAAH, Substance P, 5-HT, NO, GABA, NGF, serotonin, dopamine, AEA, and 2-AG.

Further provided herein is a method of treating acute migraine pain, the method comprising administering a pharmaceutically effective amount of a composition comprising THC and CBD to a subject in need thereof such that migraine pain is reduced in the subject, while reducing undesired side effects or risk factors of THC. In some embodiments, the subject is a human.

In some embodiments, the subject has chronic migraines. In some embodiments, the subject has high frequency migraines.

In some embodiments, the administering is accomplished via injection.

In some embodiments, the treatment is effective within at least 2 hours after administration. In some aspects, the treatment is effective within at least 1 hour after administration, within at least 30 minutes after administration, or within at least 15 minutes after administration.

In some embodiments, the ratio of CBD:THC is about 30:1 mg/kg to about 300:1 mg/kg.

In some embodiments, the THC and the CBD are at least 90 wt % pure. In some preferred embodiments, the THC and the CBD are at least 99 wt % pure.

In some embodiments, at least one biomarker of central and peripheral sensitization is modulated as a result of the administration. In some aspects, the at least one biomarker is selected from the group consisting of NMDA, glutamate, CGRP, FAAH, Substance P, 5-HT, NO, GABA, NGF, serotonin, dopamine, AEA, and 2-AG.

Further provided herein is a method of treating fibromyalgia pain, the method comprising administering a pharmaceutically effective amount of a composition comprising THC and CBD to a subject in need thereof, such that fibromyalgia pain is reduced in the subject, while reducing undesired side effects or risk factors of THC. In some embodiments, the subject is a human.

In some embodiments, the administering is accomplished via injection.

In some embodiments, the treatment is effective within at least 2 hours after administration. In some aspects, the treatment is effective within at least 1 hour after administration, within at least 30 minutes after administration, or within at least 15 minutes after administration.

In some embodiments, the ratio of CBD:THC is about 30:1 mg/kg to about 300:1 mg/kg.

In some embodiments, the THC and the CBD are at least 90 wt % pure. In some preferred embodiments, the THC and the CBD are at least 99 wt % pure.

In some embodiments, at least one biomarker of central and peripheral sensitization is modulated as a result of the administration. In some aspects, the at least one biomarker is selected from the group consisting of NMDA, glutamate, CGRP, FAAH, Substance P, 5-HT, NO, GABA, NGF, serotonin, dopamine, AEA, and 2-AG.

Further provided herein is a method of alleviating CGRP-induced light aversion, the method comprising administering a composition comprising a pharmaceutically effective amount of at least one minor cannabinoid alone or in combination with THC, CBD, or both to a subject in need thereof.

Further provided herein is a method of alleviating SNP-induced light aversion, the method comprising administering a composition comprising a pharmaceutically effective amount of at least one minor cannabinoid alone or in combination with THC, CBD, or both to a subject in need thereof.

Further provided herein is a method of treating acute migraine pain, photophobia, phonophobia, and/or nausea, the method comprising administering a pharmaceutically effective amount of a composition comprising THC and CBD to a subject in need thereof, such that migraine pain, photophobia, phonophobia, and/or nausea is reduced in the subject. In some embodiments, the subject is a human.

In some embodiments, the administering is accomplished via injection.

In some embodiments, the treatment is effective within at least 2 hours after administration. In some aspects, the treatment is effective within at least 1 hour after administration, within at least 30 minutes after administration, or within at least 15 minutes after administration.

In some embodiments, the migraine pain is measured by a pain scale.

In some embodiments, the photophobia is measured by the Utah Photophobia Symptom Impact Scale, the Korean Photophobia Questionnaire, or by self-reporting from the subject.

In some embodiments, the phonophobia is measured by self-reporting from the subject.

In some embodiments, the nausea is measured by self-reporting from the subject. In some additional embodiments, the nausea is measured by a visual analogue scale.

In some embodiments, the ratio of CBD:THC is about 30:1 mg/kg to about 300:1 mg/kg.

In some embodiments, the composition further comprises at least one minor cannabinoid. In some aspects, the at least one minor cannabinoid is selected from the group consisting of CBG, CBGA, CBN, CBNA, THCV, THCA, CBC, CBCA, CBDV, and D8-THC.

In some embodiments, the THC, the CBD, and the at least one minor cannabinoid (when present) are at least 90 wt % pure. In some preferred embodiments, the THC, the CBD, and the at least one minor cannabinoid (when present) are at least 99 wt % pure.

In some embodiments, at least one biomarker of central and peripheral sensitization is modulated as a result of the administration. In some aspects, the at least one biomarker is selected from the group consisting of NMDA, glutamate, CGRP, FAAH, Substance P, 5-HT, NO, GABA, NGF, serotonin, dopamine, AEA, and 2-AG.

Further provided herein is a method of treating migraine frequency, the method comprising administering a pharmaceutically effective amount of a composition comprising THC and CBD to a subject in need thereof, such that migraine frequency is reduced in the subject. In some embodiments, the subject is a human.

In some embodiments, the subject has chronic migraines. In some embodiments the subject has high frequency migraines.

In some embodiments, the administering is accomplished via injection.

In some embodiments, the treatment is effective within at least 2 hours after administration. In some aspects, the treatment is effective within at least 1 hour after administration, within at least 30 minutes after administration, or within at least 15 minutes after administration.

In some embodiments, the ratio of CBD:THC is about 30:1 mg/kg to about 300:1 mg/kg.

In some embodiments, the composition further comprises at least one minor cannabinoid. In some aspects, the at least one minor cannabinoid is selected from the group consisting of CBG, CBGA, CBN, CBNA, THCV, THCA, CBC, CBCA, CBDV, and D8-THC.

In some embodiments, the THC, the CBD, and the at least one minor cannabinoid (when present) are at least 90 wt % pure. In some preferred embodiments, the THC, the CBD, and the at least one minor cannabinoid (when present) are at least 99 wt % pure.

In some embodiments, at least one biomarker of central and peripheral sensitization is modulated as a result of the administration. In some aspects, the at least one biomarker is selected from the group consisting of NMDA, glutamate, CGRP, FAAH, Substance P, 5-HT, NO, GABA, NGF, serotonin, dopamine, AEA, and 2-AG.

BRIEF DESCRIPTION OF THE FIGURES

FIG. 3A-3B shows the results of the light aversion experiment for all mice tested. FIG. 3C shows the results of the light aversion experiment for female mice. FIG. 3D shows the results of the light aversion experiment for male mice.

FIG. 5A shows the results for all mice tested. FIG. 5B shows the results for female mice. FIG. 5C shows the results for male mice.

FIG. 19A shows the pain behavior 30 minutes after induction of CSD related as compared to baseline. FIG. 19B shows the effect of 100:1 and 30:1 CBD:THC 30 minutes post-induction of CSD as compared to a vehicle.

DETAILED DESCRIPTION

Figure 1A:
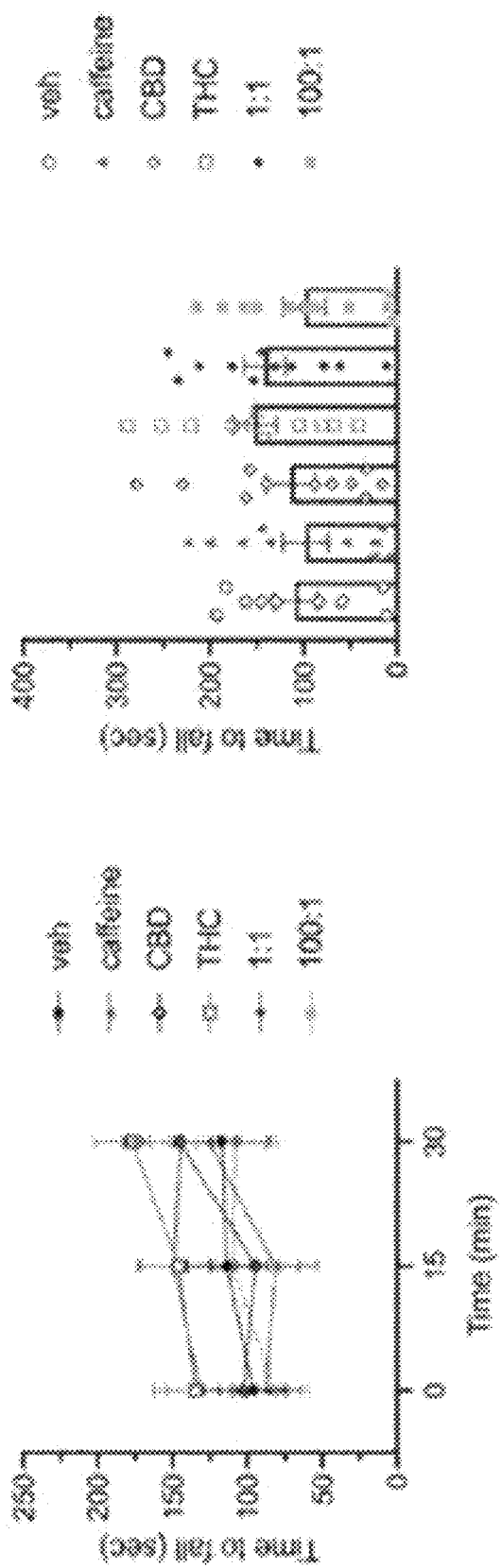
FIGS. 1A-1B show the effect of CBD:THC ratios on motor function using a rotarod assay. The top panel in each figure shows the latency to fall from the rod over 3 consecutive 5 min trials. The bottom panel in each figure shows the average latency to fall from the rod for 3 trials.

Before the present invention is disclosed and described, it is to be understood that this invention is not limited to the particular methods, compositions, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the range or the characteristics being described.

As used herein, the term "about" is used to provide flexibility to a numerical range endpoint by providing that a given value may be "a little above" or "a little below" the endpoint. For example, the endpoint may be within 10%, 8%, 5%, 3%, 2%, or 1% of the listed value. Further, for the sake of convenience and brevity, a numerical range of "about 50 mg/mL to about 80 mg/m L" should also be understood to provide support for the range of "50 mg/mL to 80 mg/mL." The endpoint may also be based on the variability allowed by an appropriate regulatory body, such as the FDA, USP, etc.

In this disclosure, "comprises," "comprising," "containing," and "having" and the like can have the meaning ascribed to them in U.S. Patent Law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open-ended term, like "comprising" or "including," it is understood that direct support should be afforded also to "consisting essentially of" language as well as "consisting of" language as if stated explicitly and vice versa.

The present disclosure details compositions comprising at least one cannabinoid. For instance, in some embodiments, the present disclosure details methods of using compositions comprising at least one minor cannabinoid for pain associated with an attack of migraine with and/or without aura, migraine frequency, and fibromyalgia pain as well as related disorders such as familial hemiplegic migraine, sporadic hemiplegic migraine, and complex regional pain syndrome. In addition, such compositions may be used to alleviate other symptoms associated with migraine, such as photophobia, phonophobia, and nausea.

In additional aspects, the present disclosure details compositions comprising THC and CBD. Specifically, a composition of the disclosure may comprise THC and an amount of CBD to reduce any unwanted side effects of THC or risk factors associated with THC, or to increase efficacy of THC or of the composition. Non-limiting examples of side effects or risk factors include psychoactivity, psychosis, anxiety, paranoia, dizziness, confusion, cardiovascular risk, memory impairment, or combinations thereof. Additionally, the present disclosure details methods of using such compositions for pain associated with an attack of migraine with and/or without aura, migraine frequency, and fibromyalgia pain as well as related disorders such as familial hemiplegic migraine, sporadic hemiplegic migraine, and complex regional pain syndrome.

I. Minor Cannabinoid Compositions

A minor cannabinoid composition of the present disclosure comprises at least one minor cannabinoid. In some embodiments, a composition may further comprise a major cannabinoid, a terpenoid, an additional compound, or a combination thereof.

A minor cannabinoid composition of the present disclosure, when administered to a subject in need thereof, modulates biomarkers of central and peripheral sensitization. As used herein, the term "modulate" as it relates to biomarkers of central and peripheral sensitization generally means a reduction in serum concentration of the biomarkers unless otherwise specified. As used herein, the phrase "peripheral sensitization" refers to hypersensitivity in peripheral nociceptors which cause phenomena such as reduced stimulus threshold (allodynia), increase in response and prolonged after-effects (hyperalgesia), and expansion of the receptive field to non-injured tissue, and hypersensitivity of peripheral ocular and auditory neural pathways which cause phenomena such as photophobia and phonophobia. As used herein, "central sensitization" refers to the hyperexcitable activity of central nociceptive neural pathways and central ocular and auditory pathways which cause phenomena such as photophobia and phonophobia.

A minor cannabinoid composition of the present disclosure may modulate biomarkers of central and peripheral sensitization by binding as an agonist, antagonist, or inverse agonist to one or more receptors from the group consisting of CB1, CB2 (in the dorsal horn, spinal cord), TRPV-1, TRPV-2, TRPV-3, TRPV-4, TRPV-8, TRPA-1, TRPM-8, 5HT-1A, 5HT-2A, Type 3 5HT, alpha-2 adrenoceptor, PPAR-gamma, GAPDH, PPAR, GPCR-92 NK1, EP, trkB, mGlu1, mGlu4, mGlu5 mGlu6, mGlu7, mGlu8, FAAH, NMDA and its subunits NR1 and NR2A.

In some embodiments, a minor cannabinoid composition of the present disclosure may modulate 5-HT receptors (including 5HT-1B/1D receptors), suppress glutamatergic release via CB1 receptor mediated inhibition of NMDA, activate TRPV receptors to modulate CGRP release and influence vasomotor tone, increase AEA levels in cerebrospinal fluid and in the PAG, or decrease CGRP and NO. In preferred embodiments, a minor cannabinoid composition of the present disclosure may modulate biomarkers of central and peripheral sensitization by binding as an agonist, antagonist, or inverse agonist to one or more receptors from the group consisting of CB1, CB2, TRPV1, TRPV2, NMDA and glutamate receptors.

Biomarkers of central and peripheral sensitization may include NMDA, CGRP, FAAH, Substance P, Glutamate, NO, GABA, NGF, serotonin, dopamine, AEA, 2-AG, and others. In some embodiments, biomarkers of peripheral sensitization may include neurogenic CGRP, nitric oxide, or other compounds to inhibit dural blood vessel dilation.

In certain embodiments, a minor cannabinoid composition of the invention may decrease the activity of enzymes that act as biomarkers, such as cyclooxygenase, lipoxygenase and P450-type enzymes such as CYP1A1, CYP1A2, CYP2B6, CYP2C9, CYP3A4, CYP3A5, CYP2A6, CYP2D6, CYP1B1, and/or CYP3A7. Decreasing the activity of one or more of these enzymes may modulate the anti-inflammatory effects that are implicated in migraine pain.

In particular embodiments, a minor cannabinoid composition of the invention may exhibit other forms of antinociception by inhibiting NF-kB activity, iNOS, corticotropin releasing factor binding protein, cysteine protease ATGB4, photoreceptor-specific nuclear receptor NR2E3, or diacylglycerol lipase. In additional particular embodiments, a minor cannabinoid composition of the invention may modulate levels of NMDA, alpha amino-3-hydroxyl-5-methyl-4-isoxazole-proprionate, and kainate receptor modulated neuro-toxicities via CB1, or suppress glutamatergic release by inhibiting modulation of NMDA, mediated by CB1, or increase endo-opioid pre-curser gene expression involved in pain perception. In preferred embodiments, a composition of the present disclosure may affect sensitization by modulating levels of NMDA and/or glutamate.

(a) Minor Cannabinoids

A minor cannabinoid composition of the present disclosure comprises at least one minor cannabinoid. Minor cannabinoids used in the present disclosure may be isolated from natural sources or synthetically manufactured. Non-limiting examples of minor cannabinoids may include CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In one embodiment, a minor cannabinoid composition of the present disclosure may comprise one or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In another embodiment, a minor cannabinoid composition of the present disclosure may comprise two or more, three or more, four or more, five or more, six or more, seven or more, eight or more, nine or more, or ten or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In yet another embodiment, a minor cannabinoid composition of the present disclosure may comprise at least 11, at least 12, at least 13, at least 14, at least 15, at least 16, at least 17, at least 18, at least 19, at least 20, at least 21 or at least 22 or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol.

In some embodiments, the at least one minor cannabinoid is selected from the group consisting of CBG, CBGA, CBN, CBNA, THCV, THCA, CBC, CBCA, CBDV, or D8-THC. In certain embodiments, a minor cannabinoid composition of the present invention comprises at least two, three, four, five, six, seven, eight, nine or ten minor cannabinoid(s) selected from the group consisting of CBG, CBGA, CBN, CBNA, THCV, THCA, CBC, CBCA, CBDV, or D8-THC. In particular embodiments, a minor cannabinoid composition of the invention may comprise any combination of CBG, CBGA, CBN, CBNA, THCV, THCA, CBC, CBCA, CBDV, or D8-THC.

A minor cannabinoid composition of the disclosure may comprise from about 1% to about 100% of one or more minor cannabinoids. For instance, a minor cannabinoid composition may comprise about 5, 10, 15, 20, 25, 30, 35, 40, 45, 50, 55, 60, 65, 70, 75, 80, 85, 90, or 95% of one or more minor cannabinoids. In some embodiments, a minor cannabinoid composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 100% of one or more minor cannabinoids.

(b) Major Cannabinoids

A minor cannabinoid composition of the present disclosure may comprise a major cannabinoid. Non-limiting examples of a major cannabinoid may include cannabinoid D-9THC (THC) and CBD. In one embodiment, a minor cannabinoid composition of the present disclosure comprises THC. In another embodiment, a minor cannabinoid composition of the present disclosure comprises CBD. In a preferred embodiment, a minor cannabinoid composition of the invention may comprise both THC and CBD.

A minor cannabinoid composition of the disclosure may comprise from about 1% to about 99% of one or more major cannabinoids. For instance, a composition may comprise about 5, 10, 15, 20, 25, 30, 35, 40, 45, 50, 55, 60, 65, 70, 75, 80, 85, 90, or 95% of one or more major cannabinoids. In some embodiments, a minor cannabinoid composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of one or more major cannabinoids.

(c) Terpenoids

In certain embodiments, a minor cannabinoid composition of the invention may comprise a terpenoid. Non-limiting examples of terpenoids may include myrcene, 13-caryophyllene, limonene, α-terpineol, linalool, α-phellandrene, α-pinene, β-pinene, γ-terpinene, nerolidol, phytol, caryophyllene oxide and α-humule. In some embodiments, a minor cannabinoid composition of the present disclosure may comprise one, two, three, four, five, or more than five terpenoids selected from the group consisting of myrcene, β-caryophyllene, limonene, α-terpineol, linalool, α-phellandrene, α-pinene, β-pinene, γ-terpinene, nerolidol, phytol, caryophyllene oxide and α-humule.

Generally speaking the at least one terpenoid may comprise from 0% to about 99% of a composition of the present disclosure by weight. For instance, a minor cannabinoid composition may comprise about 5, 10, 15, 20, 25, 30, 35, 40, 45, 50, 55, 60, 65, 70, 75, 80, 85, 90, or 95% of at least one terpenoid by weight. In some embodiments, a minor cannabinoid composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of at least one terpenoid by weight.

(d) Other Compounds

In certain embodiments, a minor cannabinoid composition of the invention may comprise one or more additional compounds. Non-limiting examples of additional compounds may include a simple analgesic like paracetamol and/or acetaminophen, a non-steroidal anti-inflammatory drug (NSAID), a 5-HT (serotonin) receptor agonist, a calcitonin gene related peptide (CGRP) receptor antagonist, an N-methyl D-asparate (NMDA) inhibitor, a glutamate receptor antagonist, a Substance P inhibitor, a GABA inhibitor, FAAH inhibitor, a Nerve Growth Factor (NGF) inhibitor, a Brain-Derived Neurotrophic Factor (BDNF) inhibitor, an extracellular signal-regulated kinase (ERK) antagonist, a NO inhibitor, or another compound. In some embodiments, a minor cannabinoid composition of the present disclosure may comprise one, two, three, four, five, or more than five additional compounds selected from the group consisting of a simple analgesic like paracetamol or acetaminophen, a non-steroidal anti-inflammatory drug (NSAID), a 5-HT (serotonin) receptor agonist, a calcitonin gene related peptide (CGRP) receptor antagonist, an N-methyl D-asparate (NMDA) inhibitor, a glutamate receptor antagonist, a Substance P inhibitor, a GABA inhibitor, FAAH inhibitor, a Nerve Growth Factor (NGF) inhibitor, a Brain-Derived Neurotrophic Factor (BDNF) inhibitor, an extracellular signal-regulated kinase (ERK) antagonist, a NO inhibitor, or another compound.

Generally speaking the at least one additional compound may comprise from 0% to about 99% of a minor cannabinoid composition of the present disclosure by weight. For instance, a minor cannabinoid composition may comprise about 5, 10, 15, 20, 25, 30, 35, 40, 45, 50, 55, 60, 65, 70, 75, 80, 85, 90, or 95% of one or more additional compounds. In some embodiments, a minor cannabinoid composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of one or more additional compounds.

(e) Amounts

Generally speaking, a minor cannabinoid composition of the present disclosure may be used to deliver about 20, 30, 40, 50, 60, 70, 80, 90, 100, 110, 120, 130, 140, 150, 160, 170, 180, or more than 180 mg/day of THC. In certain embodiments, up to 40 mg THC is delivered per day. In other embodiments, up to about 120 mg THC is delivered per day. These amounts may be comprised in a single dose, or more than one dose (e.g. two, three, or more than three doses).

A minor cannabinoid composition of the present disclosure may be used to deliver about 100, 200, 300, 400, 500, 600, 700, 800, 900, 1000, 1100, 1200, 1300, 1400, 1500, 1600, 1700, 1800, 1900, 2000, 2100, 2200, 2300, or 2400 mg/day of CBD. These amounts may be comprised in a single dose, or more than one dose (e.g. two, three, or more than three doses). In particular embodiments, a greater amount of CBD is included in a minor cannabinoid composition to treat the inflammation component in migraine, to counteract psychoactivity or undesired side effects of THC or the minor cannabinoids, or a combination thereof.

In certain embodiments, a minor cannabinoid composition of the present disclosure may be used to deliver about 20, 30, 40, 50, 60, 70, 80, 90, 100, 110, 120, 130, 140, 150, 160, 170, 180, or more than 180 mg/day of THC and about 100, 200, 300, 400, 500, 600, 700, 800, 900, 1000, 1100, 1200, 1300, 1400, 1500, 1600, 1700, 1800, 1900, 2000, 2100, 2200, 2300, or 2400 mg/day of CBD. These amounts may be comprised in a single dose, or more than one dose (e.g. two, three, or more than three doses).

In some embodiments, a minor cannabinoid composition of the present disclosure may be used to deliver about 20, 30, 40, 50, 60, 70, 80, 90, 100, 110, 120, 130, 140, 150, 160, 170, 180, or more than 180 mg/day of a minor cannabinoid. These amounts may be comprised in a single dose, or more than one dose (e.g. two, three, or more than three doses). In each of the embodiments where a composition of the present disclosure comprises a minor cannabinoid, the composition may further by used to deliver about 20, 30, 40, 50, 60, 70, 80, 90, 100, 110, 120, 130, 140, 150, 160, 170, 180, or more than 180 mg/day of THC, or about 100, 200, 300, 400, 500, 600, 700, 800, 900, 1000, 1100, 1200, 1300, 1400, 1500, 1600, 1700, 1800, 1900, 2000, 2100, 2200, 2300, or 2400 mg/day of CBD, or a combination thereof.

In some embodiments, the CBD and THC may be present in the minor cannabinoid composition in a weight ratio (CBD:THC) of about 10:1 to about 300:1. In some aspects, the CBD and THC may be present in a weight ratio of about 10:1 to about 20:1, about 10:1 to about 30:1, about 10:1 to about 40:1, about 10:1 to about 50:1, about 10:1 to about 60:1, about 10:1 to about 70:1, about 10:1 to about 80:1, about 10:1 to about 90:1, about 10:1 to about 100:1, about 10:1 to about 150:1, about 10:1 to about 200:1, about 10:1 to about 250:1, about 10:1 to about 300:1, about 20:1 to about 300:1, about 30:1 to about 300:1, about 40:1 to about 300:1, about 50:1 to about 300:1, about 60:1 to about 300:1, about 70:1 to about 300:1, about 80:1 to about 300:1, about 90:1 to about 300:1, about 100:1 to about 300:1, about 110:1 to about 300:1, about 120:1 to about 300:1, about 130:1 to about 300:1, about 140:1 to about 300:1, about 150:1 to about 300:1, about 20:1 to about 130:1, about 20:1 to about 100:1, or about 30:1 to about 100:1. In some additional aspects, the THC and CBD may be present in a weight ratio of about 10:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 200:1, 250:1, or about 300:1. In some examples, the THC and CBD may be present in a weight ratio of about 20:1, about 25:1, about 30:1, about 100:1, about 130:1, or about 300:1.

In some embodiments, the CBD and THC may be present in the minor cannabinoid composition in a molar ratio (CBD:THC) of about 10:1 to about 300:1. In some aspects, the CBD and THC may be present in a molar ratio of about 10:1 to about 20:1, about 10:1 to about 30:1, about 10:1 to about 40:1, about 10:1 to about 50:1, about 10:1 to about 60:1, about 10:1 to about 70:1, about 10:1 to about 80:1, about 10:1 to about 90:1, about 10:1 to about 100:1, about 10:1 to about 150:1, about 10:1 to about 200:1, about 10:1 to about 250:1, about 10:1 to about 300:1, about 20:1 to about 300:1, about 30:1 to about 300:1, about 40:1 to about 300:1, about 50:1 to about 300:1, about 60:1 to about 300:1, about 70:1 to about 300:1, about 80:1 to about 300:1, about 90:1 to about 300:1, about 100:1 to about 300:1, about 110:1 to about 300:1, about 120:1 to about 300:1, about 130:1 to about 300:1, about 140:1 to about 300:1, about 150:1 to about 300:1, about 20:1 to about 130:1, about 20:1 to about 100:1, or about 30:1 to about 100:1. In some additional aspects, the CBD and THC may be present in a molar ratio of about 10:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 200:1, 250:1, or about 300:1. In some examples, the CBD and THC may be present in a weight ratio of about 20:1, about 25:1, about 30:1, about 100:1, about 130:1, or about 300:1.

II. THC and CBD Compositions

A THC and CBD composition of the present disclosure comprises THC and CBD. Specifically, a THC and CBD composition of the disclosure comprises THC and an amount of CBD to reduce any unwanted side effects of THC or risk factors associated with THC, or increase efficacy of THC or of the composition. Non-limiting examples of side effects or risk factors include psychoactivity, psychosis, anxiety, paranoia, dizziness, confusion, cardiovascular risk, memory impairment, or combinations thereof. In some embodiments, a THC and CBD composition may further comprise at least one minor cannabinoid, a terpenoid, an additional compound, or a combination thereof.

A THC and CBD composition of the present disclosure, when administered to a subject in need thereof, modulates biomarkers and behavioral indicators of central and peripheral sensitization. As used herein, the phrase peripheral sensitization refers to hypersensitivity in peripheral nociceptors which cause phenomena such as reduced stimulus threshold (allodynia), increase in response and prolonged after-effects (hyperalgesia), and expansion of the receptive field to non-injured tissue. As used herein, "central sensitization" refers to the hyperexcitable activity of central nociceptive neural pathways.

A THC and CBD composition of the present disclosure may modulate biomarkers of central and peripheral sensitization by binding as an agonist, antagonist, or inverse agonist to one or more receptors from the group consisting of CB1, CB2 (in the dorsal horn, spinal cord), TRPV-1, TRPV-2, TRPV-3, TRPV-4, TRPV-8, TRPA-1, TRPM-8, 5HT-1A, 5HT-2A, Type 3 5HT, alpha-2 adrenoceptor, PPAR-gamma, GAPDH, PPAR, GPCR-92 NK1, EP, trkB, mGlu1, mGlu4, mGlu5 mGlu6, mGlu7, mGlu8, FAAH, NMDA and its subunits NR1 and NR2A.

In some embodiments, a THC and CBD composition of the present disclosure may indirectly modulate 5-HT receptors (including 5HT-1B/1D receptors), suppress glutamatergic release via CB1 receptor mediated inhibition of NMDA, activate TRPV receptors to modulate CGRP release and influence vasomotor tone, increase AEA levels in cerebrospinal fluid and in the PAG, or decrease CGRP and NO. In preferred embodiments, a composition of the present disclosure may modulate biomarkers of central and peripheral sensitization by binding as an agonist, antagonist, or inverse agonist to one or more receptors from the group consisting of CB1, CB2, TRPV1, TRPV2, NMDA and glutamate receptors.

Biomarkers of central and peripheral sensitization may include NMDA, CGRP, FAAH, Substance P, Glutamate, NO, GABA, NGF, serotonin, dopamine, NO, AEA, 2-AG, and others. In some embodiments, biomarkers of peripheral sensitization may include neurogenic CGRP, nitric oxide, or other compounds to inhibit dural blood vessel dilation.

In certain embodiments, a THC and CBD composition of the invention may decrease the activity of enzymes that act as biomarkers, such as cyclooxygenase, lipoxygenase and P450-type enzymes such as CYP1A1, CYP1A2, CYP2B6, CYP2C9, CYP3A4, CYP3A5, CYP2A6, CYP2D6, CYP1B1, and/or CYP3A7. Decreasing the activity of one or more of these enzymes may modulate the anti-inflammatory effects that are implicated in migraine pain.

In particular embodiments, a THC and CBD composition of the invention may exhibit other forms of anti-nociception by inhibiting NF-kB activity, iNOS, corticotropin releasing factor binding protein, cysteine protease ATGB4, photoreceptor-specific nuclear receptor NR2E3, or diacylglycerol lipase. In additional particular embodiments, a THC and CBD composition of the invention may modulate levels of NMDA, alpha amino-3-hydroxyl-5-methyl-4-isoxazole-proprionate, and kainate receptor modulated neuro-toxicities via CB1, or suppress glutamatergic release by inhibiting modulation of NMDA, mediated by CB1, or increase endoopioid pre-curser gene expression involved in pain perception. In preferred embodiments, a THC and CBD composition of the present disclosure may affect sensitization by modulating levels of NMDA and/or glutamate.

Behavioral indicators may include behavioral responses in animal or human models of trigeminovascular nociception, animal models of spontaneous nociceptive responses in the craniofacial region or plantar region, models of associated neurological symptoms, models of associated symptoms of migraine or sensitization such as photophobia, phonophobia, osmophobia, allodynia, or other symptoms, or other animal or human models.

(a) THC and CBD

A THC and CBD composition of the present disclosure comprises THC (cannabinoid D-9THC) and CBD. Specifically, a composition of the disclosure comprises THC and an amount of CBD to reduce any unwanted side effects of THC or risk factors associated with THC, or increase efficacy of THC. Non-limiting examples of side effects or risk factors include psychoactivity, psychosis, anxiety, paranoia, dizziness, confusion, increased cardiovascular risk, memory impairment, or combinations thereof.

As used herein, THC refers to tetrahydrocannabinol, whether synthetically produced or isolated from a plant. THC may refer to (−)-trans-$\Delta^9$-tetrahydrocannabinol or isomers thereof. As used herein, CBD refers to cannabidiol or isomers thereof, whether synthetically produced or isolated from a plant.

For instance, a THC and CBD composition of the present disclosure may comprise from about 0.1% to about 99% of THC. For instance, a THC and CBD composition may comprise about 5, 10, 15, 20, 25, 30, 35, 40, 45, 50, 55, 60, 65, 70, 75, 80, 85, 90, or 95% of THC. In some embodiments, a THC and CBD composition may comprise about 0.1 to about 0.5, about 0.5 to about 1, about 1 to about 2, about 2 to about 5, about 5 to about 10, about 5 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of THC.

In each of the above embodiments, a THC and CBD composition of the disclosure further comprises CBD. For instance, a THC and CBD composition of the disclosure may comprise from about 1% to about 99.9% of CBD. For instance, a composition may comprise about 5, 10, 15, 20, 25, 30, 35, 40, 45, 50, 55, 60, 65, 70, 75, 80, 85, 90, 95, 98, 98.5, 99, 99.5, 99.7, or 99.9% of CBD. In some embodiments, a THC and CBD composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, about 80 to about 95, about 95 to about 98, about 98 to about 99.9% of CBD.

In certain embodiments, a THC and CBD composition of the present disclosure comprises about 80% CBD to about 99.9% CBD, and about 0.1% THC to about 20% THC. In particular embodiments, a THC and CBD composition of the present disclosure comprises about 90% CBD to about 97% CBD and about 3% THC to about 10% THC. In preferred embodiments, a THC and CBD composition may comprise at least about 90% CBD and no more than about 10% THC. For instance, a THC and CBD composition may comprise at least about 90, 91, 92, 93, 94, 95, 96, 97, or 98% CBD and no more than about 10, 9, 8, 7, 6, 5, 4, 3, or 2% THC. In other preferred embodiments, a THC and CBD composition may comprise at least about 95% CBD and no more than about 5% THC. For instance, a THC and CBD composition may comprise at least about 95, 96, 97, 98.5, 99, 99.5, or 99.9% CBD and no more than about 5, 4, 3, 2, 1.5, 1, 0.5, or 0.1% THC.

In some embodiments, the CBD and THC may be present in the composition in a weight ratio (CBD:THC) of about 10:1 to about 300:1. In some aspects, the CBD and THC may be present in a weight ratio of about 10:1 to about 20:1, about 10:1 to about 30:1, about 10:1 to about 40:1, about 10:1 to about 50:1, about 10:1 to about 60:1, about 10:1 to about 70:1, about 10:1 to about 80:1, about 10:1 to about 90:1, about 10:1 to about 100:1, about 10:1 to about 150:1, about 10:1 to about 200:1, about 10:1 to about 250:1, about 10:1 to about 300:1, about 20:1 to about 300:1, about 30:1 to about 300:1, about 40:1 to about 300:1, about 50:1 to about 300:1, about 60:1 to about 300:1, about 70:1 to about 300:1, about 80:1 to about 300:1, about 90:1 to about 300:1, about 100:1 to about 300:1, about 110:1 to about 300:1, about 120:1 to about 300:1, about 130:1 to about 300:1, about 140:1 to about 300:1, about 150:1 to about 300:1, about 20:1 to about 130:1, about 20:1 to about 100:1, or about 30:1 to about 100:1. In some additional aspects, the CBD and THC may be present in a weight ratio of about 10:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 200:1, 250:1, or about 300:1. In some examples, the CBD and THC may be present in a weight ratio of about 20:1, about 25:1, about 30:1, about 100:1, about 130:1, or about 300:1.

In some embodiments, the CBD and THC may be present in the composition in a molar ratio (CBD:THC) of about 10:1 to about 300:1. In some aspects, the CBD and THC may be present in a molar ratio of about 10:1 to about 20:1, about 10:1 to about 30:1, about 10:1 to about 40:1, about 10:1 to about 50:1, about 10:1 to about 60:1, about 10:1 to about 70:1, about 10:1 to about 80:1, about 10:1 to about 90:1, about 10:1 to about 100:1, about 10:1 to about 150:1, about 10:1 to about 200:1, about 10:1 to about 250:1, about 10:1 to about 300:1, about 20:1 to about 300:1, about 30:1 to about 300:1, about 40:1 to about 300:1, about 50:1 to about 300:1, about 60:1 to about 300:1, about 70:1 to about 300:1, about 80:1 to about 300:1, about 90:1 to about 300:1, about 100:1 to about 300:1, about 110:1 to about 300:1, about 120:1 to about 300:1, about 130:1 to about 300:1, about 140:1 to about 300:1, about 150:1 to about 300:1, about 20:1 to about 130:1, about 20:1 to about 100:1, or about 30:1 to about 100:1. In some additional aspects, the CBD and THC may be present in a molar ratio of about 10:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 200:1, 250:1, or about 300:1. In some examples, the CBD and THC may be present in a weight ratio of about 20:1, about 25:1, about 30:1, about 100:1, about 130:1, or about 300:1.

CBD in a composition of the disclosure may reduce the psychoactive side effects or risk factors of THC or other cannabinoids as measured by levels of prolactin, c-Fox expression, anandamide (AEA) in serum and/or cerebral spinal fluid (CSF), GABA, glutamate, FAAH, ethanolamide (palmitoylethanolamide and oleoylethanolamide), FLAT (FAAH-like anandamide transporter), or other fatty acid binding proteins (FABPs).

CBD may exert its antipsychotic effects as measured by acting as an antagonist, agonist, or inverse agonist to receptors CB1, CB2, and TRPV1 in the prefrontal cortex, amygdala and/or hippocampus, GABAergic neurons in the nucleus accumbens, 5HT-1A, D2, PPARγ (peroxisome proliferator activated receptor gamma), or by interacting with ion channels or enzymes, as described herein, contributing to its anti-inflammatory, anti-oxidative, and/or neuroprotective properties.

CBD's anti-psychotic effects may be measured in the striatum and temporal cortex, ventral tegmental area (VTA), nucleus accumbens, ventral pallidum, mediodorsal thalamic nucleus, prefrontal cortex, anterior cingulate, parahippocampal gyrus, amygdala, right posterior temporal gyrus and right temporal lobe, middle occipital gyrus, cerebellum, left caudate, or dopaminergic mesolimbic pathway.

CBD's anti-psychotic effects may be measured by reduction of psychotomimetic symptoms, amorphine-induced stereotyped behavior, amphetamine, D-amphetamine, and ketamine induced hyperlocomotion, social withdrawal in animal models, reduced scores of Brief Psychiatric Rating Scale (BPRS), Parkinson Psychosis Questionnaire, Positive and Negative Syndrome Scale (PANSS), various other behavioral and neurochemical techniques in animal models, such as apomorphine stereotypy, catalepsy, MK-801 Pre-pulse inhibition (PPI), hyperlocomotion, or social withdrawal, c-Fos immunohistochemistry, or other techniques.

Methods of isolating, synthesizing, or purifying THC and CBD are known in the art.

(b) Minor Cannabinoids

A THC and CBD composition of the present disclosure may further comprise at least one minor cannabinoid. Minor cannabinoids used in the present disclosure may be isolated from natural sources or synthetically manufactured. Non-limiting examples of minor cannabinoids may include CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In one embodiment, a THC and CBD composition of the present disclosure may comprise one or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In another embodiment, a THC and CBD composition of the present disclosure may comprise two or more, three or more, four or more, five or more, six or more, seven or more, eight or more, nine or more, or ten or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In yet another embodiment, a THC and CBD composition of the present disclosure may comprise at least 11, at least 12, at least 13, at least 14, at least 15, at least 16, at least 17, at least 18, at least 19, at least 20, at least 21 or at least 22 or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol.

In some embodiments, a minor cannabinoid may be selected from the group consisting of CBG, CBGA, CBN, CBNA, THCV, THCA, CBC, CBCA, CBDV, or D8-THC. In certain embodiments, a THC and CBD composition of the present invention may comprise at least two, three, four, five, six, seven, eight, nine or ten minor cannabinoid(s) selected from the group consisting of CBG, CBGA, CBN, CBNA, THCV, THCA, CBC, CBCA, CBDV, or D8-THC. In particular embodiments, a THC and CBD composition of the invention may comprise any combination of CBG, CBGA, CBN, CBNA, THCV, THCA, CBC, CBCA, CBDV, or D8-THC.

A THC and CBD composition of the disclosure may comprise from about 1% to about 99.9% of one or more minor cannabinoids. For instance, a THC and CBD composition may comprise about 0.1, 0.5, 1.5, 2, 2.5, 3, 4, 5, 10, 15, 20, 25, 30, 35, 40, 45, 50, 55, 60, 65, 70, 75, 80, 85, 90, 95, 96, 97, 98, 99, 99.5, 99.7, 99.9% of one or more minor cannabinoids. In some embodiments, a THC and CBD composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of one or more minor cannabinoids.

In some embodiments, a THC and CBD composition may comprise a ratio of minor cannabinoid to THC of about 5:1, 8:1, 10:1, 12:1, 15:1, 18:1, 20:1, 22:1, 25:1, 28:1, 30:1, 32:1, 35:1, 38:1, 40:1, 50:1, 75:1, 90:1, 100:1, 110:1, 125:1, 150:1, 200:1, 250:1, 400:1, or 500:1. In other embodiments, a THC and CBD composition may comprise a ratio of minor cannabinoid to D8-THC of about 5:1, 8:1, 10:1, 12:1, 15:1, 18:1, 20:1, 22:1, 25:1, 28:1, 30:1, 32:1, 35:1, 38:1, 40:1, 50:1, 75:1, 90:1, 100:1, 110:1, 125:1, 150:1, 200:1, 250:1, 400:1, or 500:1. In still other embodiments a THC and CBD composition may comprise a ratio of minor cannabinoid to THCV of about 5:1, 8:1, 10:1, 12:1, 15:1, 18:1, 20:1, 22:1, 25:1, 28:1, 30:1, 32:1, 35:1, 38:1, 40:1, 50:1, 75:1, 90:1, 100:1, 110:1, 125:1, 150:1, 200:1, 250:1, 400:1, or 500:1. In preferred embodiments, a THC and CBD composition may comprise a ratio of CBC, CBL, CBN, CBG, CBDV, CBC to THC, D8-THC, or THCV of about 5:1, 8:1, 10:1, 12:1, 15:1, 18:1, 20:1, 22:1, 25:1, 28:1, 30:1, 32:1, 35:1, 38:1, 40:1 50:1, 75:1, 90:1, 100:1, 110:1, 125:1, 150:1, 200:1, 250:1, 400:1, or 500:1.

In particular embodiments, a THC and CBD composition may comprise a ratio of D8-THC to D9-THC of about 1:1, 2:1, 3:1, 4:1, 5:1, 6:1, 7:1, 8:1, 9:1, or 10:1. In other embodiments, a THC and CBD composition may comprise a ratio of THCV to D9-THC of about 1:1, 2:1, 3:1, 4:1, 5:1 6:1, 7:1, 8:1, 9:1, or 10:1.

(c) Terpenoids

In certain embodiments, a THC and CBD composition of the invention may comprise a terpenoid. Non-limiting examples of terpenoids may include myrcene, β-caryophyllene, limonene, α-terpineol, linalool, α-phellandrene, α-pinene, β-pinene, γ-terpinene, nerolidol, phytol, caryophyllene oxide and α-humule. In some embodiments, a THC and CBD composition of the present disclosure may comprise one, two, three, four, five, or more than five terpenoids selected from the group consisting of myrcene, β-caryophyllene, limonene, α-terpineol, linalool, α-phellandrene, α-pinene, β-pinene, γ-terpinene, nerolidol, phytol, caryophyllene oxide and α-humule.

Generally speaking the at least one terpenoid may comprise from 0% to about 99.9% of a THC and CBD composition of the present disclosure by weight. For instance, a THC and CBD composition may comprise about 5, 10, 15, 20, 25, 30, 35, 40, 45, 50, 55, 60, 65, 70, 75, 80, 85, 90, 95, 97, 98, 99, 99.5, or 99.9% of at least one terpenoid by weight. In some embodiments, a THC and CBD composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 90, about 90 to 95, about 95 to 99.9% of at least one terpenoid by weight.

(d) Other Compounds

In certain embodiments, a THC and CBD composition of the invention may comprise one or more additional compounds. Non-limiting examples of additional compounds may include a simple analgesic like paracetamol and/or acetaminophen, a non-steroidal anti-inflammatory drug (NSAID), a 5-HT (serotonin) receptor agonist, a calcitonin gene related peptide (CGRP) receptor antagonist, an N-methyl D-asparate (NMDA) inhibitor, a glutamate receptor antagonist, a Substance P inhibitor, a GABA inhibitor, FAAH inhibitor, a Nerve Growth Factor (NGF) inhibitor, a Brain-Derived Neurotrophic Factor (BDNF) inhibitor, an extracellular signal-regulated kinase (ERK) antagonist, a NO inhibitor, or another compound. In some embodiments, a THC and CBD composition of the present disclosure may comprise one, two, three, four, five, or more than five additional compounds selected from the group consisting of a simple analgesic like paracetamol or acetaminophen, a non-steroidal anti-inflammatory drug (NSAID), a 5-HT (serotonin) receptor agonist, a calcitonin gene related peptide (CGRP) receptor antagonist, an N-methyl D-asparate (NMDA) inhibitor, a glutamate receptor antagonist, a Substance P inhibitor, a GABA inhibitor, FAAH inhibitor, a Nerve Growth Factor (NGF) inhibitor, a Brain-Derived Neurotrophic Factor (BDNF) inhibitor, an extracellular signal-regulated kinase (ERK) antagonist, a NO inhibitor, or another compound.

Generally speaking the at least one additional compound may comprise from 0% to about 99% of a THC and CBD composition of the present disclosure by weight. For instance, a composition may comprise about 5, 10, 15, 20, 25, 30, 35, 40, 45, 50, 55, 60, 65, 70, 75, or 80% of one or more additional compounds. In some embodiments, a THC and CBD composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, or about 60 to about 80, about 65 to about 85, about 70 to about 90, about 75 to about 95, or about 80 to about 99% of one or more additional compounds.

(e) Amounts

Generally speaking, a THC and CBD composition of the present disclosure may be used to deliver about 20, 30, 40, 50, 60, 70, 80, 90, 100, 110, 120, 130, 140, 150, 160, 170, 180, or more than 180 mg/day of THC. These amounts may be comprised in a single dose, or more than one dose (e.g. two, three, or more than three doses).

In each of the above embodiments, a THC and CBD composition of the present disclosure may further be used to deliver about 100, 200, 300, 400, 500, 600, 700, 800, 900, 1000, 1100, 1200, 1300, 1400, 1500, 1600, 1700, 1800, 1900, 2000, 2100, 2200, 2300, or 2400 mg/day of CBD. These amounts may be comprised in a single dose, or more than one dose (e.g. two, three, or more than three doses). In particular embodiments, a greater amount of CBD is included in the composition to reduce undesired side effects of THC or risk factors associated with THC, or increase efficacy of THC. Non-limiting examples of side effects or risk factors include psychoactivity, psychosis, anxiety, paranoia, dizziness, confusion, cardiovascular risk, memory impairment, or combinations thereof.

III. Pharmaceutical Compositions

The present disclosure also provides pharmaceutical compositions. A pharmaceutical composition comprises a minor cannabinoid composition (as detailed in section I above) or a THC and CBD composition (as detailed in section II above) and at least one pharmaceutically acceptable excipient. A pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In each of the embodiments described herein, a composition of the invention may optionally comprise one or more additional compounds. Thus, in addition to the therapies described herein, one may also provide to the subject other therapies known to be efficacious for treatment of the disease, disorder, or condition or to reduce side effects. In some embodiments, the additional drug or therapeutically active agent induces anti-inflammatory effects.

(i) Diluent

In one embodiment, the excipient may be a diluent. The diluent may be compressible (i.e., plastically deformable) or abrasively brittle. Non-limiting examples of suitable compressible diluents may include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders may include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers may include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents may include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives may include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials may include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a mammal including, but not limited to, a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

IV. Administration (a) Dosage Forms

A composition of the present disclosure may be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pennsylvania (18th ed, 1995), and Liberman, H. A. and Lachman, L., Eds., Pharmaceutical Dosage Forms, Marcel Dekker Inc., New York, New York (1980). In a specific embodiment, a composition may be a food supplement or a composition may be a cosmetic.

Solid dosage forms for oral administration may include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In particular embodiments, the composition may be formulated for sublingual delivery. Sublingual delivery forms (films, tablets, or sprays) are designed to dissolve very rapidly. Examples of such formulations may include ergotamine tartrate, isosorbide dinitrate, isoproterenol HCl, or a combination thereof. The necessary ingredients for the pharmaceutical dosage unit may be processed in accordance with known methods, using or incorporating familiar coatings and additives as required. By way of example only, in addition to the pharmaceutically active components, a dosage unit may contain effective amounts of binders, fillers, disintegrants, sustained-release agents, diluents, anti-adherents, glidants, flow aids, plasticizers and lubricants, which are well known in the field of pharmaceutical processing for sublingual delivery. For instance, the formulation of these tablets may contain, in addition to the active agents, a limited number of soluble excipients, including a binder such as povidone or hydroxypropyl methylcellulose (HPMC), diluents such as lactose, mannitol, starch or cellulose, a disintegrant such as pregelatinized or modified starch, lubricants such as magnesium stearate, stearic acid or hydrogenated vegetable oil, a sweetener such as saccharin or sucrose and suitable flavoring and coloring agents. The process of making sublingual dosage forms may involve, for instance, moistening the blended powder components with an alcohol-water solvent system containing approximately 60% alcohol and 40% water and pressing this mixture into tablets.

In certain embodiments, a composition of the present disclosure may be encapsulated in a suitable vehicle to either aid in the delivery of the compound30(s) to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a composition of the present disclosure may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of active ingredient (e.g. minor cannabinoid, major cannabinoid, terpenoid, combination thereof, etc.), concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions.

In yet another embodiment, a composition of the present disclosure may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

Generally, a safe and effective amount of a composition of the present disclosure is an amount that would cause the desired therapeutic effect in a subject while minimizing undesired side effects. In various embodiments, an effective amount of a composition of the present disclosure may reduce pain associated with an attack of migraine with and/or without aura, may reduce migraine frequency, may reduce fibromyalgia pain, or pain associated with related disorders such as familial hemiplegic migraine, sporadic hemiplegic migraine, and complex regional pain syndrome.

The amount of a composition described herein that can be combined with a pharmaceutically acceptable carrier to produce a single dosage form will vary depending upon the subject treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a composition of the present disclosure can occur as a single event or over a time course of treatment. For example, a composition of the present disclosure may be administered daily, weekly, bi-weekly, or monthly. For treatment of acute conditions, the time course of treatment may be from at least one day to at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities.

(b) Purity

Generally speaking, a compound included in a composition of the disclosure, such as a minor cannabinoid or a major cannabinoid should be of high purity and consistent quality, regardless of source. For instance, a minor or major cannabinoid used in a composition of the disclosure is at least 90, 91, 92, 93, 94, 95, 96, 97, 98 or 99 wt % pure. In certain embodiments, a minor or major cannabinoid used in a composition of the disclosure is at least 95, 96, 97, 98, or 99 wt % pure. In preferred embodiments, a minor or major cannabinoid used in a composition of the disclosure is at least 97 wt % pure. In more preferred embodiments, a minor or major cannabinoid used in a composition of the disclosure is at least 99 wt % pure. Unless otherwise specified, percent purity is based on weight.

Additionally, THC and/or CBD included in a composition of the present disclosure should be of high purity and consistent quality, regardless of source. For instance, THC and/or CBD used in a composition of the disclosure is at least 90, 91, 92, 93, 94, 95, 96, 97, 98 or 99 wt % pure. In certain embodiments, THC and/or CBD used in a composition of the disclosure is at least 95, 96, 97, 98, or 99 wt % pure. In preferred embodiments, THC and/or CBD used in a composition of the disclosure is at least 97 wt % pure. In more preferred embodiments, THC and/or CBD used in a composition of the disclosure is at least 99 wt % pure.

Manufacture of a compound for a composition of the disclosure is preferred to meet GLP requirements. In certain embodiments, manufacture of a compound for a composition of the disclosure meets GMP requirements to ensure consistent quality.

Quantitative/qualitative methods to confirm quality and purity include use of High Performance Liquid Chromatography (HPLC), Ultra Performance Liquid Chromatography (UPLC), Nuclear Magnetic Resonance (NMR) spectroscopy, Gas Chromatography (GC), Thin Layer Chromatography (TLC), and standard methods for testing for contamination of microbiological, heavy metal, pesticide, or other contaminants.

Generally speaking a composition of the present disclosure has at least 5%, 10%, 15%, 20%, 25%, 30%, 40%, 50%, 60%, 70%, 80%, 90%, or 95% fewer side effects than if the minor and major cannabinoids are not at least 90% pure. Side effects, as used herein, refer to any effects of the present composition other than reducing pain, photophobia, phonophobia, or nausea associated with an attack of migraine with and/or without aura, migraine frequency, and fibromyalgia pain as well as related disorders such as familial hemiplegic migraine, sporadic hemiplegic migraine, and complex regional pain syndrome.

V. Methods

Another aspect of the present disclosure is methods of using the compositions described in the above sections.

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

(a) Methods of Reducing Migraine Pain with a Minor Cannabinoid Composition

A minor cannabinoid composition of the present disclosure may be used in a method of reducing migraine pain. Generally speaking, such a method would comprise administering a pharmaceutically effective amount of at least one minor cannabinoid alone, or in combination with THC, CBD, or both, such that and migraine pain is reduced in the subject. In some embodiments, at least one biomarker of central and peripheral sensitization may be modulated as a result of the administration.

In some embodiments, the at least one minor cannabinoid, detailed in section I above, may be a phytocannabinoid. As used herein, the term "phytocannabinoid" refers to a cannabinoid isolated from a non-synthetic source.

In certain embodiments, the migraine pain is acute migraine pain. Generally speaking, a method of the invention is used fora subject suffering from an acute migraine. Methods of diagnosing acute migraine are known in the art.

In some embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

(b) Methods of Reducing Migraine Pain with a THC and CBD Composition

A THC and CBD composition of the present disclosure may be used in a method of reducing migraine pain while reducing unwanted side effects of THC or risk factors associated with THC. Non-limiting examples of side effects or risk factors include psychoactivity, psychosis, anxiety, paranoia, dizziness, confusion, increased heart rate, memory impairment, or combinations thereof. Generally speaking, such a method would comprise administering a pharmaceutically effective amount of THC and CBD, such that migraine pain is reduced in the subject, while unwanted side effects or risk factors of THC are minimized. In some embodiments, at least one biomarker of central and peripheral sensitization may be modulated as a result of the administration.

In certain embodiments, the migraine pain is acute migraine pain. Generally speaking, a method of the invention is used fora subject suffering from an acute migraine. Methods of diagnosing acute migraine are known in the art.

In some embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

(c) Reducing Migraine Frequency with a Minor Cannabinoid Composition

A minor cannabinoid composition of the present disclosure may be used in a method of reducing migraine frequency. Generally speaking, such a method would comprise administering a pharmaceutically effective amount of at least one minor cannabinoid alone, or in combination with THC, CBD, or both, such that migraine frequency is reduced in the subject. In some embodiments, at least one biomarker of central and peripheral sensitization may be modulated as a result of the administration.

In some embodiments, the at least one minor cannabinoid, detailed in section I above, may be a phytocannabinoid. In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with chronic migraine or high frequency migraine. As used here, chronic migraine is defined as over 15 headache days per month. High frequency migraine is defined as 7-14 headache days per month. Methods of diagnosing chronic migraine or high frequency migraine are known in the art.

(d) Methods of Reducing Migraine Frequency with a THC and CBD Composition

A THC and CBD composition of the present disclosure may be used in a method of reducing migraine frequency. Generally speaking, such a method would comprise administering a pharmaceutically effective amount of THC and CBD, such that migraine frequency is reduced in the subject, while unwanted side effects or risk factors of THC are minimized. In some embodiments, at least one biomarker of central and peripheral sensitization may be modulated as a result of the administration.

In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with chronic migraine or high frequency migraine. As used here, chronic migraine is defined as over 15 headache days per month. High frequency migraine is defined as 7-14 headache days per month. Methods of diagnosing chronic migraine or high frequency migraine are known in the art.

(e) Methods of Reducing Fibromyalgia Pain with a Minor Cannabinoid Composition

A minor cannabinoid composition of the present disclosure may be used in a method of reducing fibromyalgia pain. Generally speaking, such a method would comprise administering a pharmaceutically effective amount of at least one minor cannabinoid alone, or in combination with THC, CBD, or both, such that fibromyalgia pain is reduced in the subject. In some embodiments, at least one biomarker of central and peripheral sensitization may be modulated as a result of the administration.

In some embodiments, the at least one minor cannabinoid, detailed in section I above, may be a phytocannabinoid. In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with fibromyalgia pain. Methods of diagnosing fibromyalgia pain are known in the art.

(f) Methods of Reducing Fibromyalgia Pain with THC and CBD Compositions

A THC and CBD composition of the present disclosure may be used in a method of reducing fibromyalgia pain. Generally speaking, such a method would comprise administering a pharmaceutically effective amount of THC and CBD, such that fibromyalgia pain is reduced in the subject, while unwanted side effects or risk factors of THC are minimized. In some embodiments, at least one biomarker of central and peripheral sensitization may be modulated as a result of the administration.

In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with fibromyalgia pain. Methods of diagnosing and measuring fibromyalgia pain are known in the art, and may include pain scales and self-reporting by the subject.

(g) Methods of Treating Acute Migraine Pain, Photophobia, Phonophobia, and/or Nausea A minor cannabinoid composition of the present disclosure may be used in a method of treating acute migraine pain, photophobia, phonophobia, and/or nausea. Generally speaking, such a method would comprise administering a pharmaceutically effective amount of at least one minor cannabinoid alone or in combination with THC, CBD, or both, to a subject in need thereof such that migraine pain, photophobia, phonophobia, and/or nausea is reduced in the subject. In some embodiments, at least one biomarker of central and peripheral sensitization may be modulated as a result of the administration.

In some embodiments, the at least one minor cannabinoid, detailed in section I above, may be a phytocannabinoid. As used herein, the term "phytocannabinoid" refers to a cannabinoid isolated from a non-synthetic source.

In certain embodiments, the migraine pain is acute migraine pain. Generally speaking, a method of the invention is used for a subject suffering from an acute migraine. Methods of diagnosing acute migraine are known in the art.

Methods of measuring migraine pain are generally known in the art, and may include the use of pain scales. For example, the pain scales may include Numerical Rating Scales (NRS) or Visual Analogue Scales (VAS) (e.g., Likert or Wong-Baker). In some embodiments, pain may be self-reported by the subject on a pain scale from 0-10, with 0 indicating no pain and 10 indicating high levels of pain. In some embodiments, a four-point scale from 0-3 may be used, wherein 0 indicates no pain and 3 indicates high levels of pain, wherein the subject self-reports the level of their pain. Migraine pain may be reported prior to the administration, wherein pain on a scale of 2 or 3 indicates treatment is needed. After administration, the pain may be improved to a scale of 1 or 0 within at least 2 hours of administration. In some examples, the pain may be improved within at least 2 hours of administration, within at least 1.5 hours of administration, within at least 1 hour of administration, within at least 30 minutes of administration, or within at least 15 minutes of administration. In preferred embodiments, the migraine pain is improved to 0 within at least 2 hours of administration.

Methods of measuring photophobia are generally known in the art, and may include the Utah Photophobia Symptom Impact Scale and the Korean Photophobia Questionnaire. In some embodiments, photophobia may be self-reported by a subject on a pain scale. Photophobia may be reported by a subject prior to the administration. After administration, a reduction in photophobia may be self-reported by the subject. In other embodiments, the reduction in photophobia may be determined by the methods described above.

Methods of measuring nausea are generally known in the art, and may include self-reporting by the subject or may include a visual analogue scale.

In some embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

(h) Methods of Treating Migraine Pain with a THC and CBD Composition

A THC and CBD composition of the present disclosure may be used in a method of treating migraine pain while reducing unwanted side effects of THC or risk factors associated with THC. Non-limiting examples of side effects or risk factors include psychoactivity, psychosis, anxiety, paranoia, dizziness, confusion, increased heart rate, memory impairment, or combinations thereof. Generally speaking, such a method would comprise administering a pharmaceutically effective amount of THC and CBD, such that migraine pain is reduced in the subject, while unwanted side effects or risk factors of THC are minimized. In some embodiments, at least one biomarker of central and peripheral sensitization may be modulated as a result of the administration.

In certain embodiments, the migraine pain is acute migraine pain. Generally speaking, a method of the invention is used for a subject suffering from an acute migraine. Methods of diagnosing acute migraine are known in the art.

In some embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

(i) Treating Migraine Frequency with a Minor Cannabinoid Composition

A minor cannabinoid composition of the present disclosure may be used in a method of treating migraine frequency. Generally speaking, such a method would comprise administering a pharmaceutically effective amount of at least one minor cannabinoid alone, or in combination with THC, CBD, or both, migraine frequency is reduced in the subject. In some embodiments, at least one biomarker of central and peripheral sensitization may be modulated as a result of the administration.

In some embodiments, the at least one minor cannabinoid, detailed in section I above, may be a phytocannabinoid. In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with chronic migraine or high frequency migraine. As used here, chronic migraine is defined as over 15 headache days per month. High frequency migraine is defined as 7-14 headache days per month. Methods of diagnosing chronic migraine or high frequency migraine are known in the art.

(j) Methods of Treating Fibromyalgia Pain with a Minor Cannabinoid Composition

A minor cannabinoid composition of the present disclosure may be used in a method of treating fibromyalgia pain. Generally speaking, such a method would comprise administering a pharmaceutically effective amount of at least one minor cannabinoid alone, or in combination with THC, CBD, or both, such that fibromyalgia pain is reduced in the subject. In some embodiments, at least one biomarker of central and peripheral sensitization may be modulated as a result of the administration.

In some embodiments, the at least one minor cannabinoid, detailed in section I above, may be a phytocannabinoid. In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with fibromyalgia pain. Methods of diagnosing and measuring fibromyalgia pain are known in the art, and may include pain scales and self-reporting by the subject.

(k) Methods of Treating Fibromyalgia Pain with THC and CBD Compositions

A THC and CBD composition of the present disclosure may be used in a method of treating fibromyalgia pain. Generally speaking, such a method would comprise administering a pharmaceutically effective amount of THC and CBD, such that fibromyalgia pain is reduced in the subject, while unwanted side effects or risk factors of THC are minimized. In some embodiments, at least one biomarker of central and peripheral sensitization may be modulated as a result of the administration.

In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with fibromyalgia pain. Methods of diagnosing and measuring fibromyalgia pain are known in the art, and may include pain scales and self-reporting by the subject.

EXAMPLES

Example 1: Preclinical Model

The biomarkers and other indicators of activity of the present disclosure, which includes central and peripheral sensitization, may be observed using pre-clinical in vitro and in vivo models of migraine pain and frequency, fibromyalgia pain, and other pain models.

Migraine models used to observe the biomarker or activity may be in vitro and in vivo and may be vascular, neuronal, and behavioral models. In vitro vascular models may include models of vasodilation and vasoconstriction in isolated human or animal arteries and veins, or other models. Neurovascular models may include models targeting activation and modulation of the trigeminovascular system, for instance models of trigeminal stimulation and plasma protein extravasation, models of stimulation of the meninges, models of stimulation of the superior sagittal sinus, models of c-Fos expression within the trigeminal nucleus caudalis (TNC), models of nitric oxide donors, models of cortical spreading depression with a focus on 5HT-1B/1D receptors, CGRP receptors, or other receptors such as NMDA receptors, models of central pain sensitization focused on the trigeminal nerve, or other models.

In vivo vascular models may include models which measure arterial or veinal diameter of, for instance, the carotid arterial bed, arteriovenous anastomoses, and pial arteries, models of intravital microscopy, and models of meningeal blood flow, or other models. Anesthetized models may include models of intracranial dural stimulation, models of brainstem dysfunction/modulation, models of cortical spreading depression targeting aura, models of pharmacological provocation, or other models.

Behavioral models may include models of trigeminovascular nociception, models of spontaneous nociceptive responses in the craniofacial region, models of associated neurological symptoms, models of associated symptoms of migraine or sensitization such as photophobia, phonophobia, osmophobia, or other symptoms, or other models.

Genetic models may include CACNA1A mouse models, ATP1A2 mouse models, casein kinase 1 delta mouse models, TRESK mouse models, models targeting familial or sporadic hemiplegic migraine, or other models.

Models of chronic migraine may include models of nitroglycerin, models of medication overuse headache, models of spontaneous trigeminal allodynia, models of monogenic migraine mutation, or other models.

Models may be different vascular and neuronal models than the models described which incorporate techniques and tools such as laser doppler flowmetry, micro-iontophoresis and/or microinjection, histology and/or immunohistochemistry, biochemistry, evoked behavioral testing, spontaneous behavioral testing, conditioned placed preference or aversion, elevated plus or zero maze, or other models intended to measure the desired biomarker or indication of activity.

Other pain models which may be used may include peripheral inflammation and peripheral neurogenic inflammation models such as complete Freund's adjuvant (CFA), models applying carrageenan, mustard oil, bee venom, capsaicin, and formalin, models of chronic postischemia pain, models of chronic constriction injury, spinal nerve ligation, phototoxicity, distal nerve injury, complete nerve transection, trigeminal ganglion compression, experimental osteolytic sarcoma, experimental squamous cell carcinoma, experimental melanoma, models of muscle pain, or other models.

In each of the above models, it is expected that a composition of the present disclosure will reduce migraine pain or migraine frequency. Furthermore, other pain models detailed above may be used to demonstrate that a composition of the present disclosure reduces fibromyalgia pain.

Example 2: FHM Study

This study will evaluate cannabinoids combinations that normalize (1) cortical spreading depression (CSD) properties, (2) behavioral responses, and (3) parameters of neuroinflammation in FHM1 or FHM2 mice compared to WT mice.

The study will monitor altered cortical spreading depression (CSD) properties, via experiments inducing CSD. The study will also evaluate behavioral and neuroinflammatory responses in the context of allodynia. For instance, pain measurements, specifically von Frey filament testing of periorbital region or hind paw and pain-relevant behavior using a home-modified version of the mouse grimace scale (MGS) will be monitored. Assessment of pain-relevant behavior with MGS will be performed at 24, 48 and 72 hours after injection. Neuroinflammation will be assessed using immunohistochemistry (IHC) conducted on relevant brain sections using relevant markers e.g. of HMGB1, NF-κB, and microglial activation.

FHM1 transgenic mice will be compared to WT—for instance, comparing Thy1-ChR2 (Thy1-driven expression of Channel rhodopsin 2)/FHM1 to Thy1-ChR2/WT mice.

Different ratios and combinations of cannabinoids will be evaluated, including 100:1 and 30:1 ratio of CBD:THC mg/kg.

Example 3: Migraine Studies

Cannabinoid combinations will be evaluated using at least two migraine models. First, a peripheral injection of a nitric oxide (NO) donor nitroglycerin (NTG) aka glyceryl trinitrate (GTN) to induce migraine-like symptoms in mice—a generally accepted model extensively used and described and induces evoked and spontaneous pain in rodents. Second, a CGRP-induced migraine model will be evaluated.

Different ratios of CBD:THC will be tested to reduce NTG-induced migraine-like phenotypes in mice. Migraine-like behaviors in the mice (light aversion, periorbital tactile hypersensitivity, and facial signs of discomfort) will be evaluated. Animals will be injected with NTG or vehicle, and one of the following treatments: vehicle, CBD (1-100 mg/kg, i.p.), THC (1 mg/kg i.p. fixed dose), or a combination of CBD:THC (1:1, 3:1, 10:1, 30:1, 60:1, 100:1, and 300:1 where 300:1 is 300 mg/kg CBD and 1 mg/kg THC). Both male and female mice will be tested.

The adverse effects of the different combinations of CBD:THC will also be evaluated in mice. Experiments will test for depression (tail suspension), activity and motor alterations (voluntary wheel activity), and cognitive alterations (Y maze). Mice will be injected (i.p.) with vehicle, CBD, THC, or the different combinations of CBD:THC listed above.

Example 4: Migraine Studies

Locomotor function was assessed using the rotarod (see Assay description and relevant methods in Example 5).

Mice are placed on a turning rod with increasing speed of rotation. Latency to fall from the rod is collected. The results are shown in FIG. 1A. The top panel shows the latency to fall from the rod over 3 consecutive 5 min trials (two-way ANOVA [time and treatment], treatment factor p=0.46, interaction factor p=0.89; N=9-11 per group). The bottom panel shows the average latency to fall from the rod for the 3 trials (one-way ANOVA, treatment factor p=0.46; N=9-11 per group).

FIG. 1A shows that only THC alone and the 1:1 ratio seemed to increase motor function (trend only). However, caffeine at 100 mg/kg i.p. which was the positive control of this experiment was shown to induce a decreased time to fall from the rod didn't yield the expected results. A second cohort was needed to gain power and solve the positive control issue.

Figure 1B:
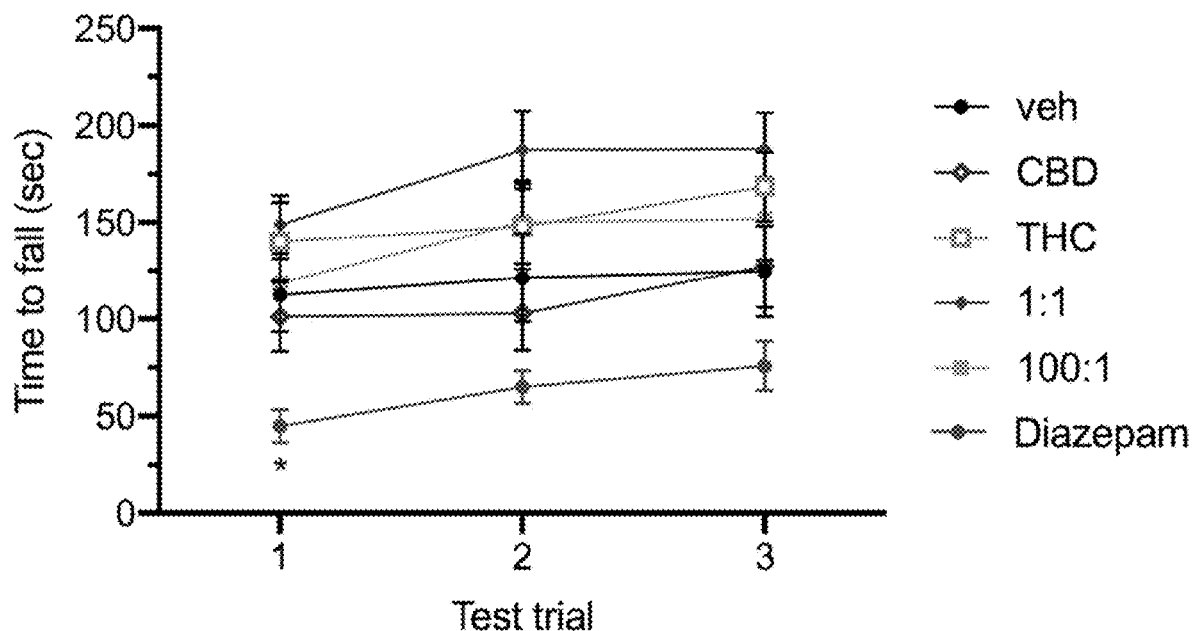
Figure 1B:
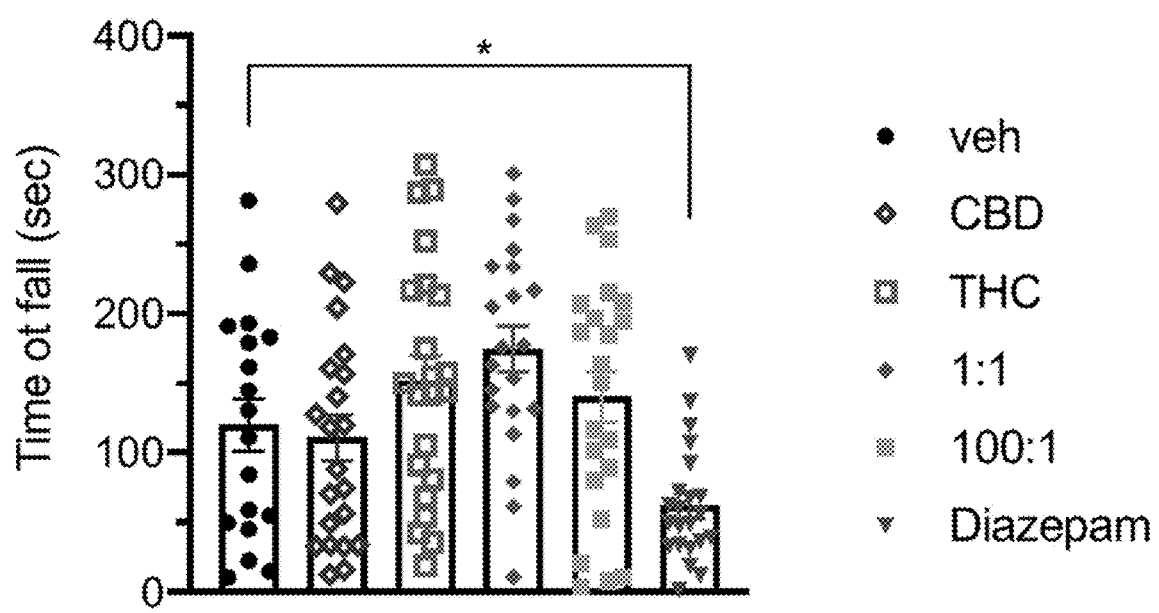

FIG. 1B shows a rotarod trial wherein the positive control was diazepam, which produced the expected increased time to fall. The top panel shows the latency to fall from the rod over 3 consecutive 5-minute trials (Two-way ANOVA [time and treatment], treatment factor $p<0.0001$; Tukey's multiple comparison $*p<0.05$; against veh. group). The bottom panel shows the average latency to fall from the rod for the 3 trials (One-way ANOVA $p<0.0001$; Tukey's multiple comparison $*p<0.05$; against veh. group).

Example 5: Photophobia Experiments

Methods
Animals

Sixty-four male and 64 female wild-type CD1 (Charles River, USA) mice were used. Mice were 8-9 weeks of age upon arrival at our facility and allowed to acclimate for a week before use. Mice were housed in groups of 4 per cage, on a 12 h light cycle with food and water ad libitum. Lights were turned on at 6 AM and turned off at 6 PM. For all experiments, investigators were blinded to drug treatment and animals randomized (block randomization) to each treatment group prior to commencement of experiments. For each assay, mice were brought to the experimental room one hour prior to the beginning of the experiment for acclimation. Animal procedures were approved by the University of Iowa Animal Care and Use Committee and performed in accordance with the standards set by the National Institutes of Health and the ARRIVE guidelines.

Drug Administration

All drugs were administered by intraperitoneal (i.p.) injection. CGRP and caffeine were administered at 10 μl/g bodyweight with a 30 g×0.5 needle. CBD, THC and the diverse ratios of CBD:THC were administered at 3.3 μl/g bodyweight with a 23 g×0.5 needle. Rat α-CGRP (Sigma-Aldrich, USA) was administered at 0.1 mg/kg, caffeine (Sigma-Aldrich, USA) was administered at 100 mg/kg, and both were diluted in vehicle, Dulbecco PBS (Hyclone, GE Healthcare Life Science, USA). CBD was administered at 1 or 100 mg/kg, THC was administered at 1 mg/kg, and both were diluted in vehicle sunflower oil (Sigma-Aldrich, USA) Animals were gently held but not anesthetized during injection. Mice were allowed to recover for 30 to 60 min in their home cages before testing (see figure legend and experimental design for precisions).

Light Aversion Assay

The light/dark assay was used to measure the animals' aversion to bright light, which is a surrogate for photophobia. Briefly, mice were placed individually in light/dark boxes that consist in two compartments, one brightly lit and the other not lit, black and fully enclosed. Mice can move freely in between them. An infrared beam tracking system (Med Associates) monitors and quantifies the behavior. Light-aversive animals will spend more time in the dark compartment than naïve animals Data were collected using Activity Monitor version 7.06 from twelve chambers as previously described. Mice were pre-exposed to the chamber once (baseline, data not shown) to reduce exploratory drive, then tested with bright light (25,000 lux). Data were collected for 30 min and analyzed in sequential 5 min intervals. The time in light was reported as the mean+/−SEM of all the mice at each interval and as the mean+/−SEM of the average time per interval for each individual mouse.

Y Maze Assay

The Y-maze assay was used to measure spatial memory using a 3-arm maze. The assay is divided into two trials separated by an intertrial period. During the first trial, one arm (novel arm) is closed, and mice are left to explore the two other arms for 5 min. Mice are then placed back in their home cages for the 2 min intertrial period. During the second trial, mice are able to explore all arms. A mouse with a good spatial memory will enter the previously unexplored (novel) arm more frequently than the other arms. A mouse with poor spatial memory will show no preference. The number of entries and time in the novel arm during the second trial was reported as the mean+/−SEM of all the mice at each interval (30 sec) and as the mean+/−SEM of the total time for the trial for each individual mouse.

Rotarod Assay

The rotarod assay was used to measure impaired motor function in mice. The assay is divided into three trials of 5 min each separated by 10 min of resting time. For each trial, mice are place on a stationary rod. Once the animal is in place, the rod rotation was initiated at a rate of 4 rpm per min, with increasing speed up to 60 rpm at 5 min. Each animal was trained for two days following this protocol and tested on the third day. The latency to fall from the rod was reported as the mean+/−SEM of all the mice for each trial.

Experimental Design

Figure 2:
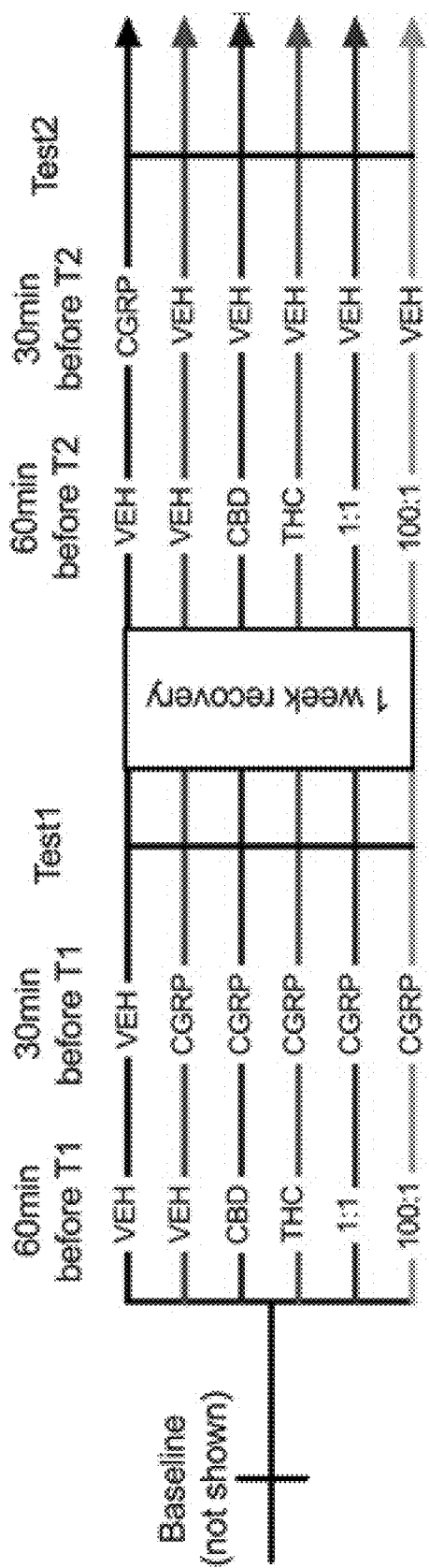
FIG. 2 shows the experimental design for light aversion experiments.

The experimental design for this cohort is presented in FIG. 2. The same animals were used to assess light aversion (light-dark assay), spatial memory (Y-maze) and motor function (Rotarod). Animals were randomly assigned to 6 groups: negative control group (veh, sunflower oil), positive control group (CGRP 0.1 mg/kg or caffeine 100 mg/kg depending on the assay), CBD (100 mg/kg), THC (1 mg/kg), 1:1 (1 mg/kg of both CBD and THC), or 100:1 (100 mg/kg of CBD and 1 mg/kg of THC). Groups stayed the same throughout the experiment (i.e. mice injected with 100:1 were always the same in the different assays).

A week after their arrival at the facility, animals were pre-exposed to the light aversion chambers (Baseline, data not shown) in order to decrease the exploratory drive on subsequent exposures. Mice were then tested for light aversion twice, with one week between tests.

Test 1: test the efficacy of CBD and/or THC on CGRP-induced light aversion. Drug administration was performed i.p. by ASW or AK, 60 minutes prior to testing. Thirty minutes before testing, animals were injected a second time with CGRP (0.1 mg/kg) in order to induce the migraine-like state. Only one group was administered with PBS and represents the negative control in this run. The group that received sunflower oil+CGRP represents the positive control. Those injections were also performed i.p by ASW or AK. Thirty minutes later, animals were placed in the light aversion chambers, and tested for 30 minutes.

Test 2: test the possible effects of CBD and/or THC by themselves on light aversion. Animals were given a week to recover. Then the same groups were used for Test 2, and only the second injection was reversed. All groups received vehicle 30 minutes before testing, except for the first group that was administered with CGRP and was the positive control for this test. The group receiving sunflower oil+PBS was the negative control for this test (red line).

A week after Test 2, spatial memory was assessed using Y-maze. Administration of drugs was performed 60 min prior to testing except for CGRP (positive control) which was administered 30 min prior to testing.

A week after Y-maze, motor function was assessed using rotarod. Administration of drugs was performed 60 min prior to testing except for caffeine (positive control) which was administered 30 min prior to testing.

Results

A. Light Aversion

CBD:THC Ratio 100:1 Alleviates Light Aversion Induced by CGRP Administration.

Figure 3A:
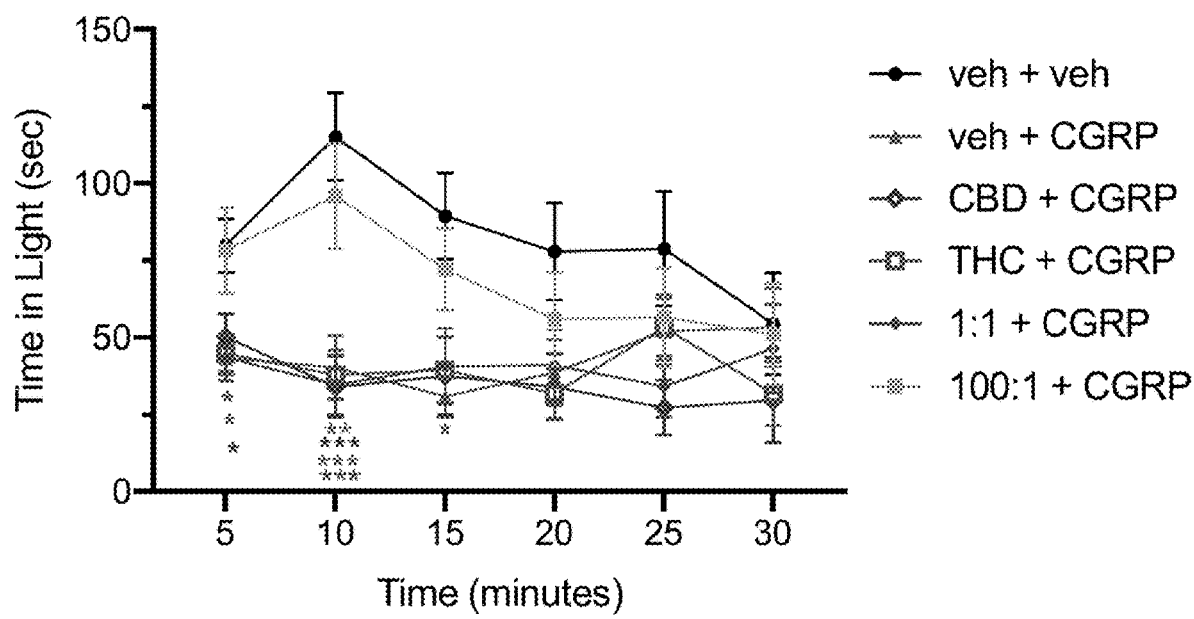
FIGS. 3A-3D shows the effect of different ratios of CBD and THC on light aversion. The left panel of each figure shows light aversion measured as a function of time over a 30-minute period. The right panel of each figure shows the average time spent in the light compartment per 5 minutes during the entire test period.
Figure 3A:
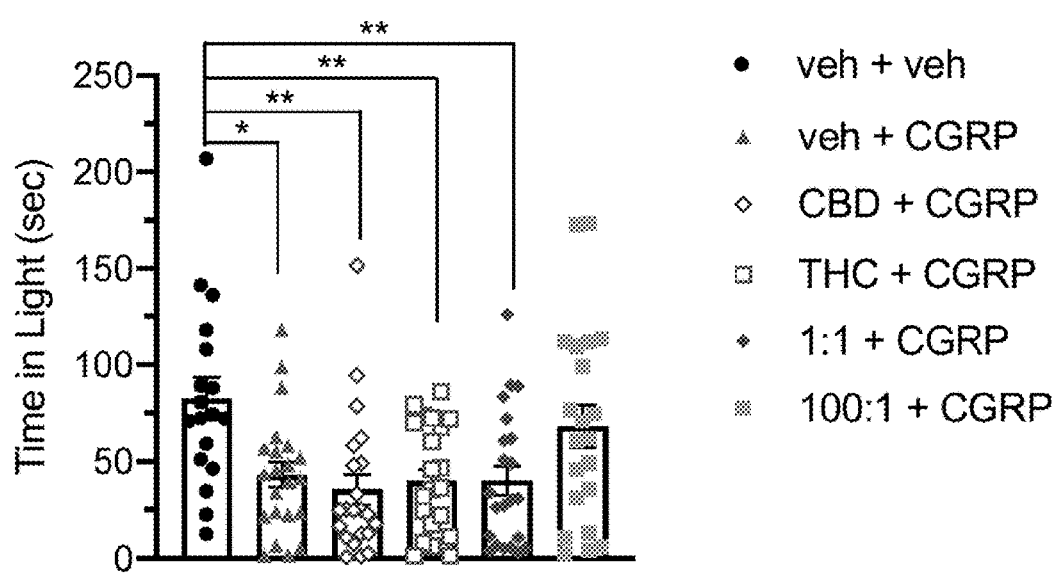
Figure 3B:
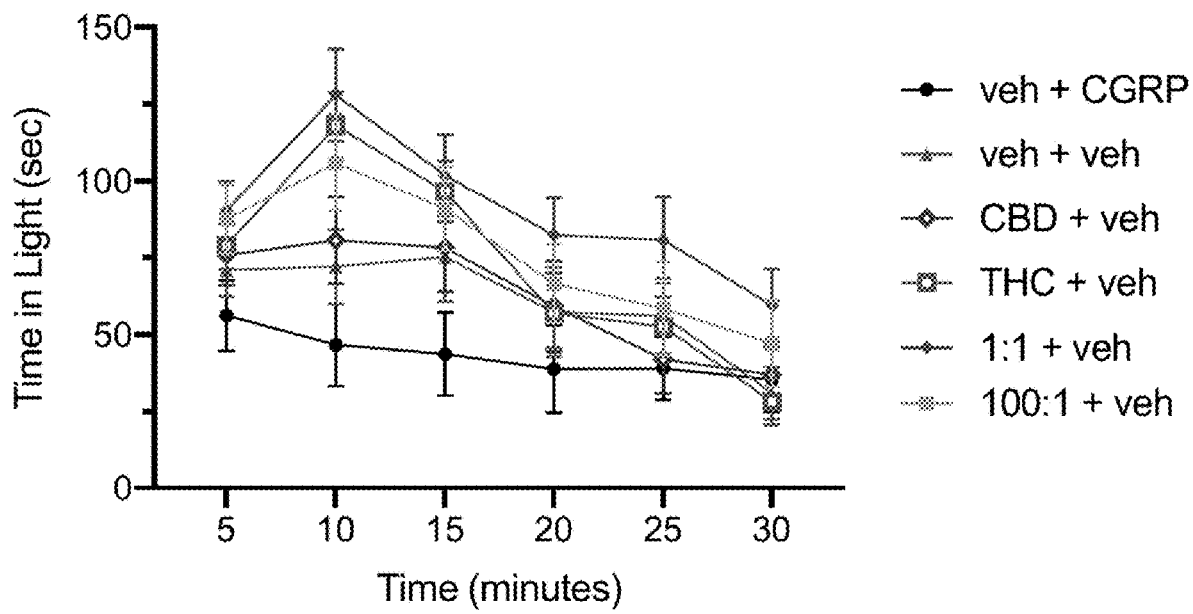
Figure 3B:
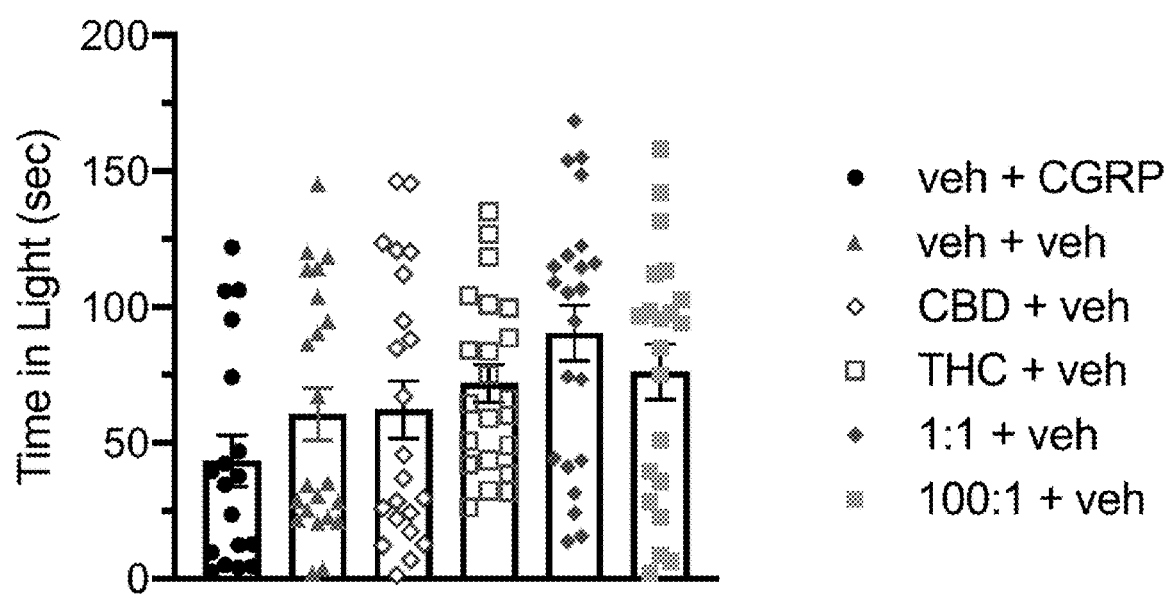

Light aversion was measured both as a function of time over a 30 min testing period (FIGS. 3A-3B top panel; two-way ANOVA [time and treatment], treatment factor $p=0.0005$, interaction factor $p=0.0249$; Tukey's multiple comparison, $*p<0.05$; $p<0.01$; $*p<0.001$ against veh+veh group at corresponding time-points; N=18-22 per group), and data are also represented as the average time spend per 5 min during the entire test period (FIGS. 3A-3B bottom panel; one-way ANOVA, treatment factor $p=0.0005$; Tukey's multiple comparison, $*p<0.05$; $**p<0.01$; $p<0.001$ against veh+veh group; N=18-22 per group).

Compared to our negative control consisting of mice injected with vehicles (sunflower oil and PBS, black circles), injection of CGRP+veh induces a significant decrease in time spent in the light and represents the positive control in this experiment (red triangles). The co-administration of CBD alone (blue diamonds), THC alone (green squares), or of the CBD:THC ratio 1:1 (purple diamonds) failed to reverse the CGRP-induced decrease in time spent in the light. Co-administration of the CBD:THC ratio 100:1 (orange squares) almost completely alleviated the CGRP-induced light aversion and was no longer significantly different from the negative control group.

Although we are not powered to see subtle differences, we then analyzed the data by sex. The lack of power makes those results more difficult to interpret. Female results are presented in FIG. 3C. The left panel shows the time spent in the light compartment every 5 minutes during the assay over 30 minutes (Two-way ANOVA [time and treatment], treatment factor $p=0.21$, interaction factor $p=0.0069$; Tukey's multiple comparison, $p*<0.05$ against veh+veh group at corresponding time-points; N=9-11 per group). The right panel shows the average time per 5 minutes spent in the light compartment (One-way ANOVA, treatment factor $p=0.17$; N=9-11 per group. Male results are presented in FIG. 3D. The left panel shows the time spent in the light compartment every 5 min during the assay over 30 min (Two-way ANOVA [time and treatment], treatment factor $p=0.0032$, interaction factor $p=0.76$, Tukey's multiple comparison, $*p<0.05$ against veh+veh group at corresponding time-points; N=9-11 per group). The right panel shows the average time per 5 min spent in the light compartment (one-way ANOVA, treatment factor $p=0.0057$; Tukey's multiple comparison, $*p<0.05$; N=9-11 per group).

Figure 3C:
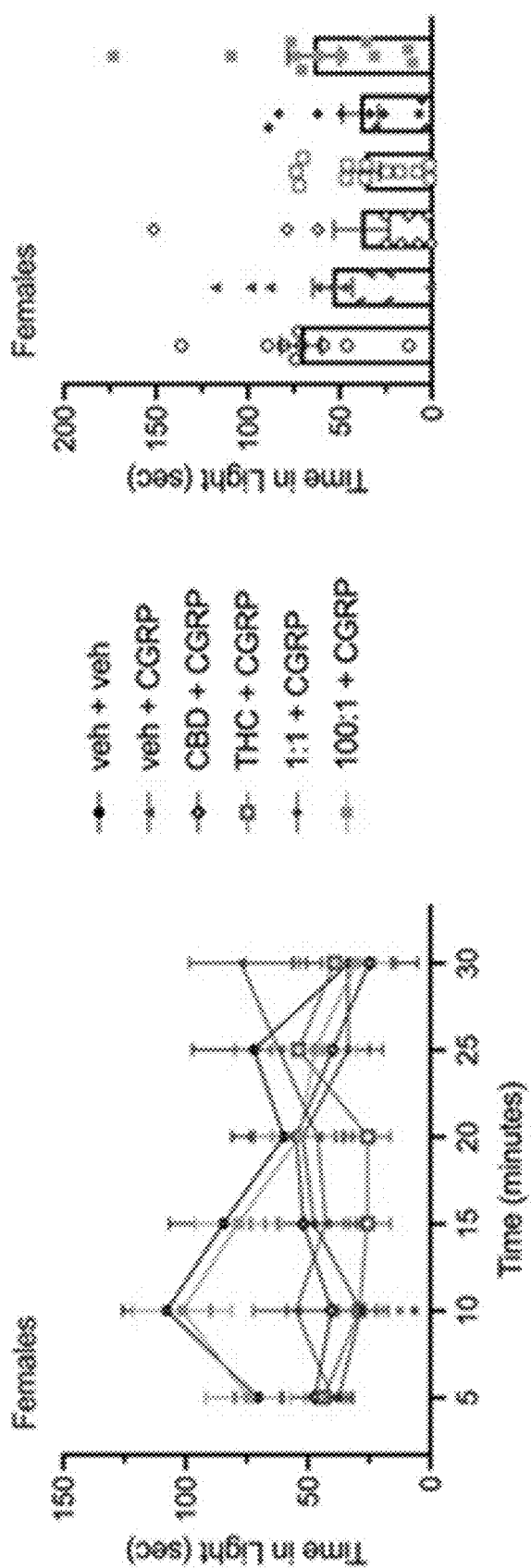

Unfortunately, the difference between the negative control (veh+veh) and the positive control (CGRP+veh) in females was not as robust as we would hope (especially in the later time points) making further interpretation difficult (FIG. 3C). Based on the first 15 minutes of the assay however, it appears that once again, only the 100:1 ratio of CBD:THC alleviates light aversive behavior in females, while other doses don't.

Figure 3D:
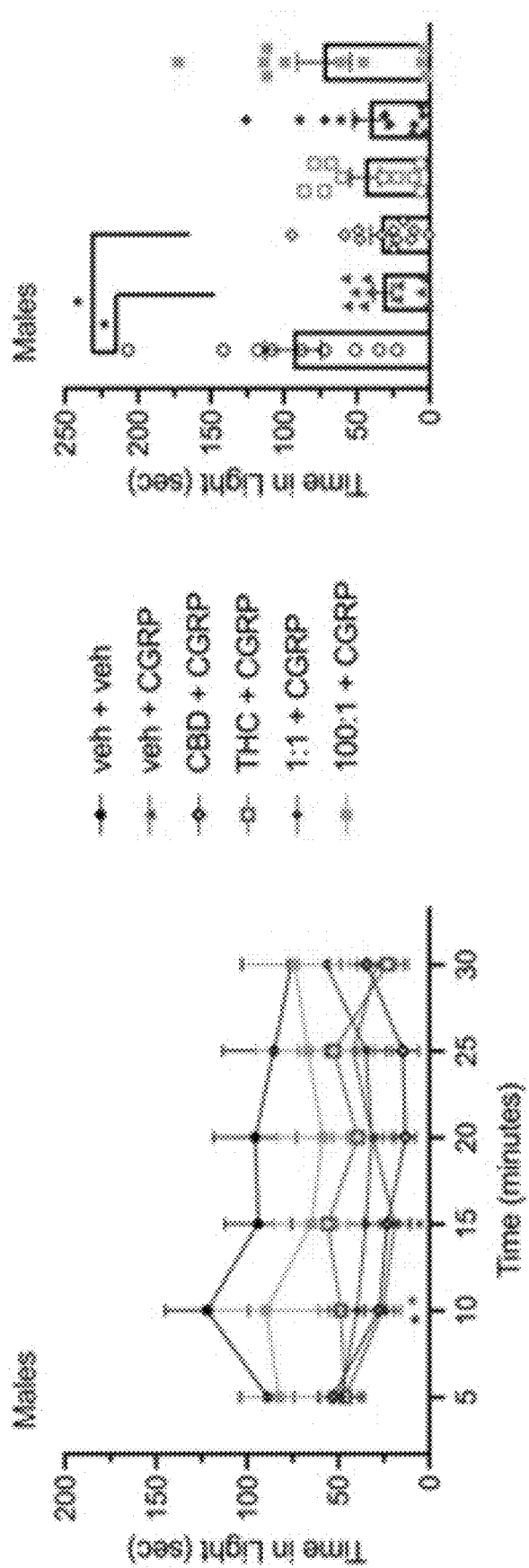

The positive and negative controls in males show a robust difference with CGRP+veh inducing a strong and significant decrease of the time spent in the light compartment compared to veh+veh group (FIG. 3D). Once again, the 100:1 group shows the best rescue, while the other treatments don't appear to alleviate the phenotype at all.

Figure 4:
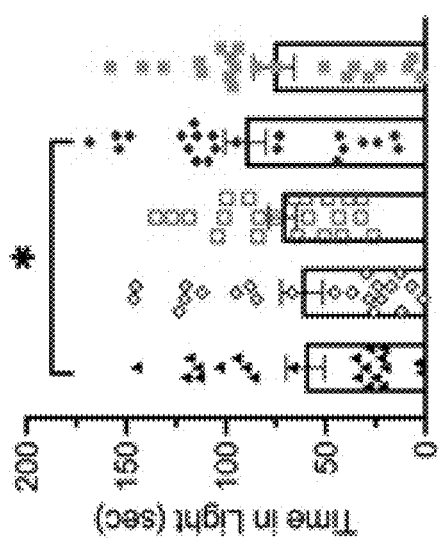
FIG. 4 shows the effect of different ratios of CBD and THC on light aversion without a CGRP trigger. The left panel shows light aversion measured as a function of time over a 30 minute period. The right panel shows the average time spent in the light compartment per 5 minutes during the entire test period.
Figure 4:
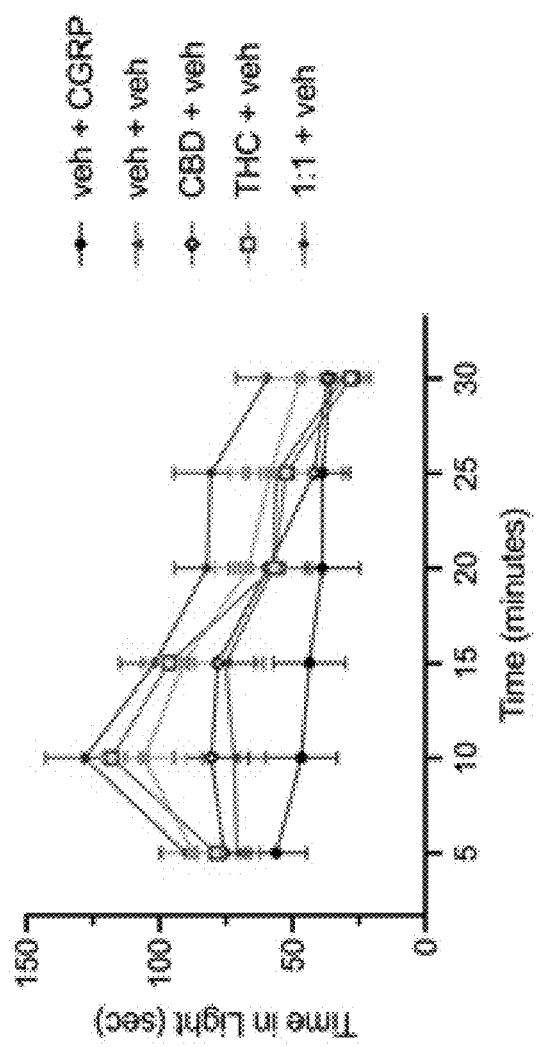

As a control for this experiment, the effect of the different ratios of CBD:THC were tested on the same animals in the absence of the CGRP trigger. In this experiment, CGRP+veh (black circles) serves as the positive control compared to veh+veh (red triangles, negative control). The results are shown in FIG. 4. The left panel shows the time spent in the light compartment every 5 minutes during the assay over 30 minutes (Two-way ANOVA [time and treatment], treatment factor p=0.0256, interaction factor p=0.0394; Tukey's multiple comparison, not significant. N=18*22 per group). The right panel shows the average time per 5 minutes spent in the light compartment (One-way ANOVA, treatment factor p=0.0256; Tukey's multiple comparison, not significant; N=18-22 per group).

Unfortunately, the negative control group in this experiment yields lower results than expected (which is not unexpected when animals are tested in this assay for the third time), but the CGRP+veh mice are nevertheless spending less time in the light than the veh+veh mice. All other groups are spending between 75 and 125 sec average time in the light, which is within the normal range. Whether those results that are higher than the veh+veh group have a biological implication has yet to be determined. This experiment might have to be re-evaluated using a new cohort of naïve mice.

Effect of the Different Ratios of CBD and THC on CGRP-Induced Increase Resting Time in the Dark.

Figure 5A:
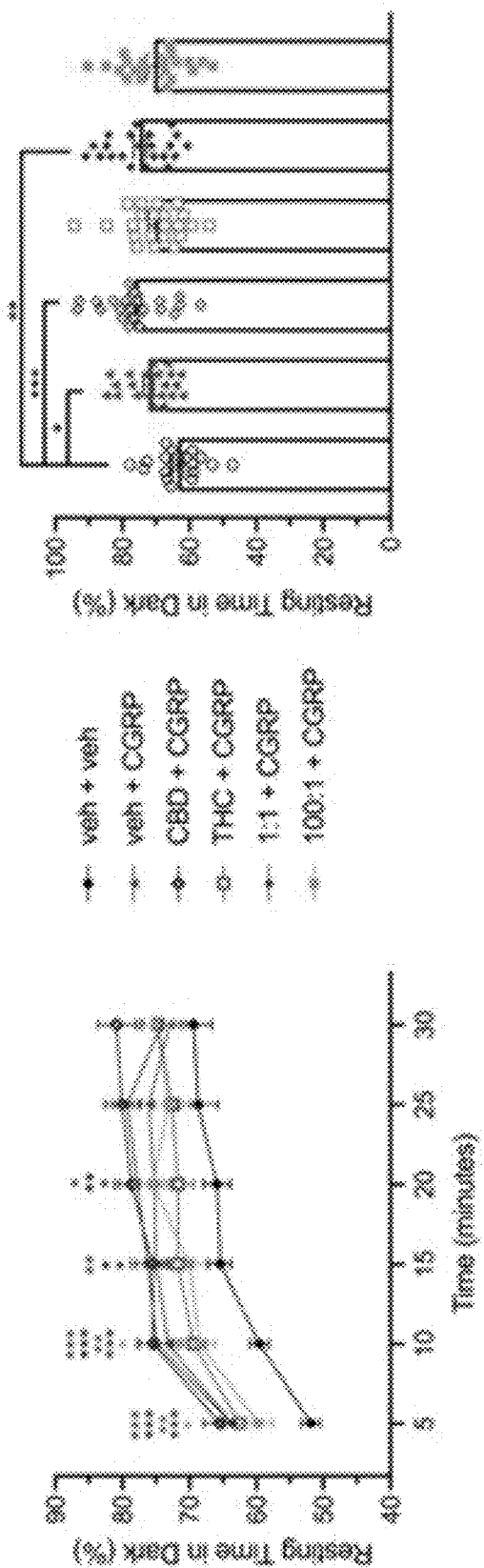
FIGS. 5A-5C show the effect of different ratios of CBD and THC on the time mice spent resting in the dark compartment during the light aversion test. The left panel of each figure shows the time mice spent resting in the dark over a 30-minute period. The right panel of each figure shows the average time spent in the dark compartment per 5 minutes during the entire test period.

When migraine patients sustain an attack, it's common for them to seek the dark and rest. Mice show a similar behavior. In the present study, compared to the negative control (veh+veh), the positive control (CGRP+veh) induces a significant increase in the time spent resting in the dark, both when data is plotted as a function of time (FIG. 5A left panel), or as averages (FIG. 5A right panel). The left panel shows the time spent resting in the dark compartment every 5 minutes during the assay over 30 minutes (Two-way ANOVA [time and treatment], treatment factor p=0.0004, interaction factor p=0.0643; Tukey's multiple comparison, *p<0.05; p<0.01; *p<0.001 against veh+veh group at corresponding time-points; N=18-22 per group). The right panel shows the average time per 5 min spent resting in the dark compartment (One-way ANOVA, treatment factor p=0.0004; Tukey's multiple comparison, *p<0.05; p<0.01; *p<0.001 against veh+veh group; N=18-22 per group).

When co-administered with CGRP, neither CBD alone nor the 1:1 ratio reversed this increased resting time. While THC alone and the 100:1 ratio are still different from the veh+veh group for the first 10 minutes of the assay, those two treatments seem to attenuate the phenotype, and those groups are no longer significantly different from veh+veh when data is potted as averages (FIG. 5A right panel).

Figure 5B:
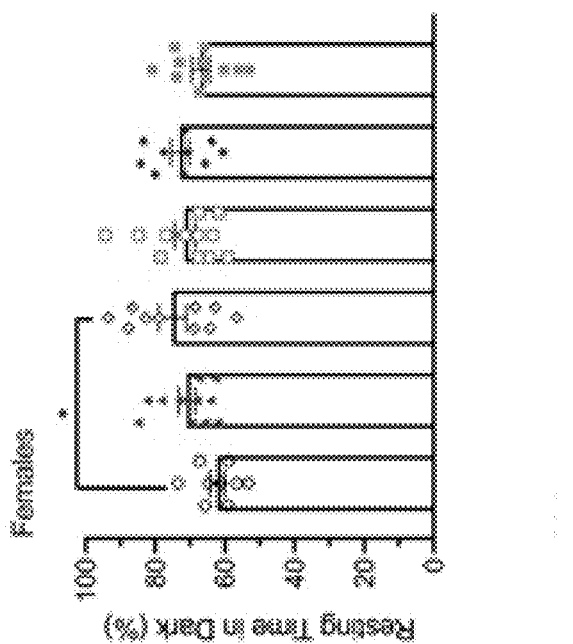
Figure 5B:
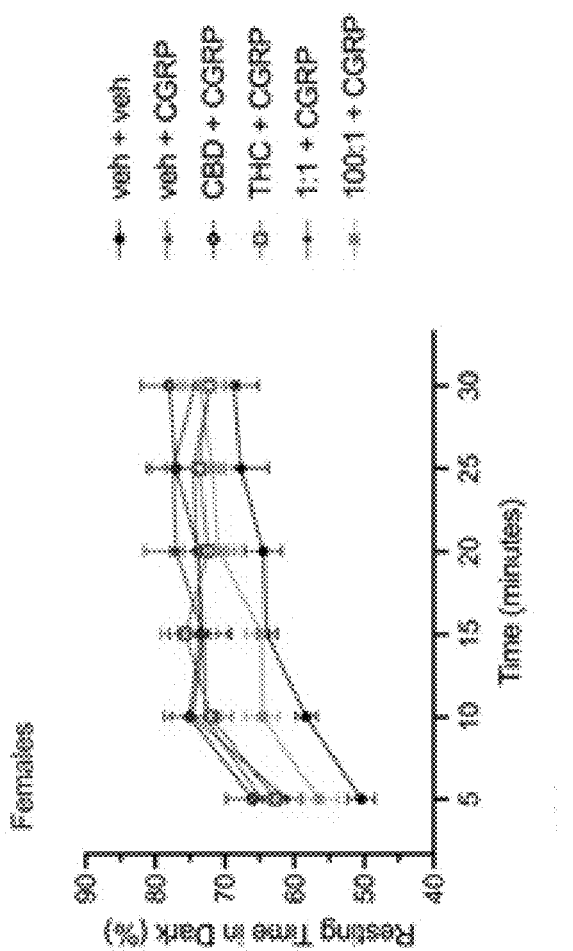
Figure 5C:
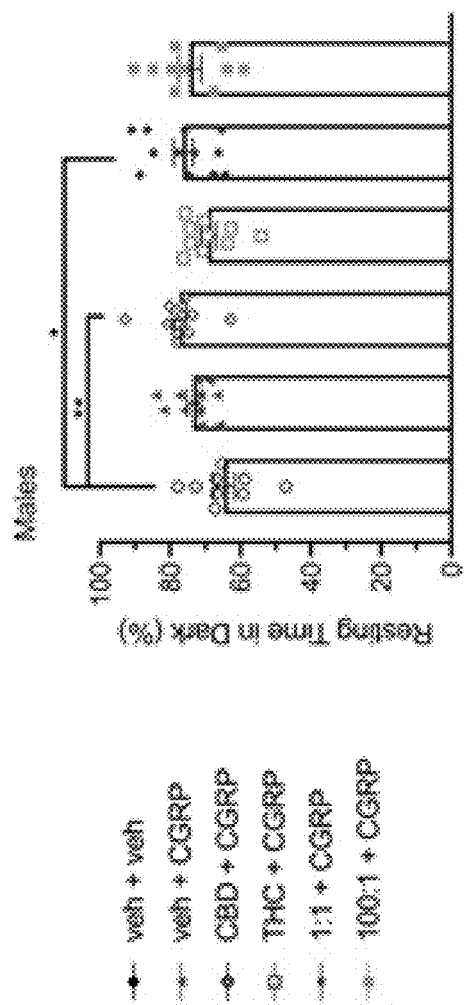
Figure 5C:
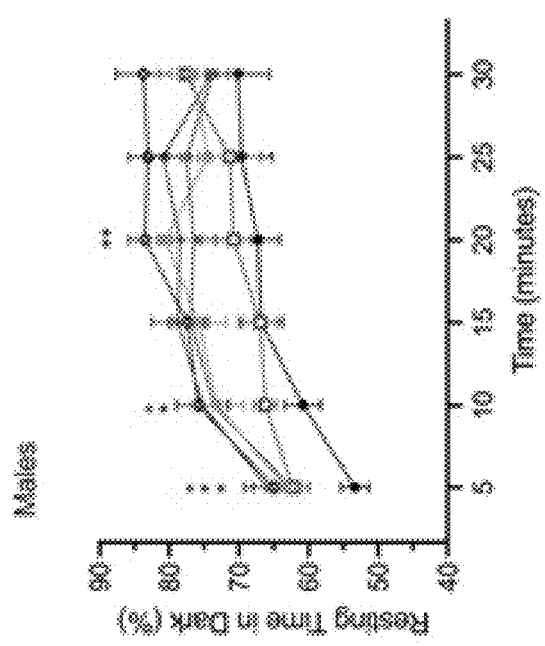

Although we are not powered to see subtle differences, we then analyzed the data by sex. The lack of power makes those results more difficult to interpret. Female results are presented in FIG. 5B, and males in FIG. 5C. The left panel in FIG. 5B shows the time spent resting in the dark compartment every 5 minutes during the assay over 30 minutes (Two-way ANOVA [time and treatment], treatment factor p=0.066, interaction factor p=0.16). The right panel in FIG. 5B shows the average time per 5 minutes spent in the light compartment (One-way ANOVA, treatment factor p=0.0483; *p<0.05; N=9-11 per group). The left panel in FIG. 5C shows the time spent resting in the dark compartment every 5 minutes during the assay over 30 minutes (Two-way ANOVA [time and treatment], treatment factor p=0.0077, Interaction factor p=0.0805; Tukey's multiple comparison, *p<0.05; p<0.01 against veh+veh group at corresponding time-points; N=9-11 per group). The right panel in FIG. 5C shows the average time per 5 minutes spent in the light compartment (One-way ANOVA, treatment factor p=0.0078; Tukey's multiple comparison, p<0.05; **p<0.01; N=9-11 per group).

In females, only the 100:1 ratio seemed to alleviate the increased resting in the dark induced by CGRP administration, while in males, only THC alone seemed to have an effect.

Effect of the Different Ratios of CBD and THC on the Resting Time in the Light.

Figure 6:
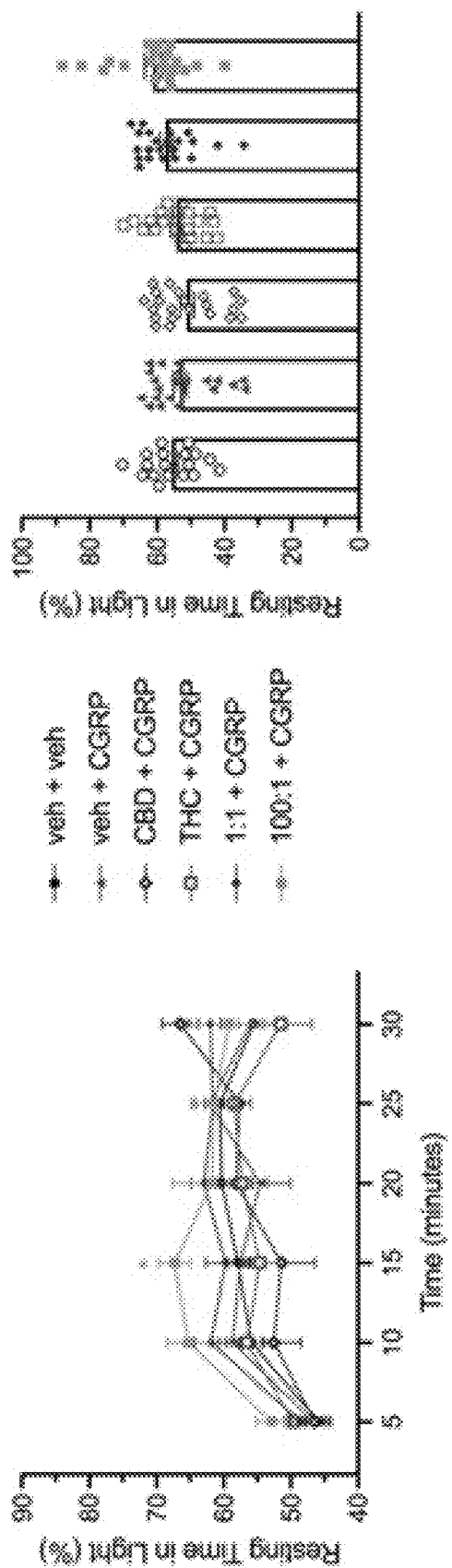
FIG. 6 shows the effect of different ratios of CBD and THC on the resting time in the light during the light aversion test. The left panel shows the time spent resting in the light compartment every 5 min during the assay over 30 min. The right panel shows the average time per 5 min spent resting in the light compartment.

The left panel of FIG. 6 shows the time spent resting in the light compartment every 5 minutes during the assay over 30 minutes (Two-way ANOVA [time and treatment], treatment factor p=0.0293, interaction factor p=0.059; Tukey's multiple comparison, *p<0.05 against veh+veh group at corresponding time-points; N=18-22 per group). The right panel of FIG. 6 shows the average time per 5 minutes spent resting in the light compartment (One-way ANOVA, treatment factor p=0.0084; Tukey's multiple comparison, not significant; N=18-22 per group).

As was expected from previously published results, CGRP injection does not increase the time spent resting in the light compartment (CGRP+veh group, FIG. 6). Only the CBD:THC ratio of 100:1 induces a significant increase in time spent resting in the light when data is presented as a function of time. CBD:THC ratio 30:1 also alleviates light aversion induced by CGRP administration.

Figure 7:
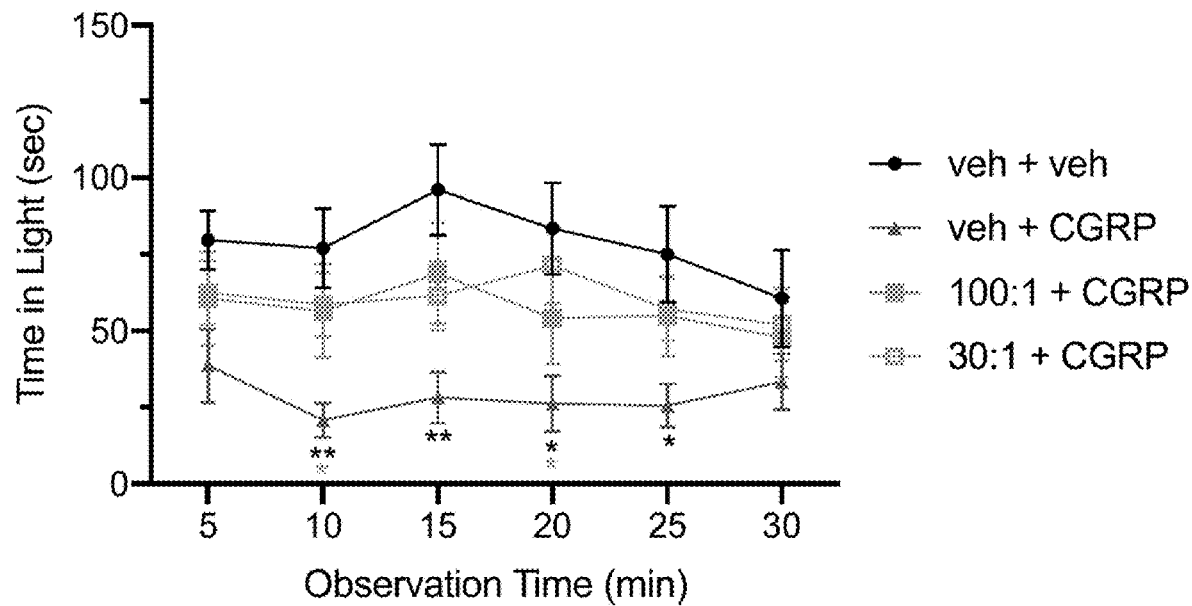
FIG. 7 shows the effect of different ratios of CBD and THC on light aversion induced by CGRP administration. The left panel shows the time spent resting in the light compartment every 5 min during the assay over 30 min. The right panel shows the average time per 5 min spent resting in the light compartment.
Figure 7:
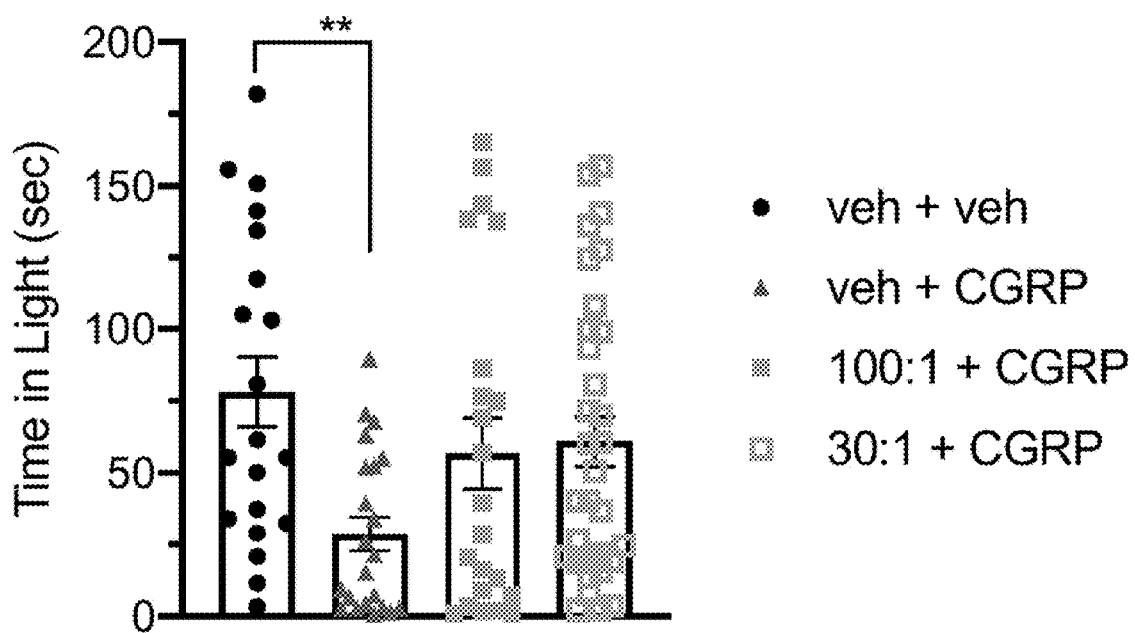

Light aversion was measured as above, function of time over a 30 min testing period (FIG. 7, top panel: two-way ANOVA [time and treatment], treatment factor p=0.0117; Tukey's multiple comparison, dark *p<0.05; **p<0.01; against veh group. light *p<0.05; veh+CGRP vs 30:1+CGRP). Data are also represented as the average time spend per 5 min during the entire test period (FIG. 7, bottom panel; one-way ANOVA, p=0.0124; Tukey's multiple comparison, **p<0.01; against veh group).

Figure 8:
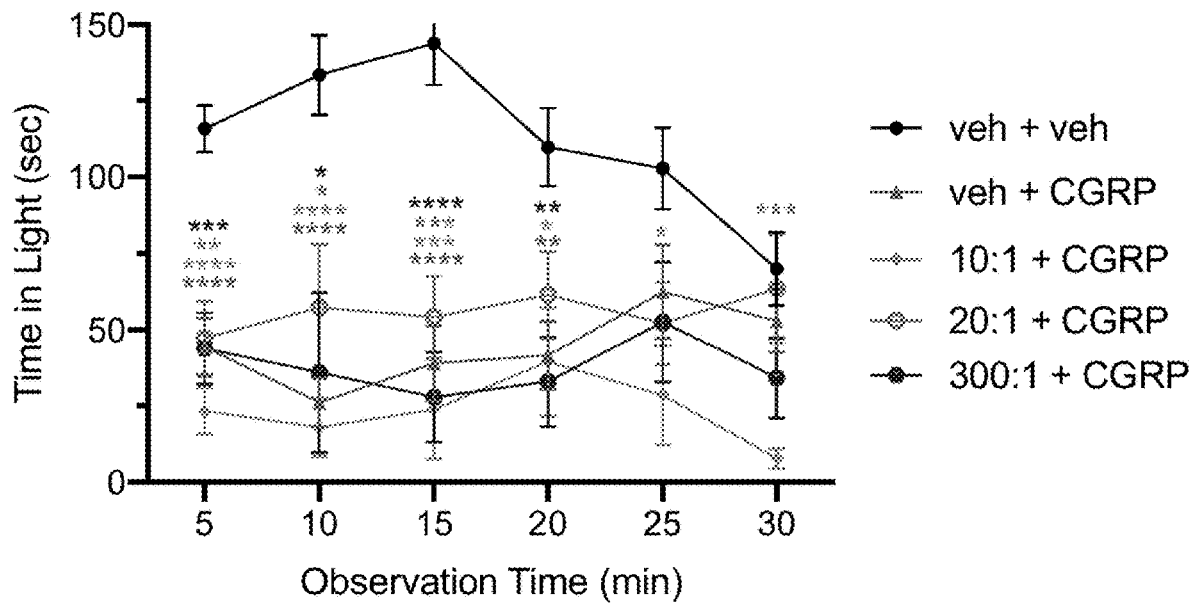
FIG. 8 shows the effect of different ratios of CBD and THC on light aversion induced by CGRP administration. The left panel shows the time spent resting in the light compartment every 5 min during the assay over 30 min. The right panel shows the average time per 5 min spent resting in the light compartment.
Figure 8:
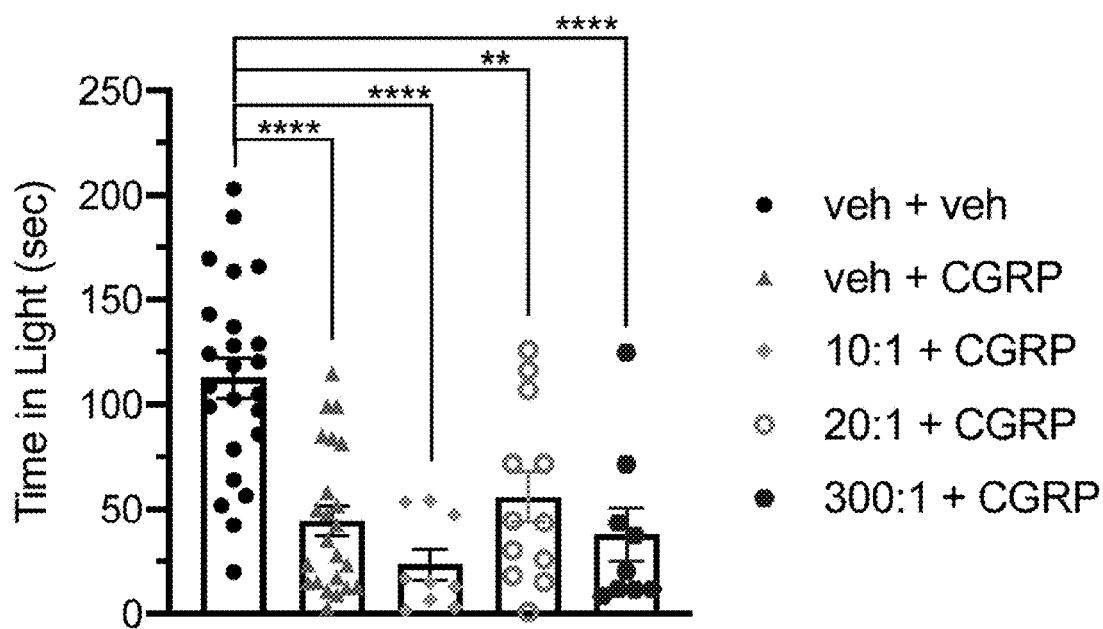

Compared to our negative control consisting of mice injected with vehicles (sunflower oil and PBS, black circles), injection of CGRP+veh induces a significant decrease in time spent in the light and represents the positive control in this experiment (red triangles). Co-administration of the CBD:THC ratio 100:1 (orange squares) was included as our control ration that alleviates the CGRP-induced light aversion. Co-administration of CBD:THC 30:1 alleviated the CGRP-induced light aversion and was no longer significantly different from the negative control group. CBD:THC ratios 300:1, 20:1 and 10:1 did not alleviate light aversion induced by CGRP administration Light aversion was tested as in the above experiments. The results are shown in FIG. 8. The top panel shows the time spent in the light every 5 minutes for 30 minutes (Two-way ANOVA [time and treatment]; treatment factor p<0.0001; Tukey's multiple comparison, *p<0.05; p<0.01; *p<0.001; **p<0.0001 against veh+veh group at corresponding time point) and the bottom panel shows the average time spent in the light during treatment (one-way ANOVA; p<0.0001; Tukey's multiple comparison, p<0.01; ****p<0.0001 against veh+veh group).

Co-administration of CBD:THC ratios, 300:1 (blue circles), 20:1 (avocado green open circles), 10:1 (gray diamonds) did not alleviate the CGRP-induced light aversion.

CBD:THC (100:1) Alleviates SNP-Induced Light Aversion

Figure 9:
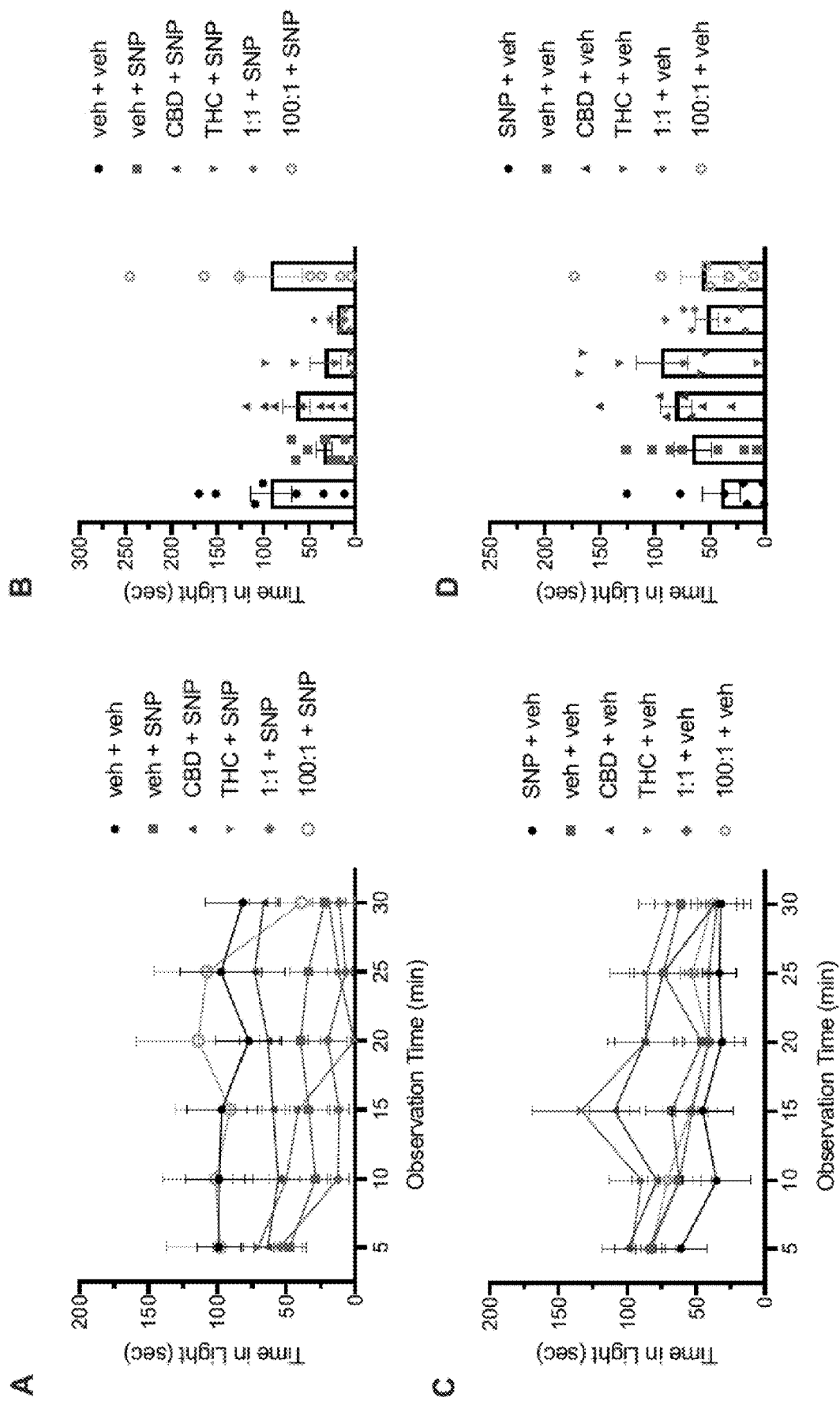
FIG. 9 shows the effect of different ratios of CBD and THC on light aversion induced by SNP administration for two cohorts. Panels A and C show the time spent resting in the light compartment every 5 min during the assay over 30 min for the two cohorts. Panels B and D show the average time per 5 min spent resting in the light compartment for the two cohorts.

Light aversion was assessed. In this experiment an injection of SNP+veh (red squares) was used as a positive control for light aversion. The results are shown in FIG. 9. Panel A shows the time spent in light every 5 minutes during Test 1 (two-way ANOVA [time and treatment]; treatment factor p=0.0461; Tukey's multiple comparison against veh+veh group at corresponding time points; not significant). Panel B shows the average time spent in the light during Test 1 (one-way ANOVA; p=0.0461; Tukey's multiple comparison against veh+veh group [ns]). Panel C shows the time spent in the light every 5 minutes for 30 minutes during Test 2 (two-way ANOVA [time and treatment], Treatment factor p=0.3112; Tukey's multiple comparison against veh-veh group [ns]). Panel D shows the average time spent in the light during Test 2 (one-way ANOVA; p=0.3112; Tukey's multiple comparison against veh-veh group [ns]).

Figure 10:
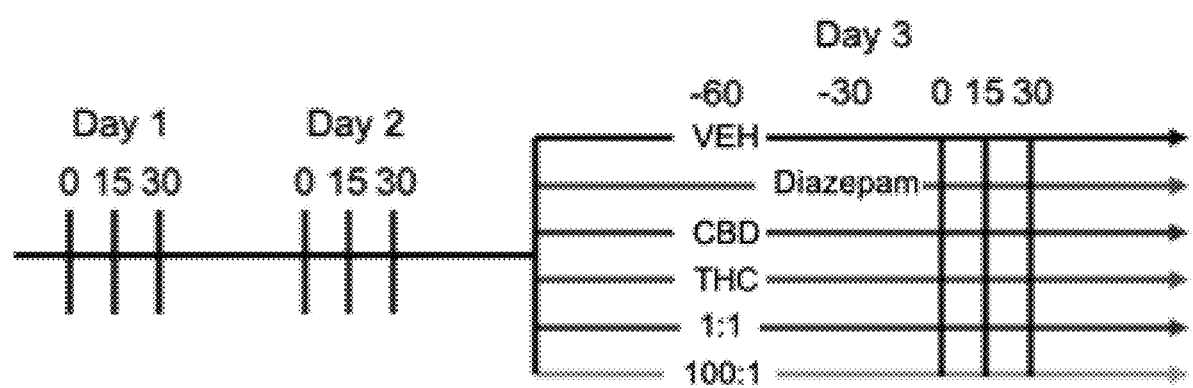
FIG. 10 shows the experimental design for the rotarod assay.

FIG. 9 shows that SNP+veh seems to decrease the time in light (trend only) (FIG. 10). The second cohort is needed to gain the power of significance.

B. Motor Function—Rotarod

The experimental design is presented in FIG. 10. Animals used in this experiment were also used for light aversion and spatial memory, and were tested a third time in the rotarod assay. Briefly, two weeks after the last Y-maze run, animals were subjected to 3 consecutive days of rotarod assay. The first two days were used for habituation, then animals were divided in 6 different treatment groups:

negative control group: vehicle (sunflower oil),
positive control group: diazepam (5 mg/kg i.p.),
CBD (100 mg/kg),
THC (1 mg/kg),
1:1 (1 mg/kg of both CBD and THC), and
100:1 (100 mg/kg of CBD and 1 mg/kg of THC).

All treatments were administered 60 minutes prior to the third day of rotarod assay, except for diazepam which was administered 30 minutes prior to the assay.

Figure 11:
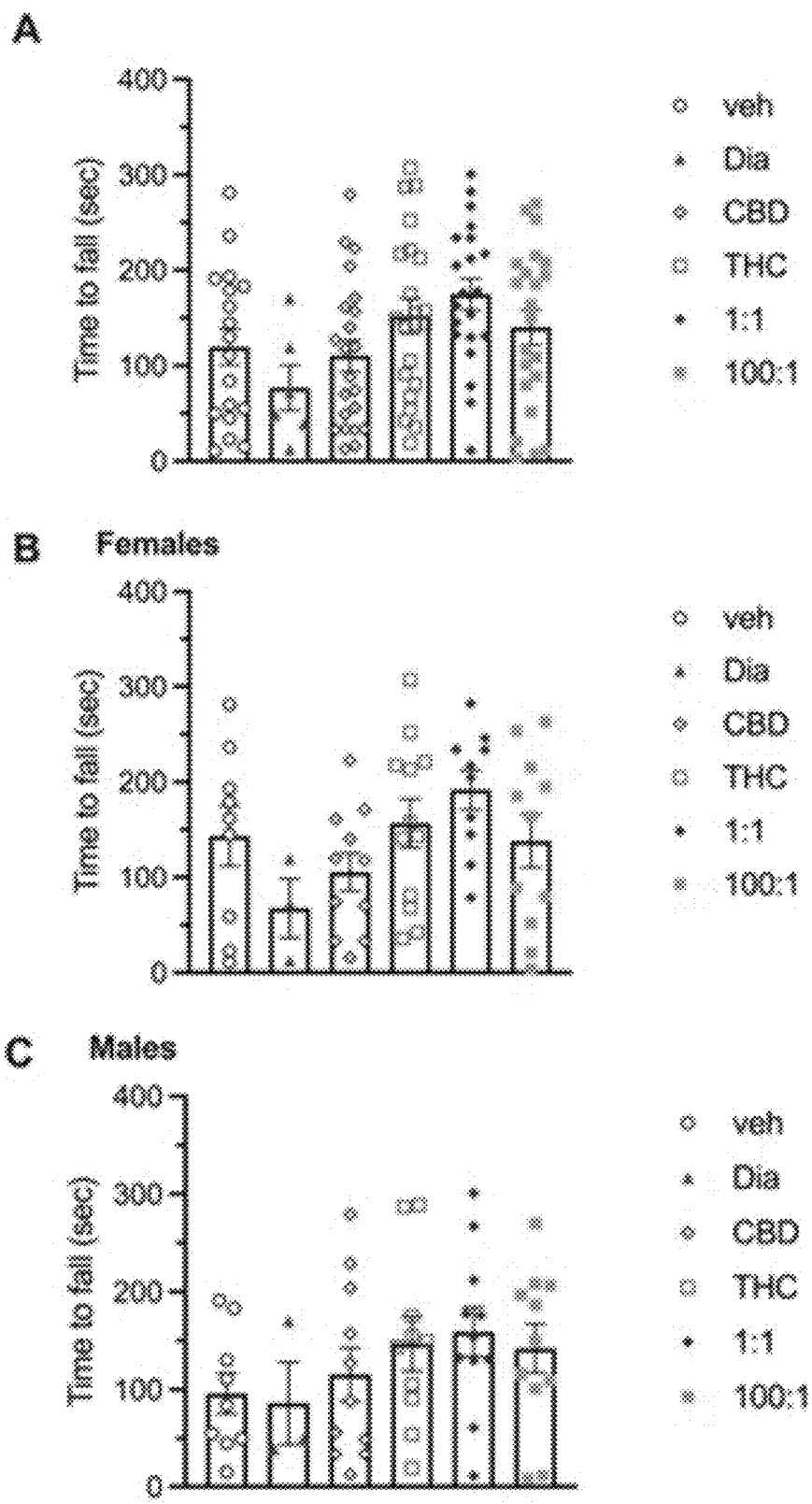
FIG. 11 shows the effect of different ratios of CBD and THC on locomotor activity assessed by the rotarod. Panel A shows the results in all mice. Panel B shows the results in female mice. Panel C shows the results in male mice.

Effect of CBD, THC and CBD:THC Ratios on Locomotor Activity Assessed by the Rotarod:

FIG. 11 shows the locomotor activity results. Panel A shows results for all mice presented as the average across all 3 trials on treatment day (Day 3) (One-way ANOVA, treatment factor p=0.0408; Tukey's multiple comparison showed no differences between groups). Panel B shows results for female mice presented as the average across all 3 trials on treatment day (One-way ANOVA treatment factor p=0.132). Panel C shows results for male mice presented as the average across all 3 trials on treatment day (One-way ANOVA treatment factor p=0.452).

Animals receiving vehicle stayed on the rod for an average of 120 seconds. Animals receiving diazepam (5 mg/kg, i.p.) showed a robust decrease in time to fall from the rod, which will likely become significant as animals are added to this group. Compared to those two control groups, CBD alone and 100:1 treatment yielded similar results as the vehicle group. THC alone and 1:1 groups showed increases in time to fall that were not significant, likely because of the variability within groups. In any case, none of the treatments induced a decrease in motor function. If anything, some induced an increase. When separated by sex, results show the same trends.

C. Spatial Memory

Figure 12:
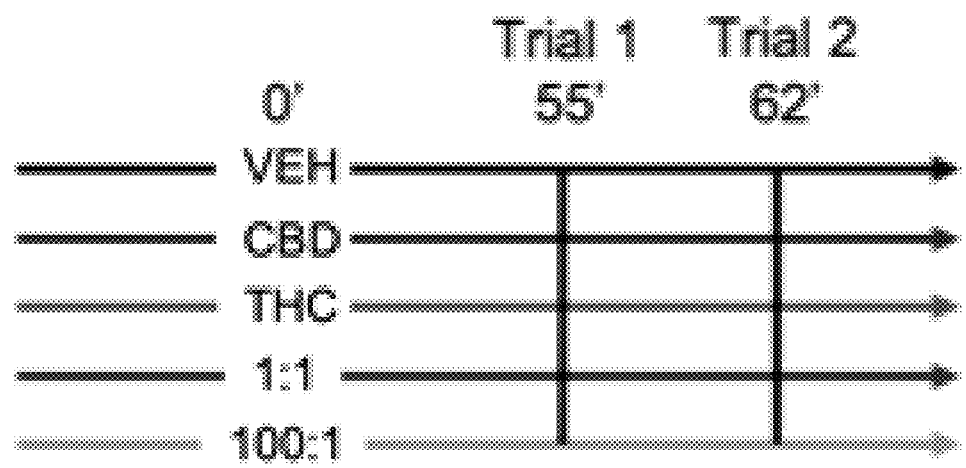
FIG. 12 shows the experimental design for the Y-maze assay.
Figure 13:
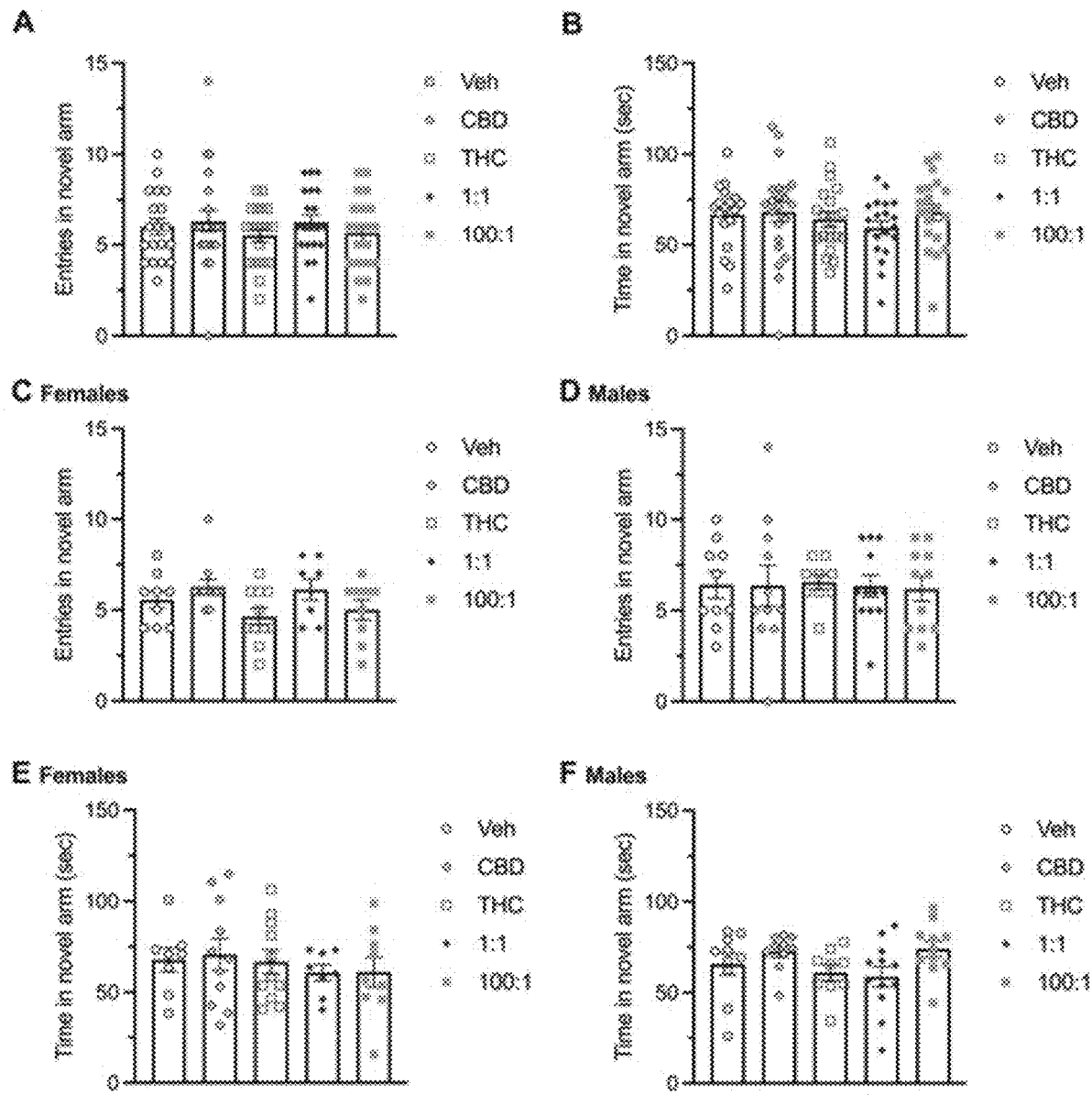
FIG. 13 shows the effect of different ratios of CBD and THC on spatial memory. Panel A shows the number of entries in the novel arm during the trial in all mice. Panel B shows the time spent in the novel arm during the trial in all mice. Panel C shows the number of entries in the novel arm during the trial in female mice. Panel D shows the number of entries in the novel arm during the trial in male mice. Panel E shows the time spent in the novel arm during the trial in female mice. Panel F shows the time spent in the novel arm during the trial in male mice.

The experimental design is presented in FIG. 12. Animals used in this experiment were also used for light aversion (and later rotarod). Briefly, two weeks after the last light aversion run, animals were subjected to 2 trials in the Y maze separated by a 2-min intertrial period. Animals were divided into 5 groups as follows:

negative control group: vehicle (sunflower oil),
CBD (100 mg/kg),
THC (1 mg/kg),
1:1 (1 mg/kg of both CBD and THC),
100:1 (100 mg/kg of CBD and 1 mg/kg of THC).

All treatments were administered 55 minutes prior to the first 5-minute trial, and therefore 62 minutes before the second 2-minute trial. No effect of CBD, THC and CBD:THC ratios on spatial memory was assessed by the Y-maze.

The results are shown in FIG. 12. Panel A shows the number of entries in the novel arm during trial 2 in all mice (one-way ANOVA treatment factor p=0.66). Panel B shows the time spent in the novel arm during trial 2 in all mice (One-way ANOVA treatment factor p=0.624). Panel C shows the number of entries in the novel arm during trial 2 in female mice (One-way ANOVA treatment factor p=0.083). Panel D shows the number of entries in the novel arm during trial 2 in male mice (One-way ANOVA treatment factor p=0.998). Panel E shows the time spent in the novel arm during trial 2 in female mice (One-way ANOVA treatment factor p=0.846). Panel D shows Animals receiving vehicle enter the novel arm 6 times on average over the second trial, for an average of 66.7 seconds. All other treatment groups showed similar results. There was no sex difference in the number of entries, or in the time spent in the arm.

Figure 14:
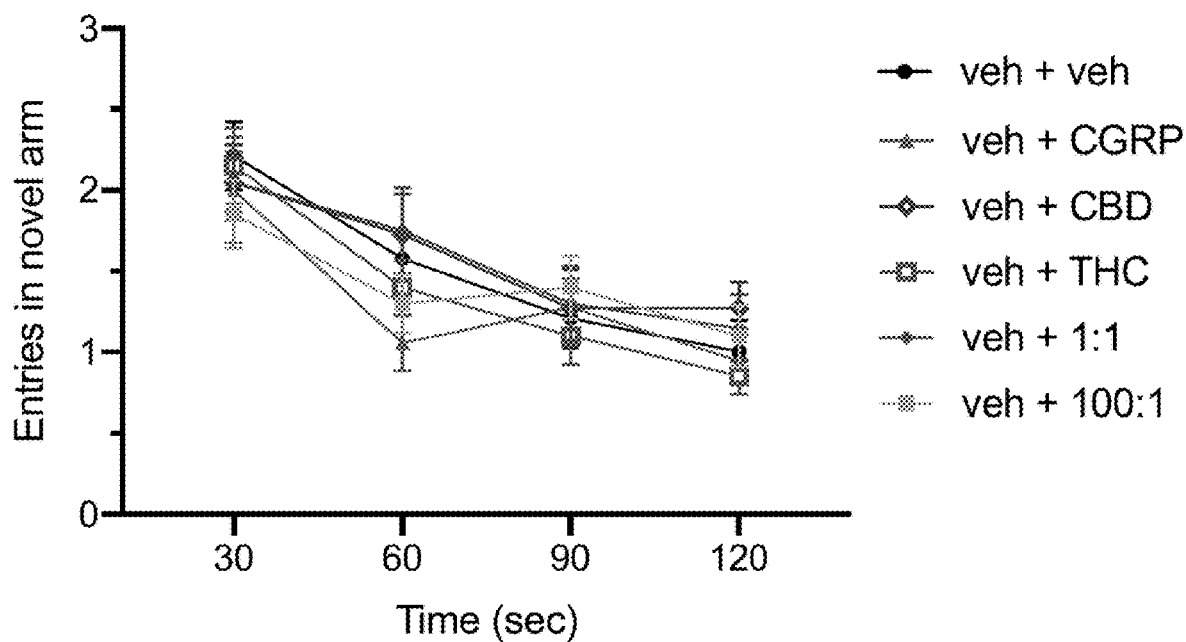
FIG. 14 shows the effect of different ratios of CBD and THC and CGRP on spatial memory. The top panel shows the number of entries in the novel arm over time. The bottom panel shows the average number of entries in the novel arm for mice in each cohort.
Figure 14:
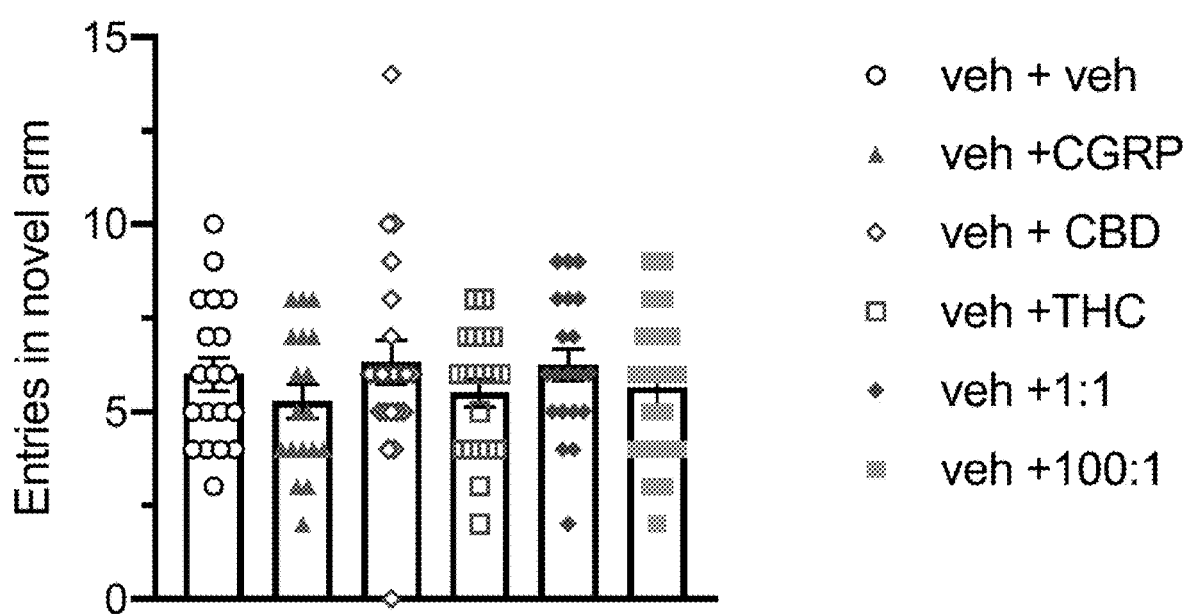

An experiment was also conducted with a positive control by adding a composition including CGRP, the results for which are shown in FIG. 14. The top panel shows the number of entries in the novel arm after every 30 seconds for two minutes. The bottom panel shows the average number of entries in the novel arm for each cohort.

D. Additional Experiments to be Conducted

Experiments directed to assessing the effects of CBD and THC on spontaneous pain, tactile allodynia, motor function, object memory, depression, and anxiety will be conducted.

Facial signs of discomfort (spontaneous pain): An automated facial grimace assay based on the mouse grimace scale developed in 2010, which measures spontaneous pain by scoring facial features (eye closure, nose and cheek bulge, ear position and whiskers orientation) may be used. Several groups have shown that different models of migraine display this phenotype in mice. In the automated version, video monitoring of eyelid closure and assessment of facial features enables objective characterization of spontaneous pain on a linear scale.

Tactile allodynia: As an indicator of evoked pain, tactile allodynia measured by the application of von Frey filaments is the most accepted pain assay in preclinical settings. In addition, the perception of touch as a painful stimulus is reported by nearly half of migraineurs. Several groups have reported that mice models of migraine presented enhanced sensitivity to tactile stimulation.

Wheel activity (motor function): The wheel activity is used to measure rodent physical activity and motivation. Mice are enclosed in a wheel for 2 hours, during which they are free to stay immobile or run at will. The number of wheel revolutions, speed, and time spent moving is monitored and reflect any sedative or stimulant effect of the drugs. Novel object recognition (object memory): In this cognitive assay, a mouse is presented with two similar objects during the first session, and then one of the two objects is replaced by a new object during a second session. The amount of time taken to explore the new object provides an index of recognition memory. Animals with impaired object memory will spend the same amount of time exploring the two objects during the second session, and non-impaired animals will spend more time interacting with the novel object.

Tail suspension assay (depression): Mice that are visually isolated are suspended 50 cm above the floor by tape placed approximately 1 cm from the tip of their tail. Immobility time is recorded during a 6 min period. Mice are considered immobile only when they hang passively and completely motionless.

Zero maze (anxiety): This test relies on two conflicting innate behaviors: exploring a novel environment and avoiding elevated and open spaces considered risky. The apparatus consists of two open (anxiogenic) and two enclosed (safe) elevated arms that form a zero or circle. Mice are left to explore for 5 minutes and time spent exploring enclosed versus open arms indicates the anxiety level of the animal.

Example 6: CSD Experiments

The objective of the CSD experiments was to determine whether a combination of CBD and THC at a ratio of 100:1 and 30:1 normalizes the altered CSD properties and behavioral responses in FHM1 mice compared to those in WT mice. At a later stage it will be decided whether a combination of CBD and THC is more efficacious than CBD (100 mg/kg) and THC (1 mg/kg) alone. All proposed experiments were conducted in awake freely moving mice. Optogenetics were used to induce CSD (Houben et al. J Cereb Blood Flow Metab 2017; 37:1641-55) as this method allowed for assessing the effect of treatment on CSD without the negative confounder of anesthesia.

Aim 1: Effects of CBD/THC on CSD Characteristics in WT and FHM1 Mice

The objective was to determine whether an acute dose of i.p. injected CBD/THC normalizes CSD properties (i.e. threshold, propagation rate and basic features amplitude, slope and width) with expected possible stronger effects in FHM1 compared to WT mice. Mice of both sexes were studied. CSD threshold experiments were performed in Thy1-ChR2 (Thy1-driven expression of channelrhodopsin-2)/FHM1 and Thy1-ChR2/WT mice. In the experiments, optic fibers for optogenetic CSD induction were placed on the skull (left hemisphere) and on the dura (right hemisphere). It was expected that the most reliable data would be obtained from the fiber placed on the dura. The data obtained from the fiber on the skull was expected, however, to directly match the data from Aim 2 below, where the fiber is also placed on the skull. Recording electrodes were placed intracortically to accurately assess CSD propagation rate, amplitude, slope and width. Because of this configuration of optic fiber and recording electrode placement a different set of mice was needed for Aim 1 than for Aim 2. For each mouse we first performed threshold measurements on multiple days (to establish a stable baseline) before we tested a dose of CBD/THC. To reduce the number of mice and maximize the outcome of the experiment, we tested 2 doses and vehicle in each mouse for a period of 2 weeks.

The groups in the experiment included a group of Thy1-ChR2/FHM1 mice (N=10) and Thy1-ChR2/WT mice (N=10). Each group had an equal number of males and females. The groups were tested with a composition comprising a ratio of 100:1 CBD:THC (100 mg/kg CBD and 1 mg/kg THC), 30:1 (CBD:THC, 30 mg/kg CBD and 1 mg/kg THC), and a vehicle.

Serial CSD threshold assessments performed in relation to CBD:THC administration 1 hour prior to the CSD test (2 dosages, 100:1 & 30:1); (N=3 blinded WT & FHM1 mice, 10 experiments per mouse). Serial CSD threshold assessments were also performed in relation to CBD:THC administration 30 min prior to the CSD test: (N=2 blinded WT&FHM1 mice; 6 experiments per mouse). The repeated CSD threshold paradigm provides a basis for judging the effects of CBD:THC on CSD features. The expected intra-variability in threshold values also warranted inclusion of repeated baseline measures in between drug tests. In addition to CSD threshold, the CSD speed, amplitude, and width were measured.

Figure 15A:
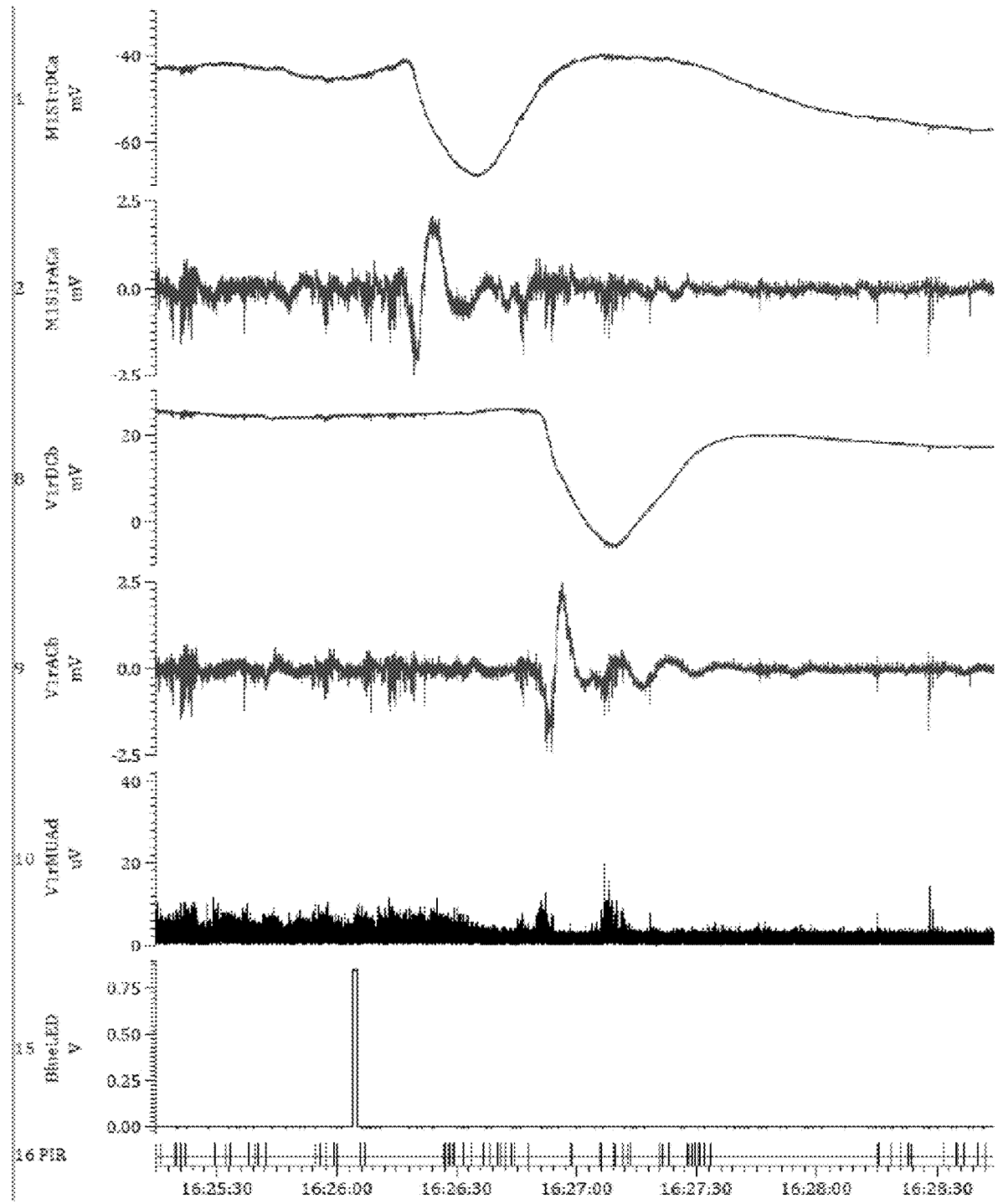
FIGS. 15A-C show the effects of CBD:THC on CSD characteristics including threshold, DC-features, and speed, at baseline, after administration of a vehicle, and after administration of a composition containing 100:1 CBD/THC.
Figure 15B:
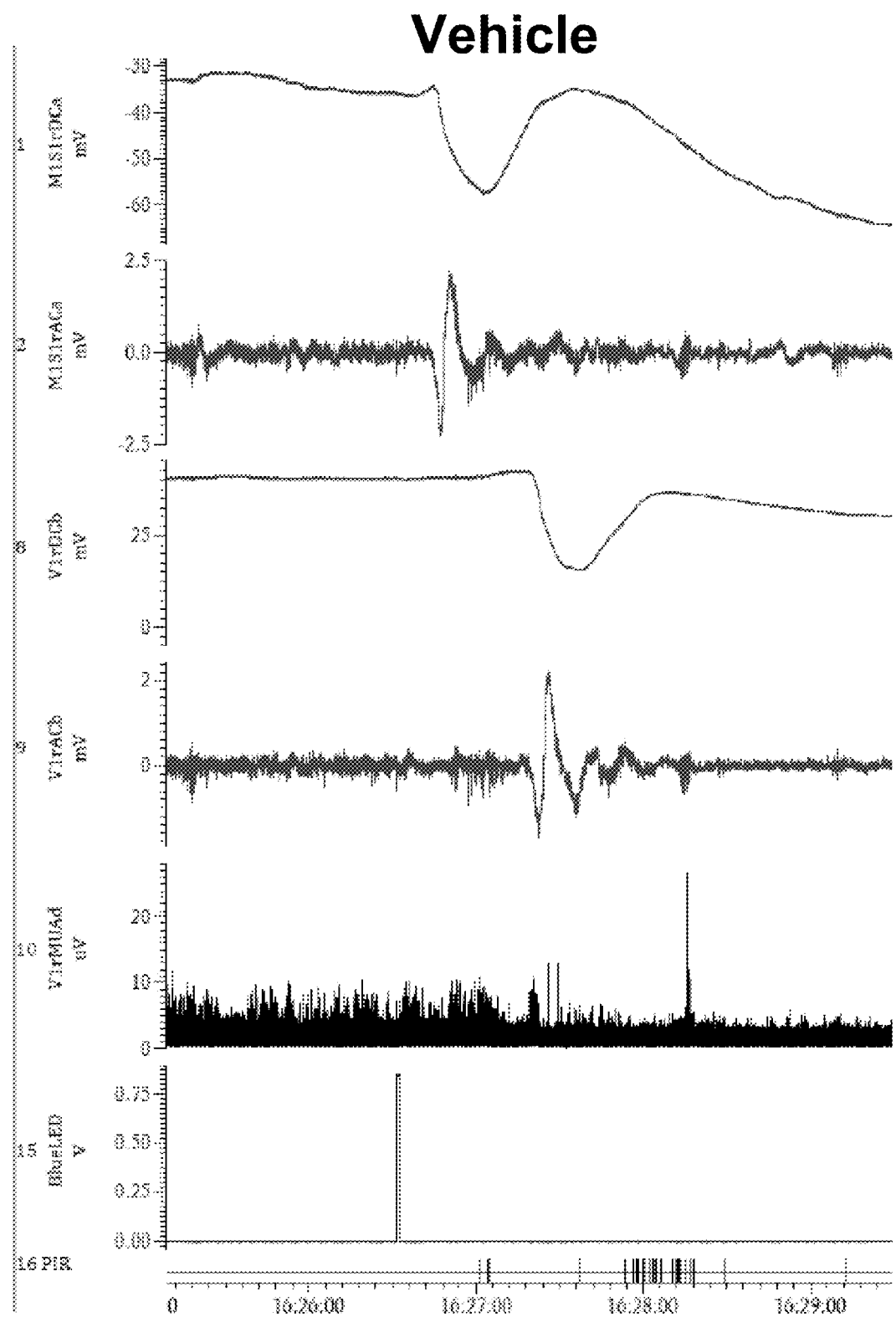
Figure 15C:
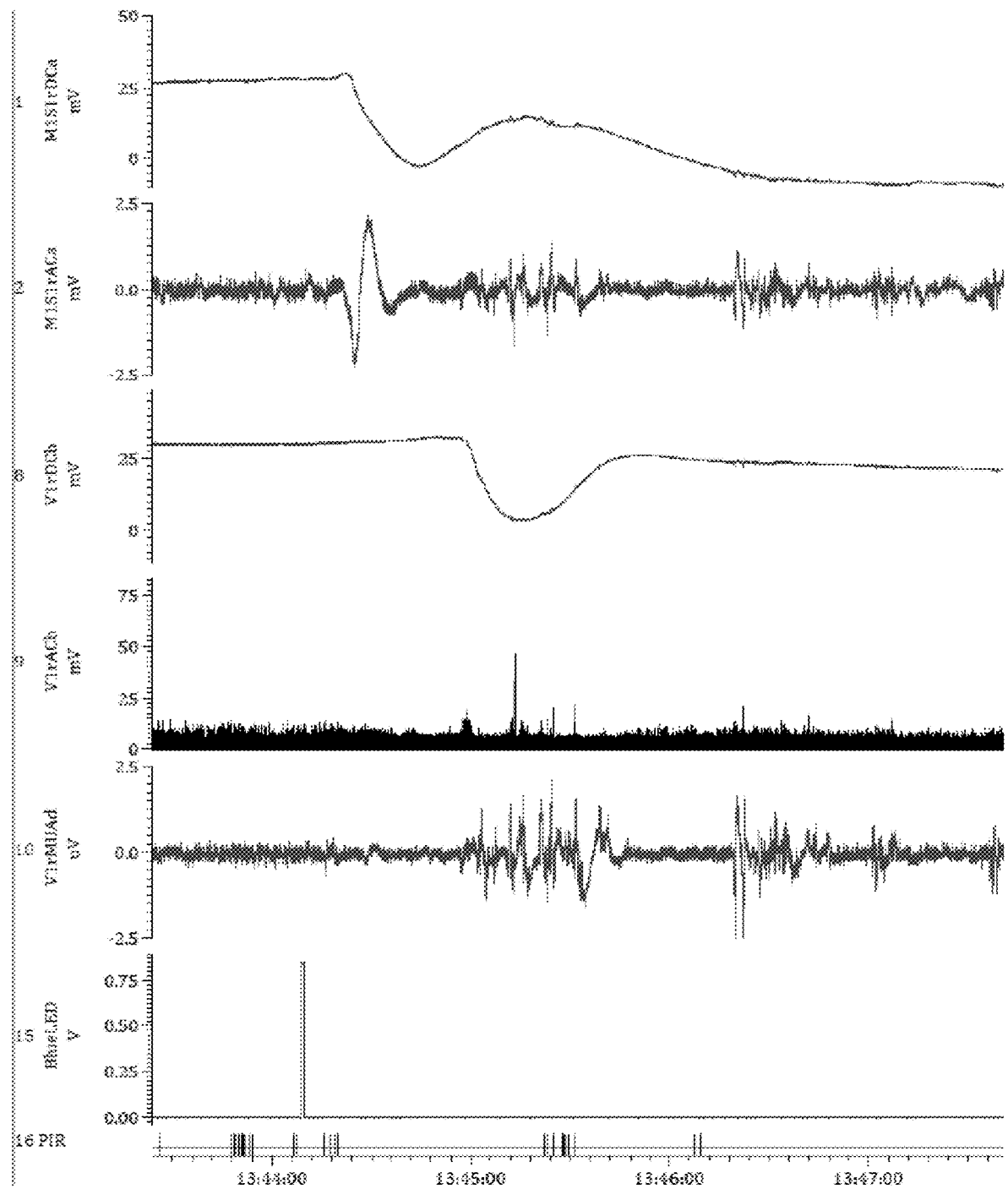

Exemplary data from 1 hour post-injection from the experiment is shown in FIG. 15. The data showed CSD can be successfully induced after CBD:THC administration with no overt changes in CSD threshold values for both 100:1 and 30:1 dosages and the 1-hour and 30-minute pre-administration times. No adverse effects of CBD:THC in aggravating CSD in either WT or FHM1 mice were observed.

Figure 16:
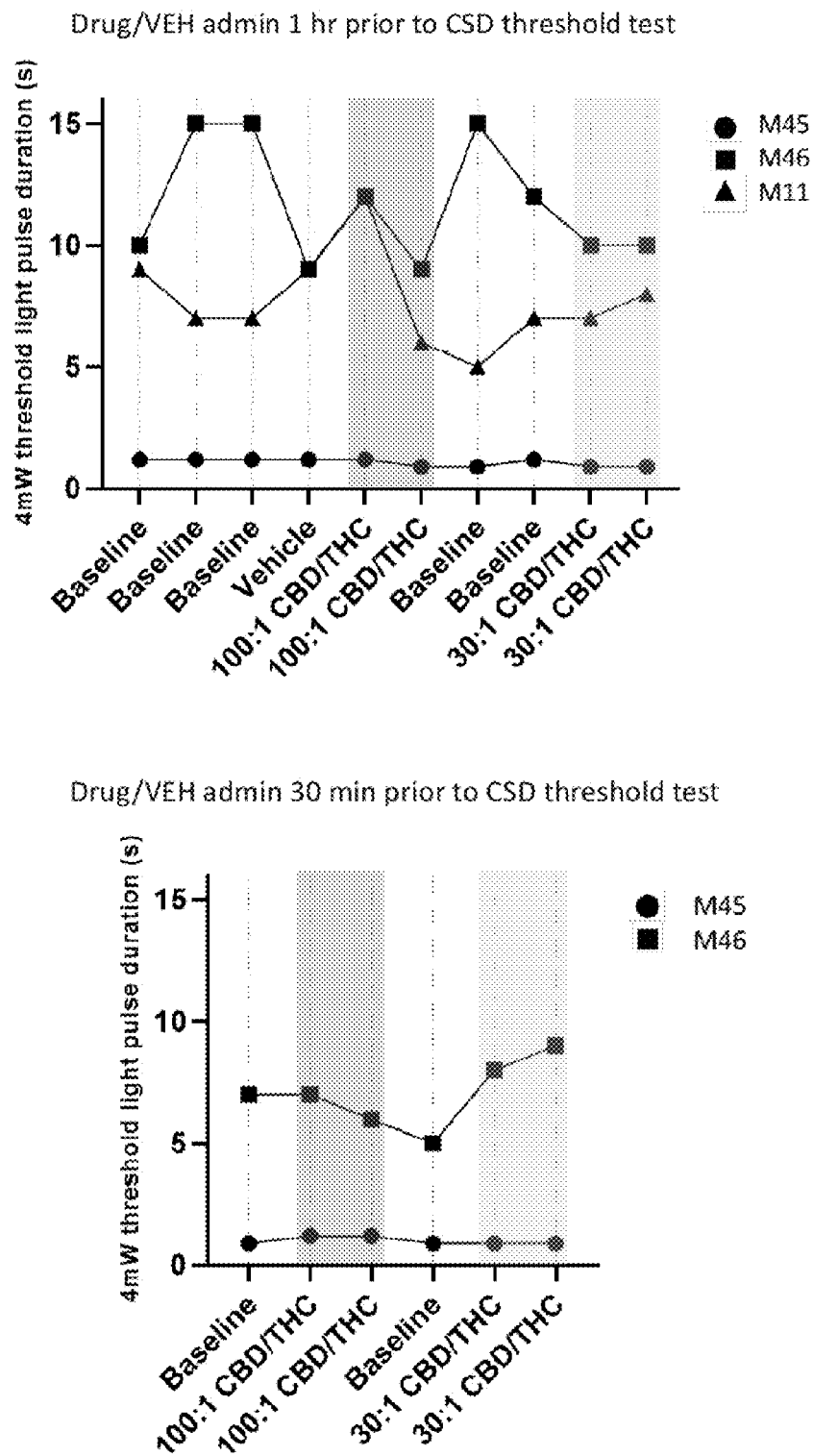
FIG. 16 shows the effects of CBD:THC on CSD threshold after at 1 hour post-injection and 30 minutes post-injection.
Figure 17:
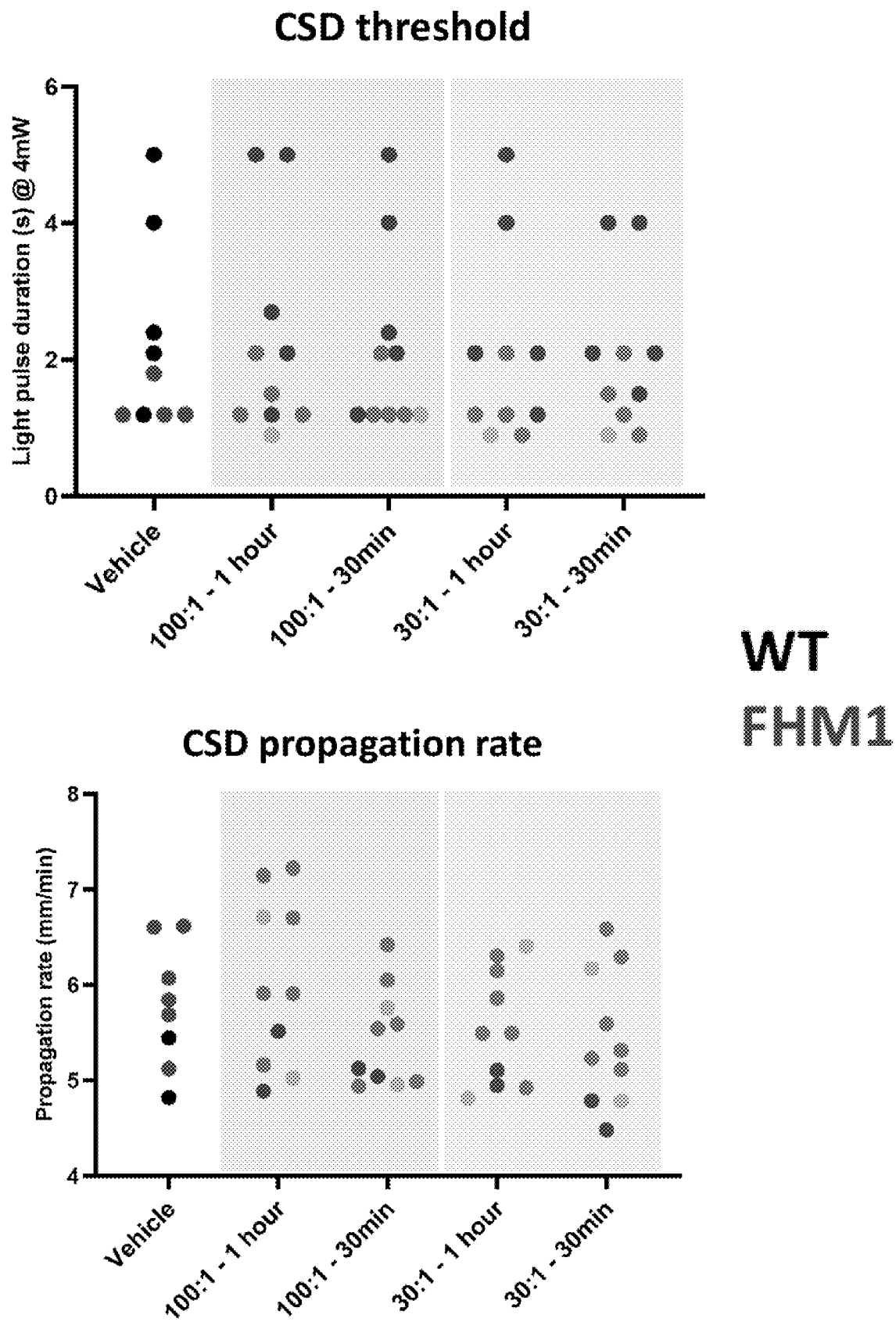
FIG. 17 shows the effects of CBD:THC on CSD threshold and propagation rate at both 1 hour post-injection and at 30 minutes post-injection.

Chronic recordings in freely behaving mice allowed for repeated CSD threshold tests. Intra-individual variation across days required repeated baseline tests before and around drug tests. From April 2021 onward, the design was adapted to include both 1-hour and 30-minute pre-administration of CBD:THC. The preliminary CSD threshold results for 1 hour post-injection and 30 minutes post-injection are shown in FIGS. 16 and 17. The preliminary data show no overt increase or decrease in CSD threshold following injection of CBD:THC.

Figure 18A:
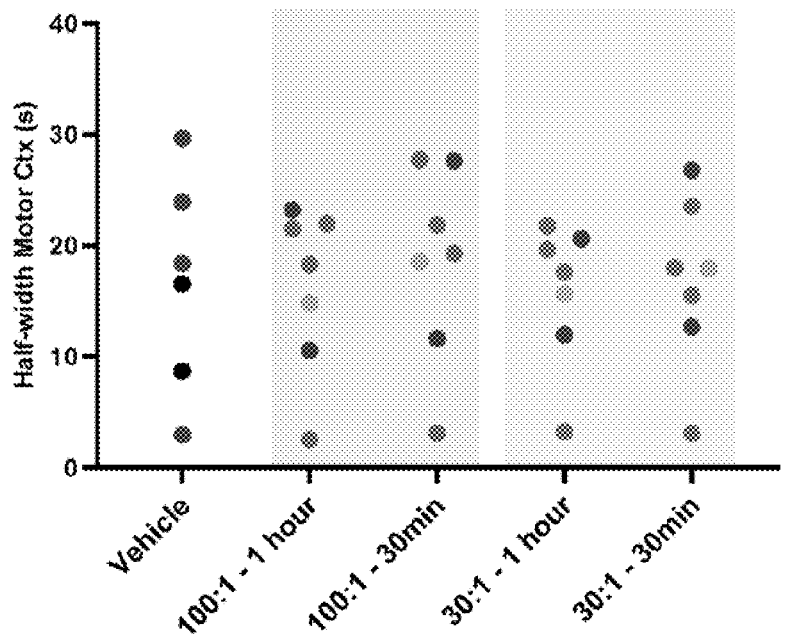
FIGS. 18A and 18B show the effects of CBD:THC on CSD half-width and amplitude at both 1 hour post-injection and 30 minutes post-injection in the motor cortex and the visual cortex, respectively.
Figure 18A:
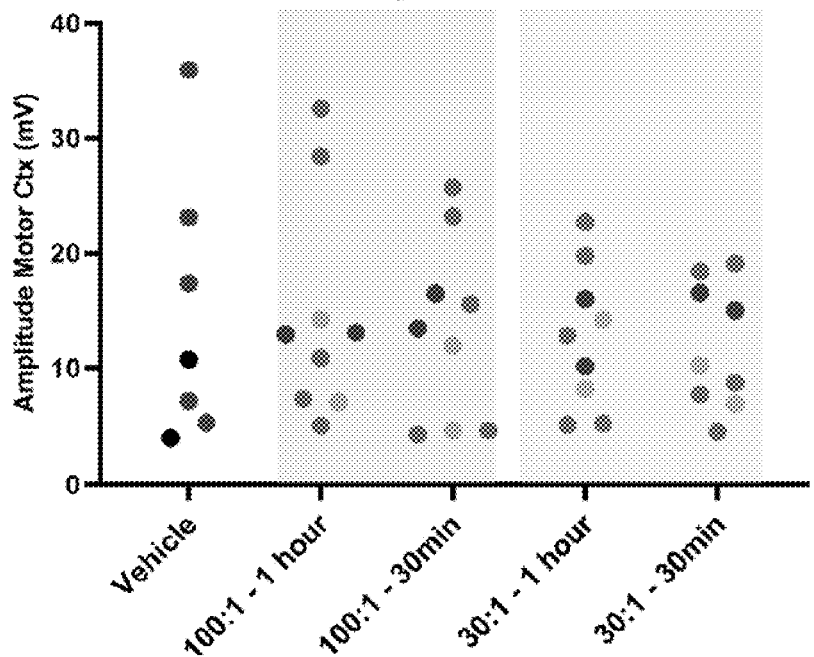
Figure 18B:
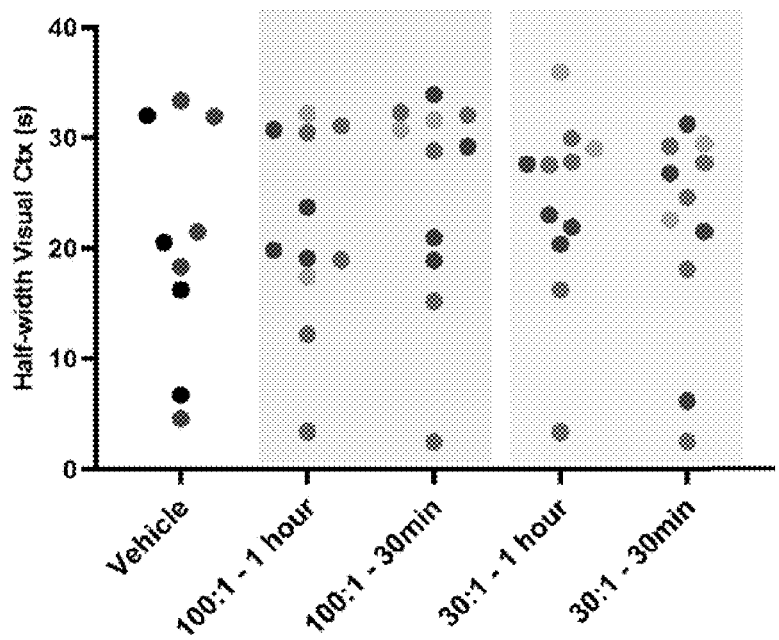
Figure 18B:
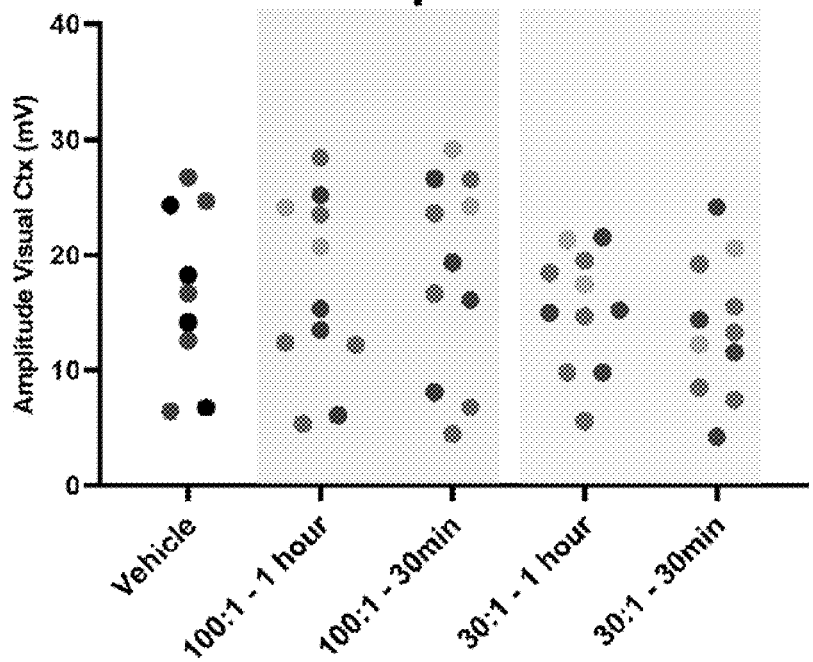

The motor cortex and visual cortex CSD half-width and amplitude was assessed. The results are shown in FIGS. 18A and 18B for the motor cortex and visual cortex, respectively. Analysis of the data is ongoing; although, the preliminary data show no overt increase or decrease in CSD half-width or amplitude following injection of CBD:THC.

Aim 2: Effects of CBD/THC on CSD-Related Pain-Relevant Behavior, i.e., Mouse Grimace Score and Allodynia The objective was to determine whether an acute dose of i.p. injected CBD/THC normalizes CSD-related pain-relevant behavior, with possible stronger effects in FHM1 mice compared to WT mice. Behavioral measurements were conducted using a modified version of the mouse grimace scale (MGS) test (Langford et al. Nat Meth 2010; 7:447-9) for head-pain assessment (part A), and von Frey filament testing of the periorbital region or hind paw for allodynia assessment (part B). Both the optic fiber for optogenetic CSD induction and recording electrodes were placed in one hemisphere on the skull to minimize confounding effects by invasive surgery on pain-relevant behavior outcome. CSD was induced by suprathreshold intensity light stimulation.

Given the nature of the experiments, the head-pain assessment and allodynia assessment could not be conducted in the same mouse. MGS was measured using a platform that is placed directly in front of the optogenetic cage, whereas the allodynia experiments were performed in a different room. Also, it is not advisable to perform these behavioral tests in the same mouse, as one assessment may confound the other assessment. Hence, below, experiments were divided in (part A) MGS assessment and (part B) allodynia assessment. Please note that data of the CSD readouts in the two groups can be combined, allowing for post hoc testing for possible male—female differences, in case the effect size is large enough and/or the effect of the drug is sex-specific.

Part A: MGS Measurement: The groups in the experiment included a group of Thy1-ChR2/FHM1 mice (N=6) and Thy1-ChR2/WT mice (N=6). Each group had an equal number of males and females. The groups were tested with a composition comprising a ratio of 100:1 CBD:THC (100 mg/kg CBD and 1 mg/kg THC), 30:1 (CBD:THC, 30 mg/kg CBD and 1 mg/kg THC), and a vehicle.

Figure 19A:
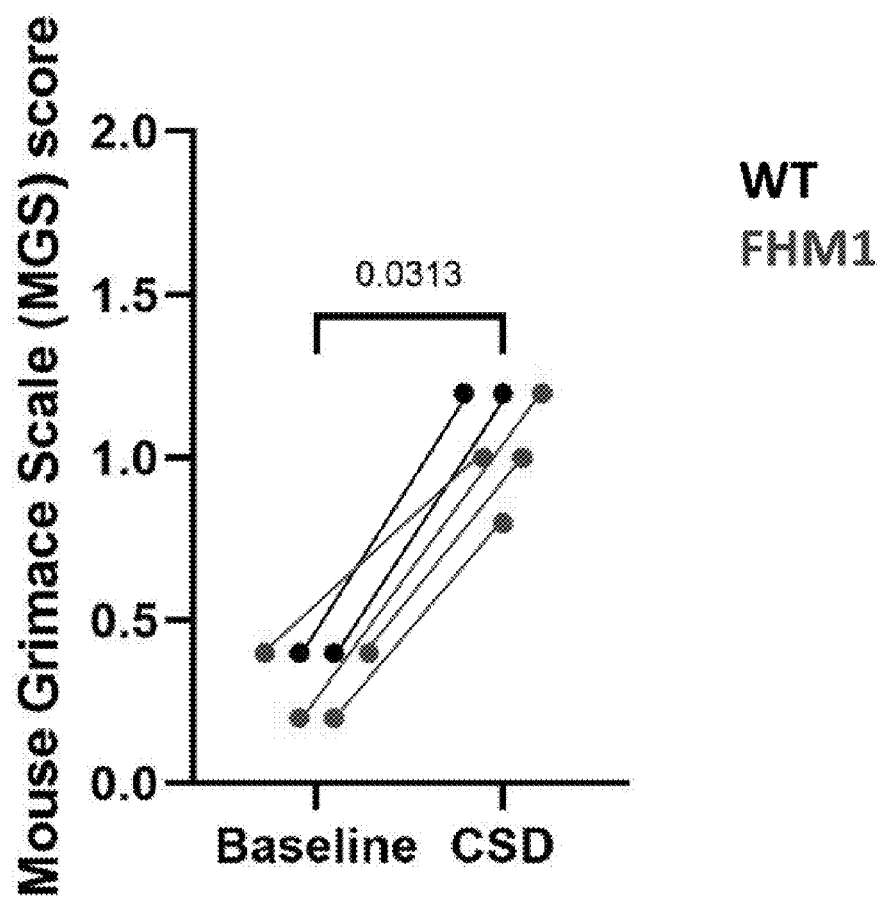
FIGS. 19A-19B shows the effects of CBD:THC on CSD-related pain behavior.
Figure 19B:
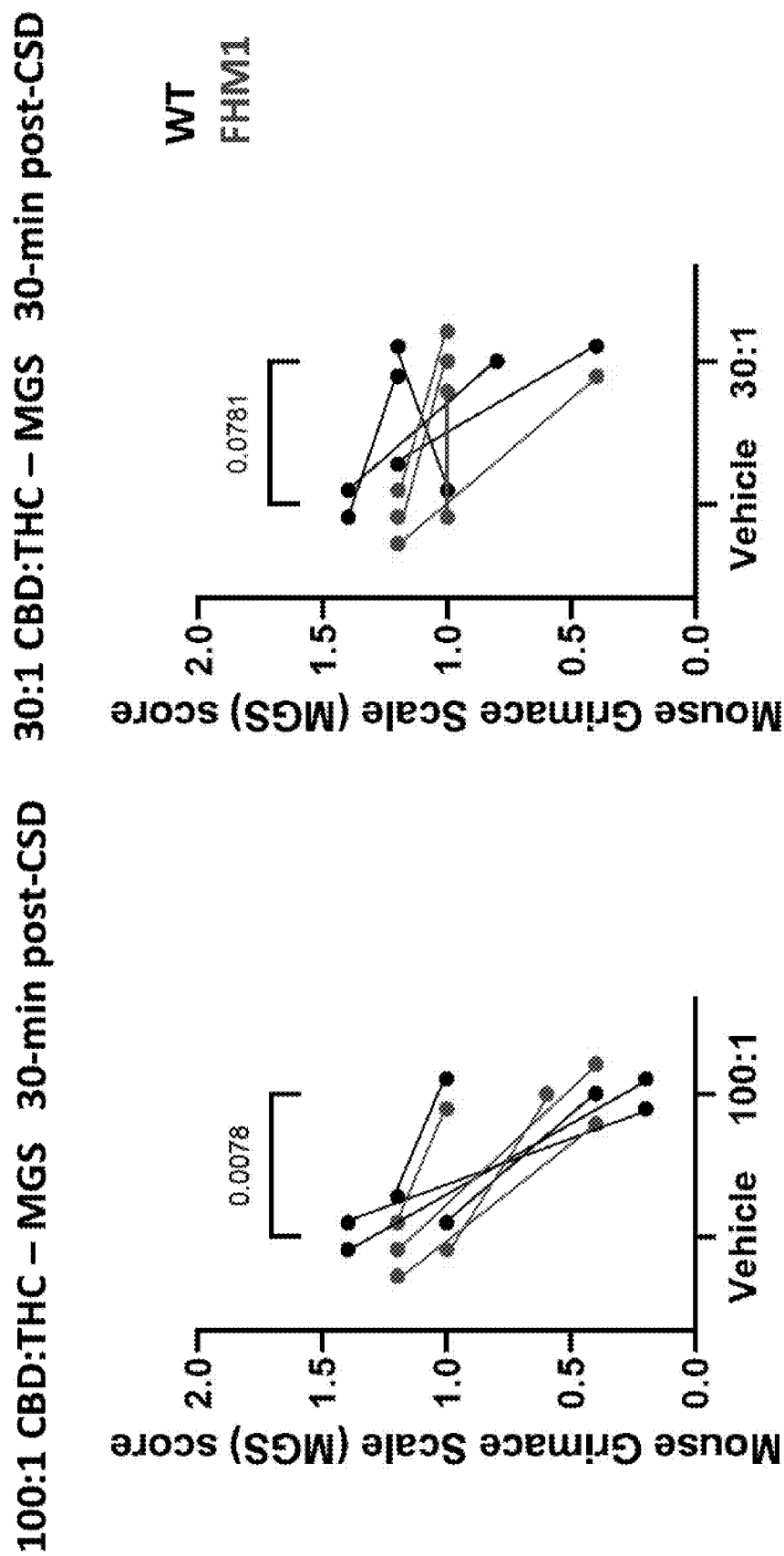

Results for the MGS Measurement experiments are shown in FIGS. 19A-B. FIG. 19A shows MGS score at baseline and with CSD. The results show that CSD causes increased headache pain behavior as measured by MGS. FIG. 19B shows the change in MSG score with different ratios of CBD:THC. As can be seen, administration of 100:1 CBD:THC and 30:1 CBD:THC reduced MSG score ($p=0.0078$ and $0.0781$, respectively).

Part B: Allodynia Measurement: The groups in the experiment included a group of Thy1-ChR2/FHM1 mice (N=6) and Thy1-ChR2/WT mice (N=6). Each group had an equal number of males and females. The groups were tested with a composition comprising a ratio of 100:1 CBD:THC (100 mg/kg CBD and 1 mg/kg THC), 30:1 (CBD:THC, 30 mg/kg CBD and 1 mg/kg THC), and a vehicle.

Preliminary analysis of MGS from four mice suggested no pronounced effect of either 100:1 or 30:1 CBD:THC with 1-hour pre-administration. Additionally, there were no indications for adverse pain-inducing effects of the administration of the sunflower-oil vehicle, nor of CBD:THC, in either WT or FHM1 mice.

Aim 3: Effects on Timing of Allodynia Measurement in the Basal State

The timing of effects of treatment in mice that did not undergo CSD was studied. As a consequence the animals do not need to express Thy1-ChR2. It was hypothesized that administration of CBD and THC would normalize the enhanced allodynia threshold in FHM1 mice to WT levels. Assessing of allodynia measurement were performed at 24, 48 and 72 hours after injection by a hindpaw withdrawal threshold. To reduce the number of mice and maximize the outcome of the experiment, 2 doses and a vehicle were tested in each mouse for a period of 2 weeks.

The groups in the experiment included a group of FHM1 mice (N=10) and WT mice (N=10). Each group had an equal number of males and females. The groups were tested with a composition comprising a ratio of 100:1 CBD:THC (100 mg/kg CBD and 1 mg/kg THC), 30:1 (CBD:THC, 30 mg/kg CBD and 1 mg/kg THC), and a vehicle.

Figure 20:
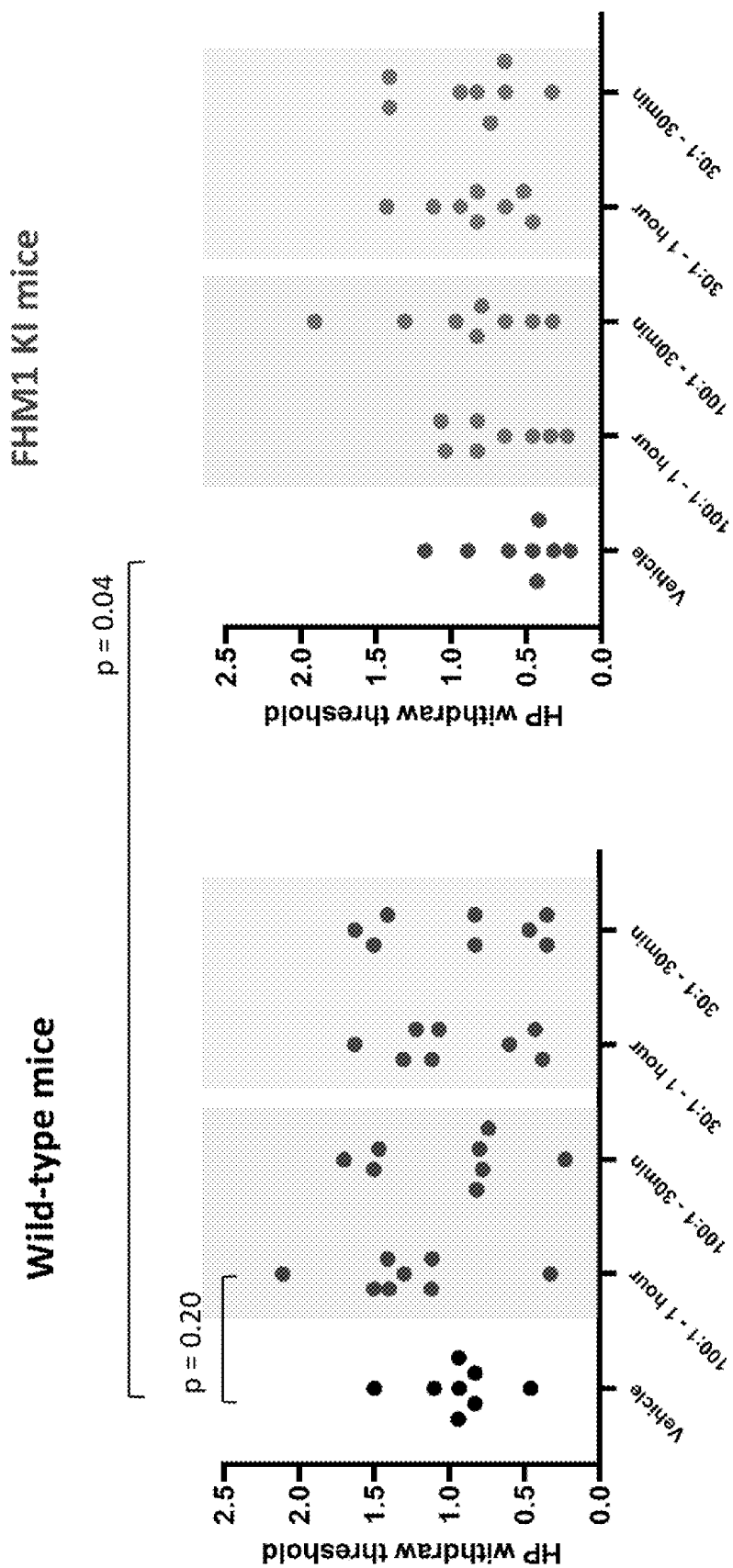
FIG. 20 shows the effects of CBD:THC on allodynia from a hindpaw withdrawal threshold test for wild-type mice and for FHM1 KI mice.

Preliminary analysis indicates a variation between the untreated groups and the vehicle groups. It is not known if the variation across repeated measurements is different for WT and FHM1 mice. Therefore, in parallel with the drug tests, studies will be performed to establish the stability of repeated allodynia measures over time also in the absence of treatment. Preliminary results of the hindpaw withdrawal threshold tests are shown in FIG. 20. Although there is no consistent effect seen of CBD:THC on allodynia, the preliminary data may show an effect of 30:1 CBD:THC administered 30 minutes prior to testing.

What is claimed is:

1. A method of treating migraine pain, the method comprising administering a composition comprising a pharmaceutically effective amount of CBD and THC to a subject in need thereof, thereby reducing migraine pain in the subject, wherein the weight ratio of CBD to THC is about 100:1.

2. The method of claim 1, wherein the administering is accomplished via injection.

3. The method of claim 1, wherein the treatment is effective within 2 hours post-administration.

4. The method of claim 3, wherein the treatment is effective within 30 minutes post-administration.

5. The method of claim 4, wherein the treatment is effective within 15 minutes post-administration.

6. The method of claim 1, wherein the migraine pain is acute migraine pain.

7. The method of claim 1, wherein the migraine pain is measured by a pain scale.

8. The method of claim 1, wherein the THC and the CBD are at least 90 wt % pure.

9. The method of claim 1, wherein the composition further comprises at least one minor cannabinoid.

10. The method of claim 9, wherein the at least one minor cannabinoid is at least 90 wt % pure.

11. The method of claim 9, wherein the at least one minor cannabinoid is selected from the group consisting of CBG, CBGA, CBN, CBNA, THCV, THCA, CBC, CBCA, CBDV, and D8-THC.

12. The method of claim 1, wherein at least one biomarker of central and peripheral sensitization is modulated as a result of the administration.

13. The method of claim 12, wherein the at least one biomarker is selected from the group consisting of NMDA, glutamate, CGRP, FAAH, Substance P, 5-HT, NO, GABA, NGF, serotonin, dopamine, AEA, and 2-AG.

14. The method of claim 1, wherein the composition comprises an amount of CBD to reduce unwanted side effects or risk factors associated with THC.

15. The method of claim 14, wherein the unwanted side effects or risk factors include psychoactivity, psychosis, anxiety, paranoia, dizziness, confusion, increased heart rate, memory impairment, or combinations thereof.

16. A method of treating migraine pain, the method comprising administering a composition comprising a pharmaceutically effective amount of at least one minor cannabinoid in combination with THC and CBD to a subject in need thereof, thereby reducing migraine pain in the subject, wherein the weight ratio of CBD to THC is about 100:1.

17. The method of claim 16, wherein the composition comprises an amount of CBD to reduce unwanted side effects or risk factors associated with THC.

18. The method of claim 17, wherein the unwanted side effects or risk factors include psychoactivity, psychosis, anxiety, paranoia, dizziness, confusion, increased heart rate, memory impairment, or combinations thereof.

19. The method of claim 16, wherein the treatment is effective within 2 hours post-administration.

* * * * *

UNITED STATES PATENT AND TRADEMARK OFFICE
CERTIFICATE OF CORRECTION

PATENT NO. : 12,029,721 B2
APPLICATION NO. : 18/208017
DATED : July 9, 2024
INVENTOR(S) : George D. Pappas It is certified that error appears in the above-identified patent and that said Letters Patent is hereby corrected as shown below:

In the Specification

Column 1, Lines 20-21, cancel the text reading:
"the National Institute on Drug Abuse"

And replace it with:
--the National Institutes of Health--

Signed and Sealed this
Seventeenth Day of September, 2024

Katherine Kelly Vidal
*Director of the United States Patent and Trademark Office*